US010632325B2

(12) United States Patent
Lim

(10) Patent No.: US 10,632,325 B2
(45) Date of Patent: Apr. 28, 2020

(54) METHOD, SYSTEM AND APPARATUS FOR NON-INVASIVE NEUROSTIMULATION THERAPY OF THE BRAIN

(71) Applicant: Lew Lim, Toronto (CA)

(72) Inventor: Lew Lim, Toronto (CA)

(*) Notice: Subject to any disclaimer, the term of this patent is extended or adjusted under 35 U.S.C. 154(b) by 356 days.

(21) Appl. No.: 15/548,015

(22) PCT Filed: Nov. 23, 2015

(86) PCT No.: PCT/IB2015/059041
§ 371 (c)(1),
(2) Date: Aug. 1, 2017

(87) PCT Pub. No.: WO2016/151377
PCT Pub. Date: Sep. 29, 2016

(65) Prior Publication Data
US 2018/0015301 A1   Jan. 18, 2018

Related U.S. Application Data

(60) Provisional application No. 62/136,411, filed on Mar. 20, 2015.

(51) Int. Cl.
*A61N 5/06* (2006.01)
*A61N 5/067* (2006.01)

(52) U.S. Cl.
CPC ......... *A61N 5/0622* (2013.01); *A61N 5/0603* (2013.01); *A61N 2005/0607* (2013.01); *A61N 2005/067* (2013.01); *A61N 2005/0626* (2013.01); *A61N 2005/0647* (2013.01); *A61N 2005/0651* (2013.01); *A61N 2005/0659* (2013.01); *A61N 2005/0662* (2013.01); *A61N 2005/0663* (2013.01)

(58) Field of Classification Search
None
See application file for complete search history.

(56) References Cited

U.S. PATENT DOCUMENTS

| 8,308,784 B2 * | 11/2012 | Streeter | A61N 5/0618 128/898 |
| 2006/0287695 A1 * | 12/2006 | DiMauro | A61N 5/0603 607/88 |
| 2014/0088668 A1 | 3/2014 | Kim et al. | |

OTHER PUBLICATIONS

Choi, Richin, "International Search Report", International Application No. PCT/IB2015/059041, dated Feb. 9, 2016, 3 pages.
Choi, Richin, "Written Opinion", International Application No. PCT/IB2015/059041, dated Feb. 9, 2016, 4 pages.

* cited by examiner

*Primary Examiner* — Carl H Layno
*Assistant Examiner* — Dacheng Xie

(57) ABSTRACT

The present invention is a portable non-invasive system, apparatus and method for performing light therapy or photobiomodulation upon the brain tissues through the skull and/or nostrils of a living mammalian subject for the medical purpose of stimulating the brain in-vivo. The present invention utilizes the transcranial and/or intranasal pathways as points of anatomic access and follows established principles for the conceptual approach that irradiation of the brain tissue with low level light energy of certain fixed parameters would achieve major therapeutic effects in-vivo.

15 Claims, 28 Drawing Sheets

Fig. 14
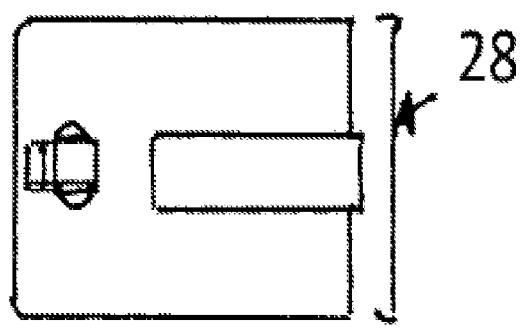
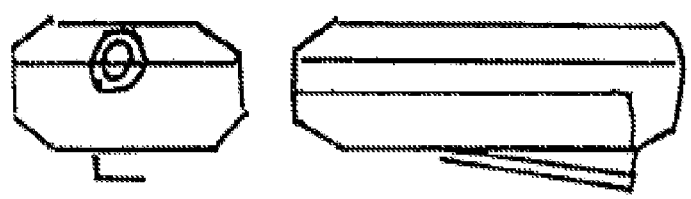
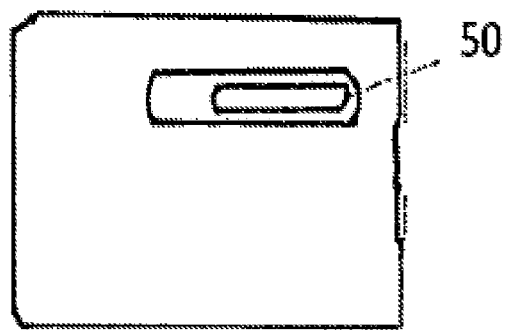

Intracellular mechanism of action of low level light therapy

Source: Rojas, JC, Gonzalez-Lima. Low-level light therapy of the eye and brain. 2011:3:49-67 (modified)

METHOD, SYSTEM AND APPARATUS FOR NON-INVASIVE NEUROSTIMULATION THERAPY OF THE BRAIN

FIELD OF THE INVENTION

The present invention relates to a method, system and apparatus for neurostimulation therapy, and more specifically, to a method, system and apparatus for intranasal and/or transcranial neurostimulation therapy of the brain.

BACKGROUND OF THE INVENTION

Many critics of the pharmaceutical industry are of the view that there is a shortage of effective medications for many chronic neurologic conditions. These conditions may include traumatic brain injury (TBI), stroke, multiple sclerosis (MS), schizophrenia, autism, insomnia, post-traumatic stress disorder (PTSD), dementia and Alzheimer's disease (Alzheimer's), Parkinson's disease (Parkinson's) and numerous other neurological conditions and disorders. Some are of the view that the available medications for psychiatry are either no better than placebos or could even be harmful. As a result, many patients with neurological conditions seek alternative therapies.

One field of alternative therapy, brain stimulation techniques, have been used some time, based on the fact that the neural system has responded to these techniques in substantive ways. Many of these techniques are based on electrical and magnetic impulses. The following listing constitutes the major methods currently used to stimulate the human brain for therapeutic purposes.

1. Electroconvulsive Therapy (ECT)

Electroconvulsive therapy (ECT) is one of the oldest methods used to electrically induce seizure in anesthetized patients in order to treat difficult cases of severe depression, mania and catatonia (see for example, Rudorfer, M V, Henry, M E, Sackeim, H A (2003). "Electroconvulsive therapy". In Tasman A, Kay J, Lieberman J A (eds) Psychiatry, Second Edition. Chichester: John Wiley & Sons Ltd, 1865-1901). The mechanism of action of the ECT method is not fully understood, and there is no general consensus on the treatment protocol. Furthermore, the ECT method carries the risk of damaging the brain, such injury being represented by cognitive deficits (see for example, Breggin P (2007). "ECT Damages the Brain: Disturbing News for Patients and Shock Doctors Alike". Ethical Human Psychology and Psychiatry. 9(2): 83-86). In addition, the consequent loss in IQ and memory from the therapy is also significant (see Andre L (2009). "Doctors of Deception: What They Don't Want You to Know About Shock Treatment". Rutgers University Press).

2. Cranial Electrotherapy Stimulation (CES)

Another electrical brain stimulation technique involves cranial electrotherapy stimulation ("CES"). The CES method applies a small pulsed electric current across the patient's head. Some medical practitioners claim that CES helps with conditions such as stress, anxiety, depression and insomnia. However, it is still an experimental technique (see for example, Klawansky S (1995). "Meta-Analysis of Randomized Controlled Trials of Cranial Electrostimulation: Efficacy in Treating Selected Psychological and Physiological Constitutions". Journal of Nervous & Mental Disease 183(7):478-484). The proposed mechanism of action for CES is that the pulses of electric current increase the ability of the neural cells to produce serotonin, dopamine, DHEA, endorphins and other neurotransmitters that stabilize the neurohormonal systems (see Gilula M F, Kirsch D L (2005). "Cranial Electrotherapy Stimulation Review: A Safer Alternative to Psychopharmaceuticals in the Treatment of Depression". Journal of Neurotherapy. 9(2)). Some believe that CES may help relieve certain stress-related symptoms but it has not been studied sufficiently to determine whether its use is practical and cost-effective (see Barrett S (2008). "Dubious Claims Made for NutriPax and Cranial Electrotherapy Stimulation". QuackWatch online, accessed on May 2012).

3. Deep Brain Stimulation (DBS)

Deep brain stimulation (DBS) utilizes implants which function by delivering measured doses of electrical stimulation via a thin electrode surgically inserted through a small hole in a patient's skull, with its tip implanted in a targeted brain area. The U.S. Food and Drug Administration (FDA) approved DBS devices and procedures for treatment of a disorder called "essential tremor" in 1997; for treatment of Parkinson's disease in 2002; and for treatment of dystonia in 2003 (see Kringelbach M L, Jenkinson N, Owen S L F, Aziz T Z (2007). "Translational principles of deep brain stimulation". Nature Reviews Neuroscience. 8:623-635). More recently, Alzheimer's Disease reportedly also responds to DBS (see Wood J (2012). "Brain Pacemaker Shows Promise in Fighting Alzheimer's Disease". PSychCentral.com online (May 12, 2012)). Despite their success, DBS treatments can be overactive in its effects, leading to an outcome which can trigger dizziness, tingling, and other undesirable side effects. Researchers also still do not understand how DBS treatment actually works in-vivo.

4. Transcranial Light Therapy (TLT)

Transcranial light therapy ("TLT") or transcranial photobiomodulation ("tPBM") is enjoying attention in recent years due to sound scientific principles, successful outcomes, lack of side-effects and being non-invasive. This method involves directing light to the brain through the outside of the skull. The source of light can be light emitting diodes (LED) or a low level laser source, usually in the red or near infrared-red (NIR) part of the spectrum. The NIR band would be the preferred choice in order to provide deeper penetration through the meninges, cranial material and then through the brain matter, in order to reach the deeper parts of the brain. Recent research supports transcranial light therapy's potential for treating stroke, traumatic brain injury, Parkinson's disease, mild cognitive impairment, Alzheimer's disease, depression, and some other cognitive issues (see for example, Rojas J C, Gonzalez-Lima F (2011). "Low-level light therapy of the eye and brain". Eye and Brain. 3:49-67). More recently, it has also been found that this modality can also enhance cortical metabolic capacity and retention of extinction memories, reduce fear renewal, and implicate low level light therapy as a novel intervention to improve memory (Rojas J C et al (2012). "Low-level light therapy improves cortical metabolic capacity and memory retention". J Alzheimer's Dis. 2012; 32(3): 741-52).

5. Ear Canal Transcranial Light Therapy

Ear canal transcranial light therapy was developed following a study in Finland that demonstrated that when bright light is directed into the ears, it helps to treat seasonal affective disorder (SAD) or winter depression (Timonen M et al (2012). "Can transcranial brain-targeted bright light treatment via ear canals be effective in relieving symptoms in seasonal affective disorder?" Medical Hypothesis. 78(4): 511-515). The commercially sold device has diodes in the form of ear buds with very bright white LED attached by cables to a controller unit. It is consumer-friendly and appears effective for SAD.

6. Optogenetic Neurostimulation

In the optogenetic neurostimulation (optogenetics) process, researchers first introduce a gene for a light-sensitive molecule, called channelrhodopsin 2 (ChR2), into a specific subset of neurons. Shining blue light on these neurons then causes them to fire. One advantage of this approach is its specificity, i.e., only the neurons with the gene are activated. This process also provides a way to shut neurons off, by introducing a different molecule, halorhodopsin ("NpHR"), which uses the energy of yellow light to silence the cells. The combination of these elements makes the technique very exact in achieving specific neuro-outcomes. Research with optogenetics can lead to important understandings in relating anatomical locations of the brain with predictable behavioral outcomes. The exactness of how behavior can be manipulated has great appeal in advancing neuroscience. However, at this time, the challenge is to translate animal experiments to human applications. The technique is still very much in the laboratory domain, involving small animals (mainly rats and mice). It is an invasive method involving implanting a light probe inserted into the brain, and connecting from the targeted brain area to a controller unit via a catheter holding an optic fiber. To achieve precise stimulatory outcomes, it also requires the introduction of ChR2 into the specific areas of the brain to have the desired neurons fire. The precision of the optogenetics method is highly appealing to scientists, but it is expected to stay in the research laboratory domain for the foreseeable future. Today, over 500 laboratories are applying optogenetic tools to animal models of Parkinson's, blindness, spinal injury, depression, narcolepsy, addiction, and memory (see Williams M (2010). "A brain implant that uses light". Technology Review online article published on Feb. 24, 2010).

7. Intranasal Light Therapy

Intranasal light therapy involves directing light energy through the nasal cavity and into the brain. Researchers have found that Intranasal Light Therapy provides positive outcomes with neurologic conditions such as insomnia, mild cognitive impairment, Alzheimer's disease, Parkinson's disease, schizophrenia, migraine and headaches, and stroke (cerebral infarction) in humans.

Summary of Current Brain Stimulation Techniques:

There is good data supporting the efficacy of all these conventionally known methods, thereby confirming that the brain responds to light, and brings about therapeutic outcomes in various forms. However, they are all very different ways of stimulating the brain for therapeutic purposes. Most treatment methods are either deployed in laboratory conditions on animals; or if deployed on human beings, largely have to be administered under clinical supervision. The optogenetics method understandably has attracted a great amount of attention in neuroscience circles because of the exactness in which it can extract neural outcomes through precise anatomical manipulation of the brain. However, the invasiveness and set-up required keeps it in the laboratory domain. One conventional method to date that has significant potential to become a consumer-friendly product, the ear canal transcranial method, is employed solely and specifically for treating seasonal affective disorder.

The methodology that seems to have great potential to treat a wide range of medical conditions is the transcranial method. For over a decade, transcranial photobiomodulation (PBM) has produced positive effects in laboratory animals and human subjects. Animal studies included acute traumatic brain injury (TBI), Alzheimer's, depression and stroke, while human studies, included TBI, depression and stroke. Furthermore, low level light energy has been found to be safe for humans in the stroke studies, without the side effects often associated with medications.

However, transcranial devices have yet to be developed to the point where they are portable and mass produced at a low cost. Instead, such devices are mainly available only in research labs because they are expensive to manufacture, have power requirements that do not allow them to be portable, and require training to use. Furthermore, such transcranial devices are designed such that the light energy is unlikely to reach important primal regions that are located on the underside of the brain. Amongst other functions, these primal regions govern memory, behavior and emotions.

Intranasal light therapy can be used to reach some of these regions located on the underside of the brain because they are closer to the nasal region than the scalp. Delivering light energy through the nasal cavity has the additional advantage in that the subject's scalp or hair do not act as barriers. However, light energy from an intranasal source are less likely to reach areas of the brain distal from the nasal cavity, such as the dorsal cortical areas around the top of the head.

Scientific Basis and Evidence for Brain Irradiation Therapy:

Because of the ineffectiveness of drugs in addressing many neurological disorders, increasing attention is being directed to alternative treatments, such as light therapy. Various research studies clearly show and factually evidence a variety of beneficial in-vivo effects of low-level light therapy (LLLT) on the brain. In animal research studies, low-level light therapy has been found to be promising for treating anoxic brain injury, atherothrombotic stroke, embolic stroke, Parkinson's Disease, mild cognitive impairment and Alzheimer's Disease. Similarly, in human studies, low-level light therapy has been found to be promising for improving on the effects of ischemic stroke, traumatic brain injury, depression and functions of the prefrontal cortex.

Mechanism of Action for Brain Irradiation Therapy:

FIG. 17 shows one intracellular mechanism of low level light therapy. As illustrated, one key to the therapeutic response of the brain lies in the presence of a photoacceptor respiratory enzyme which exists in all cellular mitochondria, cytochrome oxidase. The cytochrome oxidase enzyme represents the best known intraneural marker of metabolic activity; and its enzyme activity is tightly coupled with free radical metabolism, cell death pathway, and glutamatergic (a neurotransmitter related) activation, important for learning and memory (see for example, Wong-Riley M T (1989). "Cytochrome oxidase: an endogenous metabolic marker for neural activity". Trends Neurosc. 12(3):94-101).

Photoacceptors, unlike photoreceptors found inside the eyes, do not process light energy, but are instead a component part of the normal metabolic pathways. Photoacceptors are sensitive to light in the visible red region and near-infrared region of the light spectrum, and are able to convert the absorbed light of these red and near-infrared wavelengths into cellular energy molecules of adenosine triphosphate (ATP). When light of these visible red and near-infrared wavelengths (at low energy levels) enter living cells (including nerve cells), the light energy modulates the cell's activity of metabolism (photobiomodulation) by regulating internal mitochondrial function, the intraneuronal signaling systems, and the redox states. Moreover, empirical experiments show that photoneurobiomodulation of electrical activity in neurons can be achieved independently of thermal effects (see Fork R L (1971). "Laser stimulation of nerve cells in Aplysia". Science. 171(974):907-908). Also, when employed and delivered at low energy levels, the therapeutic effects of brain-absorbed light energy are not accompanied by any substantive complications or major side effects. Thus, with the neurons of the brain affecting virtually all functions and activities of the living body, the impact of exposing the brain to modulating light energy consequently affects the entire medical condition of the human being.

At the cellular level, the sensitivity of cytochrome oxidase to red light and near infrared red light may be explained by the role of the chromophore in the protein structure. The chromophore is an organic structural entity that is present in all photoreceptors, such as those present in the eyes and which give us the perception of colors. These chromophores will absorb only particular light wavelengths and reject all others; and the cytochrome oxidase in the chromophores are known to accept red and near-infrared red light energy.

These underlying facts accurately identify the potential impact of light energy irradiation that could be purposely directed into one or more anatomic parts of the living brain on-demand, resulting in both beneficial therapy for and prophylaxis against a variety of medically recognized nervous disorders and pathological states.

Photoacceptors in the Nervous System:

Although earlier-reported animal experiments suggested the presence of photoacceptors in the brain, it was only those particular experiments and empirical results first reported in 2000 which correctly demonstrated that isolated mitochondria are sensitive to irradiation with monochromatic light in the red and near-infrared red regions of the light spectrum. Thus, it was empirically demonstrated that illumination of isolated rat liver mitochondria with red low-powered lasers increased ATP synthesis and oxygen consumption (Karu T (2000). "Mechanism of low-power laser light action on cellular level". Proc SPIE. 2000; 4159:1-17). In addition, it has been empirically demonstrated that impaired mitochondrial oxidative metabolism is associated with neurodegeneration (see Wong-Riley M T et al (2001). "Light emitting diode treatment reverses the effect of TTX on cytochrome oxidase in neurons". Neuroreport. 12(14):3033-3037). Also, research studies revealed that rat neuronal cultures exposed to low level red light showed increases in cytochrome oxidase activity (see Wong-Riley M T et al (2005). "Photobiomodulation directly benefits primary neurons functionally inactivated by toxins: role of cytochrome c oxidase". J Biol Chem. 280(6):4761-4771).

Accordingly, a light-modulating method, system and apparatus aimed at improving mitochondrial metabolism in-vivo would be of major benefit to the functionality of both the diseased and normal brain tissues. Such a light-modulating methodology is also believed to potentially relieve pain in humans (see Chow R t et al (2009). "Efficacy of low-level laser therapy in the management of neck pain: a systematic review and meta-analysis of randomised placebo or active treatment controlled trials". Lancet. 374(9705): 1897-1908).

It is also noteworthy that the effects of light irradiation on the brain are observed to be effective in a wavelength-specific range. The primary photoacceptor mediating the effects of the light is not only localized to the mitochondria; the molecules that absorb the light in cells are believed to be part of the respiratory chain (see Karu T (1989). "Laser biostimulation: a photobiological phenomenon". J Photochem Photobiol B. 3(4):638-640).

Equilibrium and Homeostasis:

It is recognized that there comes a point when the photoacceptors (such as cytochrome oxidase) do not respond to further photostimulation. This critical event occurs when the photoacceptors are fully reduced or fully oxidized by the absorbed light energy; thus, photoacceptors can respond to light energy exposure only when they are in their intermediate stage (see Karu T I, et al (2008). "Absorption measurements of cell monolayers relevant to mechanisms of laser phototherapy: reduction or oxidation of cytochrome c oxidase under laser radiation at 632.8 nm". Photomed Laser Surg. 26(6):593-599). Accordingly, when the photoacceptors become fully reduced or are fully oxidized, further sequential low power irradiation will not yield further metabolic activity from the photoacceptors. This indicates that the living cells in the body have coded action potential limits when they are ex-homeostasis; and thus, the neurons of the brain have the potential to respond positively to light irradiation only until they reach a state of homeostasis.

Neural Conditions Suitable for Light Irradiation Treatment:

There are many potential neural conditions that can benefit from light irradiation of one or more regions of the brain in-vivo. Some of these medical conditions are summarily described below. In addition, it will be noted and appreciated that a wide range of other neural diseases, disorders, and pathological states are also envisioned to be effectively therapeutically treatable using the present invention. Examples of these other neural conditions are expected to include, but not limited to epilepsy, migraine, chronic fatigue syndrome, encephalitis, multiple sclerosis, anxiety disorder, attention deficit disorder, schizophrenia, and learning disabilities.

1. Treatment of Stroke, Neurotrauma, Cognition and an Emotional Mind State

Human and animal studies that relate to treatment of stroke, neurotrauma, cognition, emotional states, and similar neurological disorders are well documented (see for example, Rojas J C, Gonzalez-Lima F. "Low level light therapy of the eye and brain". Eye and Brain. 2011; 3:49-67). The brain, being the neurological control center of systemic body health, has a direct impact on all body health. For example, the health of the hypothalamus, being the key regulating gland for systemic homeostasis, has a profound impact on overall body health; and thus, a functionally improved hypothalamus will concomitantly yield a greater degree of systemic homeostasis. Also, research studies have extensively investigated brain irradiation for both stroke and neurotrauma. For example, recent studies by Uozemi et al. have demonstrated that low energy light delivered transcranially was able to increase blood flow by 30% (Uozumi Y et al (2010). "Targeted increase in cerebral blood flow by transcranial near-infrared laser irradiation". Lasers SurgMed. 42(6):566-576). Such demonstrated beneficial results with light irradiation have been accompanied with significant increases in nitric oxide production, a mechanism that is associated with the relaxation of vascular walls to achieve improved blood circulation. Thus, the cerebral blood flow was shown to be increased in both treated and untreated hemispheres. Also, subjects pretreated with light irradiation showed improved blood flow during the period of occlusion, with stable body temperature, heart rate and respiratory rates. The overall result is a significant decrease in apoptotic cells during a stroke event.

Regular irradiation with low level near infrared red (NIR) light has also been found to be associated with significant neurological recovery after stroke events (see Detaboada L et al (2006). "Transcranial application of low-energy laser irradiation improves neurological deficits in rats following acute stroke". Lasers Surg Med. 38(1):70-73). Furthermore, these recovery effects were associated with increased neuronal proliferation and migration in the subventricular zone, which plays a role in neurogenesis (see Oron et al (2006). "Low-level laser therapy applied transcranially to rats after induction of stroke significantly reduces long-term neurological deficits". Stroke. 37(10):2620-2624; see also Lampl Y et al (2007). "Infrared laser therapy for ischemic stroke: a new treatment strategy: results of the NeuroThera Effectiveness and Safety Trial-1(NEST-1)". Stroke. 38(6):1843-1849).

2. Treatment of Traumatic Brain Injury

Published research studies have provided in-vivo evidence that the effects of low level light irradiation on cytochrome oxidase and the release of nitric oxide plays a major role in the neuroprotective action of light irradiation therapy not just against ischemia, but also against traumatic brain injury (see Naeser M A et al (2010). "Improved cognitive function after transcranial, light-emitting diode treatments in chronic, traumatic brain injury: two case reports". Photomed Laser Sur. 29(5):351-358).

3. Treatment of Neurodegenerative Diseases

Light irradiation of the brain has been found to support neurogeneration in-vivo. Thus, light energy irradiation can therapeutically treat a range of different neurodegenerative diseases and disorders, such as Parkinson's disease which is specific to the substantia nigra, a part of the mid-brain area located behind the hypothalamus; and which can be reached with NIR light wavelengths. In a study using small animals like mice, it was demonstrated that low level light irradiation at 670 nm wavelength helps prevent the loss of dopaminergic cells in the substantia nigra (see Shaw V E et al (2010). "Neuroprotection of midbrain dopaminergic cells in MPTP-treated mice after near-infrared light treatment". J Comp Neurol. 518(1):25-40). However, longer wavelengths of light energy (such as near-infrared light (NIR)) are considered to be more feasible for much larger mammalian subjects such as a human being.

4. Treatment of Depression and Similar Emotional Deficits

Phenotypic expressions of mood disorders such as depression and post-traumatic stress disorder (PTSD) have been shown to be associated with decreased metabolic capacity in the prefrontal cortex region (see Shumake J, Gonzalez-Lima F (2003). "Brain systems underlying susceptibility to helplessness and depression". Behav Cogn Neurosci Rev. 2(3): 198-221). Electrical stimulation of the prefrontal cortex has been shown to have antidepressant effects (Hamani C et al (2010). "Antidepressant-like effects of medial prefrontal cortex deep brain stimulation in rats". Biol Psychiatry. 67(2):117-124). Thus, light irradiation of the prefrontal cortex region with red light and near-infrared red light may cause an increase of metabolic capacity in the prefrontal cortex region, as well as provide potential neuroprotection against these medical conditions. Indeed, a pilot study showed that when the foreheads of human patients suffering from major depression and anxiety were irradiated with low level light of 810 nm wavelength, the blood flow to the frontal cortex increased and induced a 63% reduction in depression scores (see Schiffer F (2009). "Psychological benefits 2 and 4 weeks after a single treatment with near infrared light to the forehead: a pilot study of 10 patients with major depression and anxiety". Behav Brain Funct. 5:46).

5. Treatment of Memory Deficits

Research studies have demonstrated that irradiation of the prefrontal cortex region of the brain with near-infrared red light of 1072 nm wavelength improved an individual's functional memory (see Mikhalikova S et al (2008). "Emotional responses and memory performance of middle-age CD1 mice in a 3D maze: effects of low infrared light". Neurobiol Learn Mem. 89(4):480-488). As this memory deficit condition is common among the more elderly, using light irradiation methods to treat the prefrontal cortex region of the brain can help with the aging-related problem of working memory deficits.

6. Treatment of Dementia and Alzheimer's Disease

Neurodegeneration can lead to cognitive impairment that is often medically identified with dementia. Causing an improved blood flow has therapeutic potential for addressing and treating vascular dementia. Alzheimer's disease, although medically a form of dementia, apparently has a variety of different causes. The early signs/symptoms of this neurodegenerative condition are typically revealed as regional brain metabolic deficits in the form of reduced cytochrome oxidase activity, an overt sign for potential risk of Alzheimer's disease (see Valla J et al (2001). "Energy hypometabolism in posterior cingulated cortex of Alzheimer's patients: superficial laminar cytochrome oxidase associated with disease duration". J Neurosci. 21(13):4923-4930). Because brain irradiation with red and infrared red light energy demonstrably activates cytochrome oxidase, a light irradiation treatment procedure can help manage the symptomatic onset of a full Alzheimer's disease state.

Animal studies demonstrate that the delivery of near infrared (NIR) light energy could improve the condition of a cognitive impaired brain associated with Alzheimer's disease (AD). Studies have found that low level light therapy (LLLT) improves cortical metabolic capacity and memory retention in mice. It is believed that the ability of LLLT to increase mitochondrial energy metabolism could be utilized to recover brain processes impacted by regional brain hypometabolism associated with AD (see Rojas J C, Bruchey A K and Gonzalez-Lima F (2012). Low-level Light Therapy Improves Cortical Metabolic Capacity and Memory Retention. Jnl. Alzheimer's Disease. 32(3): 741-52).

A further study using two transgenic mouse models suggests that NIR light may have the potential as an effective, minimally-invasive intervention for mitigating, and even reversing, progressive cerebral degenerations associated with dementia and AD. Their results suggest that significant reversal of AD pathology has been induced by NIR treatment (see Porushothuman S, Johnstone D M, Nandasena C, Mitrofinas J and Stone J (2014). Photobiomodulation with near infrared light mitigates Alzheimer's disease-related pathology in cerebral cortex, evidence from two transgenic mouse models. Alzheimer's Research & Therapy. 6:2).

It has also been proposed that LLLT that can be directed to proliferate mesenchymal stem cells (MSC). This can ameliorate the progression of AD as demonstrated in a mouse model (see Farfara D, Tuby H, Trudler D, Doron-Mandel E, Maltz L, Vassar R J, Frenkel D and Oron U (2015). Low-level Laser Therapy Ameliorates Disease Progression in a Mouse Model of Alzheimer's Disease. J Mol Neurosc. 55: 430-436).

Further, it has been proposed that intranasal light therapy can enhance the activity of the SIRT1 enzyme activity (see Liu T C Y, Wu D E, Gu Z Q and Wu M (2010). Applications of Intranasal Low Intensity Laser Therapy in Sports Medicine. Jnl. Innovative Optical Health Sc. 3(1): 1-16), and this activity helps in the differentiation of mesenchymal stem cells (see Joe I S, Jong S G and Cho G W (2015) Resveratrol-induced SIRT1 activation promotes neuronal differentiation of human bone marrow mesenchymal stem cells. Neurosci Lett. January 1; 584: 97-102).

The histological activities underlying the reaction of AD and demented brains to LLLT can be explained by the observations of several published investigations. In 2002, it was demonstrated that weak light could be used to guide the direction taken by the leading edge or growth cones of a nerve cell. In actively extended growth cones, a laser spot is placed in front of a specific area of a nerve's leading edge, enhancing growth into the beam focus and resulting in guided neuronal turns as well as enhanced growth (see Erlicher A, Betz T, Stuhtmann, Koch D, Milner V and Raizen J (2002). Guiding neuronal growth with light. PNAS 99(22): 16024-16028). This phenomenon was repeated in another experiment in 2013 (see Black B, Mondal A, Kim Y and Mohanty S K (2013). Neuronal Beacon. Optical Society of America Optics Letter. 38(13): 2174-2176). Nerve cells appear to have an innate attraction to low energy light forces.

Researchers have also found that cells repair themselves when exposed to red low level light, as seen in FIG. 18. FIG. 18 shows a neurite elongation experiment with in vitro post-oxidative stress (670 nm, 3 mW, 20 sec/day, 5 days). Neurites of neurons that were shortened by oxidative stress would re-elongate. The data suggest that red light irradiation protects the viability of cells in the case of oxidative stress. It also stimulates neurite outgrowth (see Giuliani A, Lorenzini L, Gallamini M, Masella A, Giardino L and Calza L (2009). Low infrared laser light irradiation on cultured neural cells: effects on mitochondria and cell viability after oxidative stress. BMC Com Alt Med. 9:8). As such, there is a basis to believe that if low level red and NIR light energy can be delivered to neurons that are functioning sub-optimally, a healing response is possible.

The Default Mode Network (DMN):

The Default Mode Network (DMN) of the brain has attracted interest because it has been associated with Alzheimer's disease, dementia, autism, schizophrenia, depression, chronic pain, Parkinson's disease, multiple sclerosis (MS) and post-traumatic stress disorder (PTSD). The DMN is active when individuals are engaged in internally focused tasks including memory retrieval, envisioning the future, and conceiving the perspective of others (see Buckner R L, Andrews-Hanna J R and Schacter D L (2008). The Brain's Default Network: Anatomy, Function, and Relevance to Disease. Ann. N.Y. Acad. Sci. 1124:1-38).

Regarding brain disorders, researchers have discovered targeted nexuses in the DMN, referred to as the "cortical hubs". As shown in FIG. 19, the cortical hubs comprise: (i) the dorsal medial prefrontal cortex 502; (ii) the ventral medial prefrontal cortex 504; (iii) the hippocampus and entorhinal cortex 506; (iv) the precuneus 508; (v) the lateral parietal lobe 510; and (vi) the posterior cingulate cortex 512. These hubs are highly connected in the DMN, although some of them may lie outside the network. Buckner et al suggested that cortical hubs interconnect distinct, functionally specialized systems. Through positron emission tomography amyloid imaging these hubs showed high amyloid-β deposition in the locations consistent with the possibility that hubs, while acting as critical way stations for information processing, may also augment the pathological cascade in AD (Buckner R L, Sepulcre, Talukar T, Krienen F M, Liu H, Hedden T, Andrews-Hanna J R, Sperling R A and Johnson K A (2009). Cortical Hubs Revealed by Intrinsic Functional Connectivity: Mapping, Assessment of Stability, and Relation to Alzheimer's Disease. J. Neurosci. 29(6): 1860-1873).

Experiments have shown that Aβ deposition in Alzheimer's disease occurs preferentially in the locations of cortical hubs (see Stam C J (2014). Modern Network science of neurological disorders. Neuroscience 15:683).

Another important brain network may be the Salience Network (SN). Neurodegenerative illnesses such as Alzheimer's and Parkinson's target the DMN, whereas behavioral variant disorders such as frontotemporal dementia (FTD) target the more anterior-located SN. While the DMN is identified with the whole brain, the SN emphasizes the anterior of the brain which is anchored by the anterior insula and the anterior cingulate cortex. While it appears that the DMN and SN may be different from each other, they are connected to each other in many activities. The SN plays an important role in driving the switches between the DMN and the central executive networks. These networks are thought to be heavily involved in handling novel situations outside the domain of some of our 'automatic' psychological processes.

Neurological Disorders Associated with Lesions in Cortical Hubs:

It has been proposed that lesions in the cortical hubs are associated with the at least the following brain disorders: schizophrenia, Alzheimer's disease, frontotemporal dementia, Parkinson's disease, temporal lobe epilepsy, Gilles de la Tourette syndrome, acute brain injury (coma), and migraine. Ischemia and oxidative stress are identified with these lesions.

Photobiomodulation (PBM) can potentially stimulate these lesions in the cortical hubs to heal. As mentioned above, it has been shown that weak light attracts the leading edge of growth cones of a nerve cell. When a beam of light is positioned in front of a specific area of a nerve's leading edge, this draws its growth towards the direction of the light, as well as enhances its overall growth. Nerve cells appear to "feed" on low energy light. As shown in FIG. 18, researchers also found that cells repair themselves when they are exposed to low energy red light. The neurites of neurons that were shortened by oxidative stress would re-elongate. The data suggests that red light irradiation protects the viability of cells and stimulates neurite outgrowth in cases of oxidative stress. In the specific case of Alzheimer's-related lesions, transgenic mice with Alzheimer's recovered memory function and cognition function with transcranial PBM. An autopsy on the brains of these mice revealed a reduction of the lesions associated with the biomarkers, Aβ plaques and neurofibrillary tangles.

SUMMARY OF THE INVENTION

The invention concerns a novel systems, apparatus and method to stimulate therapeutic outcomes by irradiating the various parts brain with light—i.e., neurostimulation. This is anatomically achieved by: (i) applying a headset comprising one or more light generating units to the patient's head (transcranial neurostimulation); and/or (ii) inserting a small clear plastic-encapsulated light generating unit through the nasal cavity (intranasal neurostimulation). Both the transcranial and intranasal light generating units are controlled by a control assembly unit, and are powered by a replenishable dry cell battery. There is no invasion into the body tissue.

The irradiating light may be untargeted (i.e., broadly directed to stimulate the general brain area) or be purposefully targeted at specific regions of the brain in order to achieve particular therapeutic outcomes. The coverage area and depth of light stimulation is influenced by selecting the appropriate wavelength of light, its direction, the effective energy output, exposure time, and the coherency (as relates to a laser source). The neurostimulation system and apparatus is small and is hands-free, allowing for full mobility and portability for the user; and offers a new and easy method to stimulate the brain for therapeutic purposes. The parameters may be controlled with a small control unit, or with a smart-phone having the appropriate downloaded application software.

In one aspect, the present invention provides a self-administrable system for performing non-invasive neurostimulation therapy of the brain of a living mammal on-demand, said self-administrable non-invasive neurostimulation system comprising:

first, second, third and fourth configured irradiation units, each of said first, second, third and fourth configured irradiation units comprising a portable hollow casing having fixed dimensions, a sized internal spatial volume and an external surface configuration suitable for application to the skull, said portable hollow casing of each configured irradiation unit being comprised of:
(i) a light energy transmitting material which forms at least a portion of the configured external surface for said hollow casing of each configured irradiation unit; and
(ii) at least one light generating unit housed and contained within said internal spatial volume of said hollow casing of each configured irradiation unit and which is capable of generating light energy of at least one preselected wavelength selected from the group consisting of near infrared red light wavelengths and visible red light wavelengths, at a predetermined energy intensity and for a preset time duration on-demand sufficient to penetrate through the skull and to pass into the brain, whereby said first, second, third and fourth configured irradiation units can emit light energy after application to the skull and achieve passage of said emitted light energy through the skull into at least one portion of the brain in-vivo;

a frame adapted for support of said first, second, third and fourth configured irradiation units and for at will placement of said light transmitting external surface of said first, second, third and fourth configured irradiation units at a fixed position and desired irradiation direction on the skull;

a portable controller assembly able to control on-demand delivery of light energy from said configured irradiation units into at least one portion of the brain in-vivo, said controller assembly including:
(a) a portable and replenishable power source of on-demand direct electrical current,
(b) a central processing unit for controlling and directing the flow of such direct electrical current,
(c) at least one connector in electrical communication with the power source for on-demand conveyance of direct electrical current to the central processing unit, and
(d) at least one connector in electrical communication with the configured irradiation units for on-demand conveyance of direct electrical current from said central processing unit to said light generating units;

wherein:
(A) said first configured irradiation unit is positioned to direct light energy to a first region of the brain comprising the left and right ventral mesial prefrontal cortex areas, and optionally, the anterior cingulate gyrus areas;
(B) said second configured irradiation unit is positioned to direct light energy to a second region of the brain comprising the left and right precuneus cortical areas, and optionally, the posterior cingulate gyrus areas;
(C) said third configured irradiation unit is positioned to direct light energy to a third region of the brain comprising the left angular gyrus area in the lateral, inferior parietal cortex, and optionally, the left posterior cingulate gyrus; and
(D) said fourth configured irradiation unit is positioned to direct light energy to a fourth region of the brain comprising the right angular gyrus area in the lateral, inferior parietal cortex, and optionally, the right posterior cingulate gyrus.

In another aspect, the present invention provides a self-administrable dedicated apparatus for performing non-invasive neurostimulation therapy of the brain of a living mammal on-demand, said self-administrable dedicated apparatus comprising:

first, second, third and fourth configured irradiation units, each of said first, second, third and fourth configured irradiation units comprising a portable hollow casing having fixed dimensions, a sized internal spatial volume and an external surface configuration suitable for application to the skull, said portable hollow casing of each configured irradiation unit being comprised of:
(i) a light energy transmitting material which forms at least a portion of the configured external surface for said hollow casing of each configured irradiation unit; and
(ii) at least one light generating unit housed and contained within said internal spatial volume of said hollow casing of each configured irradiation unit and which is capable of generating light energy of at least one preselected wavelength selected from the group consisting of near infrared red light wavelengths and visible red light wavelengths, at a predetermined energy intensity and for a preset time duration on-demand sufficient to penetrate through the skull and to pass into the brain, whereby said first, second, third and fourth configured irradiation units can emit light energy after application to the skull and achieve passage of said emitted light energy through the skull into at least one portion of the brain in-vivo;

a frame adapted for support of said first, second, third and fourth configured irradiation units and for at will placement of said light transmitting external surface of said first, second, third and fourth configured irradiation units at a fixed position and desired irradiation direction on the skull;

a portable controller assembly able to control on-demand delivery of light energy from said configured irradiation units into at least one portion of the brain in-vivo, said controller assembly including:
(a) a portable and replenishable power source of on-demand direct electrical current,
(b) a central processing unit for controlling and directing the flow of such direct electrical current,
(c) at least one connector in electrical communication with the power source for on-demand conveyance of direct electrical current to the central processing unit, and
(d) at least one connector in electrical communication with the configured irradiation units for on-demand conveyance of direct electrical current from said central processing unit to said light generating units;

wherein:
(A) said first configured irradiation unit is positioned to direct light energy to a first region of the brain comprising the left and right ventral mesial prefrontal cortex areas, and optionally, the anterior cingulate gyrus areas;

(B) said second configured irradiation unit is positioned to direct light energy to a second region of the brain comprising the left and right precuneus cortical areas, and optionally, the posterior cingulate gyrus areas;

(C) said third configured irradiation unit is positioned to direct light energy to a third region of the brain comprising the left angular gyrus area in the lateral, inferior parietal cortex, and optionally, the left posterior cingulate gyrus; and (D) said fourth configured irradiation unit is positioned to direct light energy to a fourth region of the brain comprising the right angular gyrus area in the lateral, inferior parietal cortex, and optionally, the right posterior cingulate gyrus.

In another aspect, the present invention provides a self-administrable method for performing non-invasive neurostimulation therapy of the brain via a nasal cavity and through the skull of a living mammalian on-demand, said self-administrable non-invasive neurostimulation method comprising the steps of:

obtaining a light energy-emitting apparatus comprised of:
first, second, third and fourth configured irradiation units, each of said first, second, third and fourth configured irradiation units comprising a portable hollow casing having fixed dimensions, a sized internal spatial volume and an external surface configuration suitable for application to the skull, said portable hollow casing of each configured irradiation unit being comprised of:
  (i) a light energy transmitting material which forms at least a portion of the configured external surface for said hollow casing of each configured irradiation unit; and
  (ii) at least one light generating unit housed and contained within said internal spatial volume of said hollow casing of each configured irradiation unit and which is capable of generating light energy of at least one preselected wavelength selected from the group consisting of near infrared red light wavelengths and visible red light wavelengths, at a predetermined energy intensity and for a preset time duration on-demand sufficient to penetrate through the skull and to pass into the brain, whereby said first, second, third and fourth configured irradiation units can emit light energy after application to the skull and achieve passage of said emitted light energy through the skull into at least one portion of the brain in-vivo;

a frame adapted for support of said first, second, third and fourth configured irradiation units and for at will placement of said light transmitting external surface of said first, second, third and fourth configured irradiation units at a fixed position and desired irradiation direction on the skull;

a portable controller assembly able to control on-demand delivery of light energy from said configured irradiation units into at least one portion of the brain in-vivo, said controller assembly including:
  (a) a portable and replenishable power source of on-demand direct electrical current,
  (b) a central processing unit for controlling and directing the flow of such direct electrical current,
  (c) at least one connector in electrical communication with the power source for on-demand conveyance of direct electrical current to the central processing unit, and
  (d) at least one connector in electrical communication with the configured irradiation units for on-demand conveyance of direct electrical current from said central processing unit to said light generating units;

placing a transparent external surface of said first, second, third and fourth configured irradiation units at a desired fixed position adjacent to the skull of a subject such that light energy emitted by said first, second, third and fourth configured irradiation units will penetrate through the subject's skull and pass into at least one portion of the brain in-vivo; and causing said light generating units of said positioned configured irradiation units to generate light energy of at least one preselected wavelength selected from the group consisting of near infrared red light wavelengths and visible red light wavelengths, at a predetermined energy intensity and for a preset time duration on-demand sufficient to penetrate through the subject's skull and to pass into the brain such that neurostimulation of at least one portion of the brain is achieved;

wherein:

(A) said first configured irradiation unit is positioned to direct light energy to a first region of the brain comprising the left and right ventral mesial prefrontal cortex areas, and optionally, the anterior cingulate gyrus areas;

(B) said second configured irradiation unit is positioned to direct light energy to a second region of the brain comprising the left and right precuneus cortical areas, and optionally, the posterior cingulate gyrus areas;

(C) said third configured irradiation unit is positioned to direct light energy to a third region of the brain comprising the left angular gyrus area in the lateral, inferior parietal cortex, and optionally, the left posterior cingulate gyrus; and (D) said fourth configured irradiation unit is positioned to direct light energy to a fourth region of the brain comprising the right angular gyrus area in the lateral, inferior parietal cortex, and optionally, the right posterior cingulate gyrus.

Preferably, said system and/or apparatus further comprises:

a configured irradiation lens including:
  a portable hollow casing having fixed dimensions, a sized internal spatial volume, and an external surface configuration suitable for in-vivo insertion into the nasal cavity space of a nostril without causing substantial impairment to the subject's ability to breathe and without invading the nasal tissues of the living subject, said portable casing of said configured irradiation lens being comprised of:
    (i) a light energy transmitting material which forms at least a portion of the configured external surface for said hollow casing of said configured irradiation lens,
    (ii) at least one light generating unit housed and contained within said internal spatial volume of said hollow casing of said configured irradiation lens and which is capable of generating light energy of at least one preselected wavelength selected from the group consisting of near infrared red light wavelengths and visible red light wavelengths, at a predetermined energy intensity and for a preset time duration on-demand sufficient to penetrate through the nasal tissues and to pass into the brain, whereby said configured irradiation lens can emit light energy in any desired direction within the nasal cavity after in-vivo insertion and achieve passage of said emitted light energy from the nasal cavity into at least one portion of the brain in-vivo;

a self-administrable applicator means adapted for support of said configured irradiation lens and for at will placement of said light transmitting external surface of said configured irradiation lens at a fixed position and desired irradiation direction within a nostril adjacent to the internal lining of a subject's nasal cavity;

wherein said portable controller assembly is further able to control on-demand delivery of light energy from said configured irradiation lens.

Thus, the present invention provides a novel device that comprehensively directs therapeutic light energy into the brain from a combination of transcranial (through the skull) and intranasal (via the nasal channels) locations.

BRIEF DESCRIPTION OF THE DRAWINGS

The present invention may be easily understood and more readily appreciated when taken in conjunction with the accompanying drawings, in which:

FIG. 1 illustrates the concept on how light from the system irradiates the brain in general, with little tissue barrier in between;

FIGS. 14a, 14b, 14c and 14d illustrate the external form factor for the controller assembly;

DETAILED DESCRIPTION OF THE PREFERRED EMBODIMENTS

Figure 1:
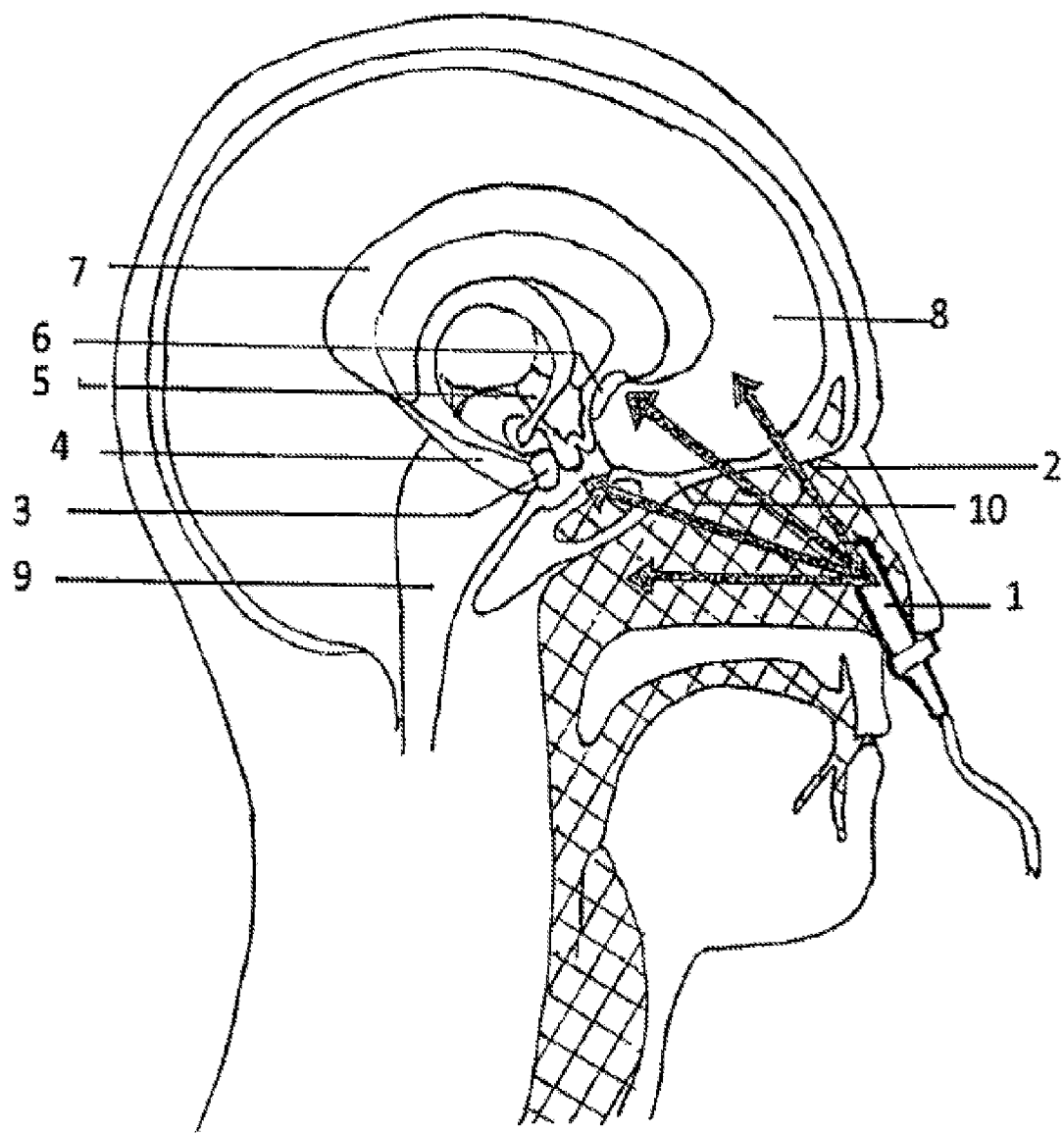

The present invention is a portable non-invasive system, apparatus and method for performing irradiation light therapy upon the brain tissues through: (i) the skull; and/or (ii) the nostrils of a living mammalian subject for the medical purpose of stimulating the brain in-vivo. Conventionally today, there exist several known ways of stimulating the brain, but these techniques largely involve research experiments on laboratory animals or are procedures which need to be clinically/medically supervised.

In marked difference to these conventionally known therapeutic procedures, the present invention utilizes the transcranial and/or intranasal pathways as points of anatomic access and follows established principles for the conceptual approach that irradiation of the brain tissue with light energy of certain fixed parameters would achieve therapeutic effects in-vivo. In this manner, the present invention utilizes light energy of specified intensity, wavelengths, coherency, duration and pulsed mode to achieve therapeutic outcomes.

The system, apparatus and method of the invention preferably delivers therapeutic light irradiation through the skull to specific cortical hubs of the brain's DMN. For this purpose, the light energy-emitting apparatus comprises at least one configured irradiation unit including a portable hollow casing having fixed dimensions, a sized internal spatial volume, and an external surface configuration suitable for application to the skull. The system and apparatus are designed such that light energy is delivered through the skull using a headset that is easy to apply to the subject's head and comfortable to wear for an extended period of time. The headset preferably comprises a frame to support each configured irradiation unit. Each configured irradiation unit is preferably positioned within the frame such that, when the headset is worn by the subject, light energy is directed to specific cortical hubs of the brain.

The system, apparatus and method of the invention also preferably delivers the therapeutic light irradiation to the brain through the tissues lying adjacent to the nasal cavity. For this purpose, the light energy-emitting apparatus comprises a configured irradiation lens including a portable hollow casing having fixed dimensions, a sized internal spatial volume, and an external surface configuration suitable for in-vivo insertion into the nasal cavity space of a nostril. The nasal insertion apparatus components are designed to be small and comfortable; and to avoid causing significant or meaningful impairment in the user's ability to breathe. After insertion, the apparatus may be adjusted or preset to: direct the irradiating angle of the release of the light emitted from the apparatus, set the desired power levels, generate a pulsed frequency for the emitted light, and choose the time duration for the treatment session in order to achieve the intended therapeutic effects.

The instant invention preferably provides a number of outcomes, including but not limited to:

The treatment system, apparatus and method utilize principles and apply operational parameters that are factually supported and evidenced by published scientific research.

There are no known major side effects or complications associated with this treatment method and system.

The apparatus is medically non-invasive and self-administrable in each and every embodiment and instance of use.

The apparatus is dedicated to and designed for at will self-attachment to and self-detachment from the subject's skull and nose.

The apparatus is extremely light in weight, portable, and is easily transported by hand over any distance.

The apparatus is comfortable and easy to use, and in particular, is more comfortable that a full helmet used in current transcranial therapies.

The apparatus is to be self-administered on-demand routinely and repetitiously by the patient himself or herself for therapeutic treatment, and does not require any assistance by a medical technician or physician.

The apparatus can alternatively employ either lasers or light emitting diodes as light generating units.

The apparatus can generate light energy waves and particles at any desired medically effective wavelength(s) chosen from the near-infrared and red light ranges.

The apparatus causes no significant electromagnetic or other interference with other medical devices, and thus is suitable for use by persons having an implanted pacemaker or defibrillator.

The power and battery requirements are specific to the light source which may be lasers or non-laser light emitting diodes.

Preferred embodiments may deliver pulsed light where this has been tested to support more therapeutic benefits for certain medical conditions.

Preferred embodiments of the apparatus are simple to use by any person in that one merely uses his or her hands to place the headset onto his or her skull and/or clip the applicator onto a nostril and presses the "power on" button.

Preferred embodiments of the apparatus include both a timer and an automatic shut-off switch which self-engages after 20 to 25 minutes or other lengths of time.

Preferred treatment duration is medically relevant; and the actual treatment time may vary depending on the choice of light source and targeted fluent (or dosage).

Preferred embodiments of the apparatus are highly resistant to accidental injury, and are able to withstand a drop of 5 feet without incurring any damage.

Preferred embodiments of the apparatus employ a process controller assembly which ensures that the light energy delivered to the skull or the nasal cavity is consistent. If the battery is unable to sustain a consistent power to drive the circuit to power the light source, the process controller assembly will give a warning and will switch off the device.

Alternative embodiments include the use of "smart phones" with downloaded software applications that perform in lieu of the process control assembly.

Targeted Areas of the Brain:

Specific anatomical parts of the brain govern specific functions of the mind and body. For example, the diencephalon (roughly around the mid-brain) region is the seat of some of the most essential survival functions, and holds some keys to the physical well-being of the person. This is a hard-to-reach region for access by a light source.

Among the anatomical brain components here, the hypothalamus is the control center for many autonomic functions. It is connected with the structures of the endocrine and parasympathetic nervous systems to support its vital role in maintaining homeostasis throughout the body. It is part of the limbic system that influences various emotional and pleasure responses, storing memories, regulating hormones, sensory perception, motor function, and olfaction. The other components of the limbic system are the amygdala, cingulated gyrus, hippocampus, olfactory cortex and the thalamus.

Whilst the mid-brain area could be a primary target, the divergent light rays will also illuminate some of the other parts of the brain to achieve a wider-spread benefit. The hypothesis of how the therapy is distributed, throughout the brain as the next stage into the secondary areas, is also based on the ability of the neural system to carry signals rapidly in its network.

The light energy may be manipulated to point towards targeted parts of the brain for more potency in specific primary areas. For example the substantia nigra (its dysfunction is attributable to Parkinson's disease) located at the bottom of the mid-brain area; or in another case, the prefrontal cortex in a separate location could be targeted to improve higher order cognitive functions and balance out primal emotions.

System/Apparatus/Method Specifications and Dosimetry:

An effective and safe light irradiation method and system in compliance with the present invention provides choices and control over certain operational parameters. These operational parameters include the choice(s) of: the light wavelength, coherency or non-coherency, energy (as measured in Joules (J)), Power (as measured in Watts (W) or milliwatts (mW)), irradiance (W/cm$^2$), radiant exposure (J/cm$^2$), exposure time (seconds), wave type (continuous or pulsed), fraction protocol (number of patient treatment sessions), light beam size (area of landed beam), and light beam penetration (delivery) distance.

1. Choice of Therapeutic Wavelengths

The wavelengths shown to be most effective at inducing in vivo beneficial effects in living neural cells have been in the optical window of the red and near-infrared red range (NIR) of the spectrum (i.e., between 620 nm and 1400 nm wavelengths). Successful treatments for brain irradiation have typically been performed at 633-670 nm (visible red) wavelengths or 808-1072 nm (near-infrared) wavelengths in both animals and humans. Accordingly, any light wavelength ranging between about 620 nm and 1400 nm is deemed to be acceptable for therapeutic use with the present invention.

In general however, the longer the wavelength of light, the lower the energy required for successful treatment and it is well established that the longer the light wavelength, the deeper the penetration distance of the light passing into and through living tissues. In the present invention, the shorter visible red light wavelengths between about 600 nm-780 nm are able to perform as well as the near-infrared (NIR) wavelengths between about 780 nm-1400 nm for certain conditions. Researchers recognize that it is this range of wavelengths that draw the greatest cellular response as opposed to the need to have this wavelength merely for tissue penetration. When tested on rats, photons between 630 nm and 800 nm have been shown to penetrate up to 28 mm even in layers of tissues with relatively low transparencies such as skin, connective tissue, muscle, bone, and spinal cord (even though much is already dissipated after the initial 1 mm) with about 6% of the total energy density being detectable at the ventral surface. Deeper tissue penetration obviously offers a better head start, and hence the longer NIR should be considered.

Great importance is given to the fact that it is these wide ranges of light wavelength that may induce the greatest mitochondrial response, as opposed to the need to have one particular wavelength for effective tissue penetration distance in-vivo. Furthermore, light photons wavelengths between 630 nm and 800 nm will penetrate living tissues and travel up to 28 mm distance even through layers with relatively low transparencies such as skin, connective tissue, muscle, bone, and spinal cord—with about 6% of the total energy density being detectable. Therefore, should depth of penetration be a critical factor for the medical condition or pathological state being treated, the NIR light wavelengths between about 620 nm-1400 nm are preferred for use based on the fact that the longer wavelengths penetrate deeper into the tissues.

Note also that penetration of light energy through living tissues depends not only on the chosen wavelength but also on the optical properties of the targeted tissues. In particular, the maximal penetration distance of light energy within the gray and white matter of the brain occurs at wavelengths between about 620 nm-1400 nm in the NIR light region. For this reason also, the NIR light wavelengths between about 620 nm-1400 nm are highly preferred for use.

It is also generally preferable to select and use a single monochromatic wavelength of light for a single therapeutic application. Typically therefore, the single monochromatic wavelength chosen should be about 670 nm (visible red) or about 810 nm (near-infrared red). Moreover, simultaneous dichromatic irradiation changes the ratio of the reduced and oxidized form of the enzymes. Thus, it is recommended that the user select pure monochromatic wavelength light source for most therapeutic applications. As a guide to selecting specific therapeutic wavelengths of light, it is suggested that light wavelengths in the region of 633 to 670 nm be employed for general brain irradiation and that light wavelengths of about 808 to 1072 nm be used to penetrate and reach the deeper anatomic regions of the brain.

Previous investigations suggest that if one irradiates Alzheimer's disease brain cells with red light or low intensity light, he or she can improve the conditions of an Alzheimer's disease patient. Scientific facts support an improved set of parameters based on NIR for better results. A study also showed that transcranial light therapy using a 808 nm laser diode attenuated amyloid plaque development in the transgenic mouse model, implying the possible efficacy of this therapeutic method at around this wavelength for the all-important AD in humans.

2. Choice of Coherent vs Non-Coherent Radiation (lasers vs light-emitting diodes)

Lasers provide coherent electromagnetic radiation that is unidirectional, hence allowing for a more concentrated energy coupled with a high energy input. Also modern laser light sources are usually constructed in low intensity semiconductor formats, with a built-in divergence that allow for a high degree of safety (often about 57 degrees divergence). Such laser light sources have distinct advantages which include: (i) a higher degree of tissue penetration; (ii) an efficient optic coupling; and (iii) a high monochromaticity. When a deeper penetration distance of living tissues is required, given the same parameters of wavelength, energy dosage and intensity, the coherent light of lasers is often more desirable than the non-coherent light generated by light-emitting diodes (LEDs).

However, for most therapeutic applications, light coherency as such is not required for clinical efficacy, and in those medical circumstances where a greater distance of tissue penetration is needed, it is deemed better met using non-coherent light at longer wavelengths from light-emitting diodes (LEDs). In recent years, light-emitting diodes (LEDs) have become viable therapeutic alternatives to lasers as light sources. It is postulated that the cell's photoacceptors (particularly cytochrome oxidase) do not discern between the coherency or non-coherency of the light photons that are received. Therefore, given the same wavelength of light, the energy dosage and intensity input received at the cell's photoacceptor receptors using light-emitting diodes (LEDs) will yield therapeutic outcomes which are very similar or identical to that provided by coherent light of laser light sources. Although penetration with LED non-coherent light is typically shallower, the LED generated non-coherent light has the advantage of providing a wider area of irradiation beam coverage.

The system, apparatus and method of the present invention recognizes the coherent vs. non-coherent differences existing between light from laser sources and light-emitting diode sources, and provides for both possibilities by carefully choosing between them on the basis of the optimum condition for particular application purposes (i.e., the particular disease state or disorder to be therapeutically treated will dictate which is the better format).

Therefore as merely a first illustrative example, when there is an advantage in irradiating only one specified area in the mid-brain area, such as irradiating the more deeply located pineal gland in order to restore normal circadian rhythms and correct sleep disorders, the coherent light of the laser light source is generally preferred for its greater tissue penetration distance. As a meaningful alternative however, the use of non-coherent LED light at a longer wavelength (preferably in the NIR range) in combination with a longer treatment time will adequately compensate for the loss of maximal tissue penetration distance that can be provided by the coherent light of the laser source.

As a second illustrative example, whereas the coherent light from a NIR 810 nm laser source would be most favored because of its deeper tissue penetration capabilities, the 810 nm laser light itself is invisible to the human eye. Thus, the user of the present invention has no visible light as such to trigger eye blinking as an autonomic defense mechanism to accidental eye exposure and the user runs a substantial risk of inadvertently causing a major retinal injury to the eye if he or she is careless. Hence the present invention offers a guided approach which recommends that when the 810 nm light wavelength is employed and is intended for unsupervised personal therapeutic usage at home, such 810 nm light should preferably be made available to the purchasing public in the LED light source version. Similarly, the laser sources of the 810 nm light wavelength are preferably reserved and limited for therapeutic use solely within the research domain or in a supervised medical treatment environment. Alternatively, it is suggested that laser sources be used to generate visible red light at about the 655 nm wavelength in order to benefit from the safety aspect of having a visible red light, as well as concomitantly to provide the greater tissue penetrative advantages of laser light.

Another important aspect of non-coherent LED generated light is that the use of such non-coherent light creates a very negligible amount of heat in comparison to laser generated light. This valuable feature of non-coherent LED generated light allows the living brain tissue to be exposed for longer periods of time using wavelengths at relatively low power densities, which in turn allows for more efficacious modulation of neural metabolism. Thus, if the treatment time is to be prolonged for medical efficacy, as exemplified by the treatment of traumatic brain injury, non-coherent LED generated light wavelengths at relatively low power densities are preferred over the use of laser generated light in order to avoid the risk of causing undesired thermal injury to the brain tissue.

For general therapeutic use purposes therefore, the present invention preferably uses LED light sources and non-coherent light wavelengths (especially in the NIR wavelength range owing to its greater tissue penetrative quality) for therapy treatments as well as for preventive medicine applications. This preference generally includes and encompasses those medical/clinical/pathological conditions relating to human cognitive functions, neurodegeneration, vascular dementia, migraine, pain, and human memory deficits.

In comparison, given the same wavelengths, low power level coherent light from laser sources is preferable for treating acute and chronic neurological disorders and conditions, and is desirable for treating specifically targeted regions/areas which are more deeply anatomically located within the interior of the brain. Thus, visible red light irradiation treatment of Parkinson's disease (involving the substantia nigra), sleep disorders related to the circadian rhythm (pineal gland), and accelerated rehabilitation (hypothalamus) are preferably treated using low level coherent light from lasers when compared to LED of the same wavelength. Also for safety reasons, visible red light wavelengths between 620 nm to 780 nm are preferably used with minimal safety restrictions.

3. Therapeutic Energy and Other Parameters

Light energy is traditionally measured as Joules (J)=Power (W)×Time (seconds). For brain stimulation purposes, very little light energy is required to stimulate mitochondrial activity, although a definitive minimal threshold amount for medical efficacy is yet to be established as such. Instead, the proper reference point for medical efficacy in use today is the time-tested intravenous light irradiation technique involving light being directly injected into the vein (used mainly in Russia, Germany and many other countries around the world for decades), and which normally follow the parameters of lasers with a wavelength of 632.8 nm, a power of 1.5 mw, and a time of 30 minutes per treatment session. On this basis, patients are usually treated once a day for the first three calendar days, and then treated once every two calendar days, until a total of ten patient treatment sessions is reached. For each patient treatment session, light energy of 2.7 Joules (1.5/1000 W×30 minutes×60 seconds) is delivered.

When brain irradiation with laser generated light (identical or similar to the 632.8 nm wavelength) is applied in the present invention, there are adjacent tissue depth issues to consider. These issues are overcome by increasing the Power (measured in Watts (W) or milliwatts (mW)) by several orders of magnitude, such as 5 mw for 25 minutes, thereby generating an energy output of 7.5 Joules (5/1000 W×25 minutes—60 seconds). Also, adding greater Power to a pulsed light source delivers more energy, which in turn can activate more ATP in-situ; however, such added Power to the system compromises the usability of the methodology in the intranasal embodiment. A reference Power parameter for laser embodiments of the present invention is to limit the Power factor to 5 mw in order to keep the Power at the low risk level of Class 3R [a standard set by the US Food and Drug Authority (FDA)]. Thus, a preferred set of operational parameters for the laser embodiments would offer a Power factor of 5 mw and a time treatment duration limited to 25 minutes for each patient treatment session.

In comparison, it is noted that the LED light source is mostly divergent. Accordingly, when using the LED embodiments of the invention, the energy output is to be increased by about 60% to about 12 Joules. This change in energy output also calls for a higher Power factor now set at 8 mw (12 Joules/(25×60 seconds)×1000).

In summary therefore, for a laser light source, one preferred energy aimed for is about 7.5 Joules (5/1000 W×25×60 seconds) and for a LED light source, one preferred energy aimed for is about 12 Joules (8/1000 W×25×60 seconds).

4. Continuous Wave (CW) vs Pulsed Frequency

The published scientific literature has factually established that when using 808 nm laser light, pulsed laser beams at 100 Hz and 1000 Hz produce superior results to continuous wave (CW) beams at 100 Hz and 1000 Hz, and that a 810 nm laser beam pulsed at 10 Hz produced a greater clinical recovery from traumatic brain injury than a continuous wave beam at 100 Hz. Why pulsing at 10 Hz works better than 100 Hz (or any other frequency) remains and is a matter of speculation. It is noted that 10 Hz is the frequency of alpha brain waves and thus pulsation at 10 Hz resonates with the whole brain at rest. Furthermore, the hippocampus region of the brain also functions at waves in the 4-10 Hz range. The hippocampus is responsible for memory, emotional well-being, behavioral management, spatial memory and navigation. It also is one of the regions that suffer severe damage in advanced Alzheimer's disease.

Generally, under certain conditions, ultra-short pulses can penetrate deeper into the tissues than continuous wave (CW) irradiation because more power can used. Pulsing also prevents the undesirable thermal effect where heat is built up. Pushing greater power to a pulsed light source delivers more energy, which can activate more cellular energy (ATP), as demonstrated in a study on rabbits. Under pulsed mode, the effective dosage is higher than the conventional calculation due the deeper travel into the tissues. The other mechanism of action involves the first part of a pulse containing photons to take all chromophore molecules in the upper tissue layer to excited states, opening the way for more photons into the tissue during the next pulse. Using 808 nm lasers on rabbits, researchers demonstrated that pulsed lasers at 100 Hz and 1000 Hz produced superior results to continuous wave. Researchers testing with 810 nm laser also found that pulsing at 10 Hz produced even greater recovery from traumatic brain injury than 100 Hz. They suggested that the antidepressant activity of the light therapy was a contributing factor.

If light in a visible wavelength is used in the present invention, it may be preferable to avoid using a pulsing mode on humans due to a possible risk of photosensitive epilepsy events. For this reason, it may be preferable to use pulsed invisible near infrared light, such as light having a wavelength of about 810 nm, in the present invention. Furthermore, the direction of light through the scalp and nasal cavity reduces the risk of photosensitive epilepsy.

In summary, for brain therapy using the present invention, and particularly for treatments of the mid-brain region, a 10 Hz pulsed model is preferred for efficacious clinical outcomes, especially when combined with a NIR 810 mw light source, which gives good penetration depth.

Figure 25:
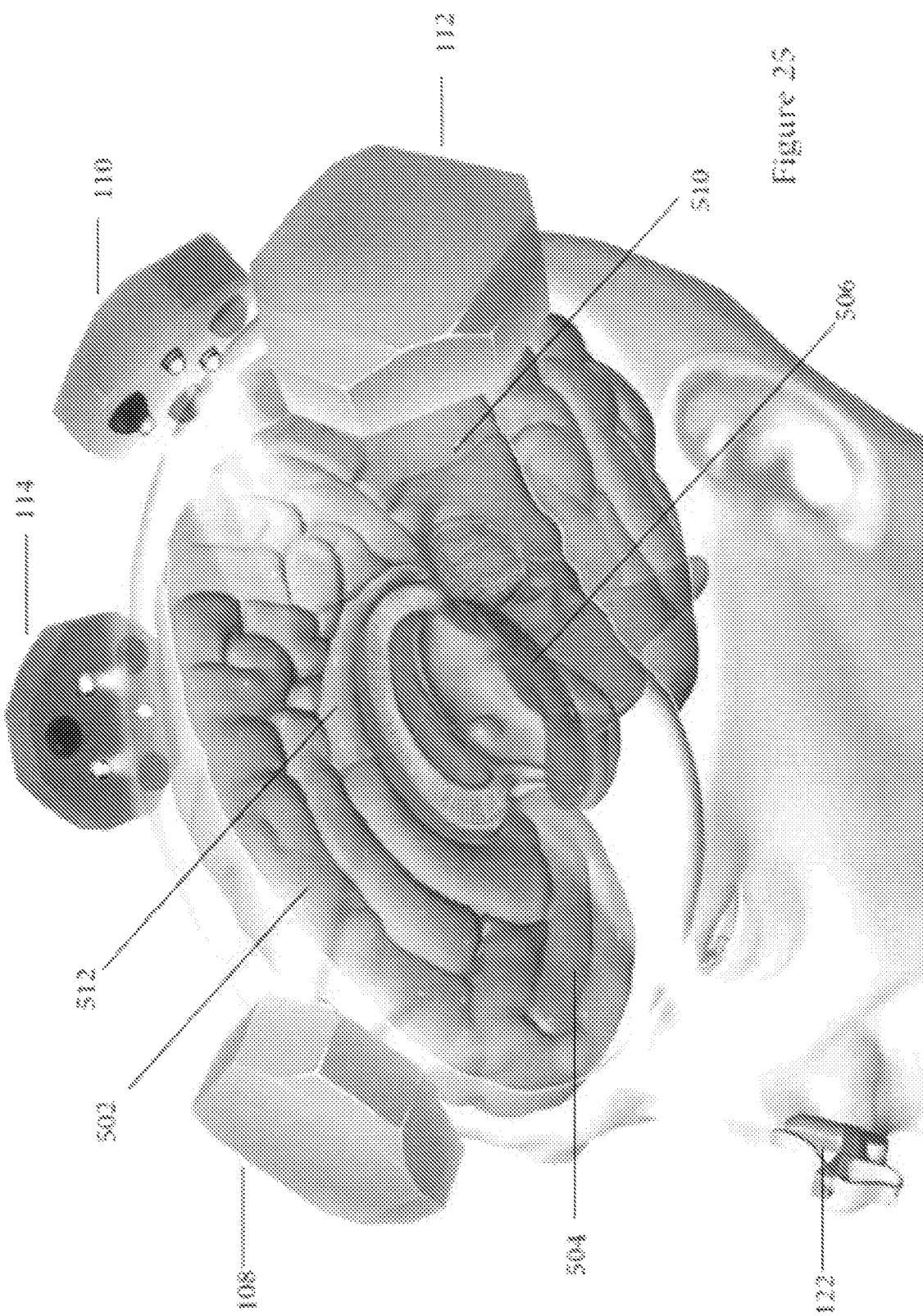
FIG. 25 illustrates a preferred embodiment of the apparatus of the present invention directing light energy to cortical hubs in the brain's Default Mode Network.

Targeted Transcranial Light Therapy of the Present Invention:

The present invention provides targeted treatment of cortical hubs of the DMN at specific locations, as can be seen in FIG. 25. Since the cortical hubs are highly connected with each other (sometimes labelled as "connectomes"), stimulating a few of these major hubs may stimulate the whole network in a holistic manner. This allows a lightweight, portable transcranial NIR light therapy device to be designed, pointing at a few select locations, instead of a less comfortable closed helmet commonly used in transcranial light therapy research.

An overriding design objective is to have a device that is as portable and easy to use, more akin to a stereo headset than a heavy helmet or a set of multiple lamps that are the common with transcranial light therapy devices. Specifically, as shown in FIGS. 20 to 24 and 29, the present invention provides a light frame which supports one or more cluster heads, wherein each cluster head houses one or more light generating units.

The present invention preferably targets the hippocampus and other locations on the ventral side of the forebrain because these anatomical regions are associated with AD. With this inclusion, the network of hubs related to AD is now even more comprehensive. A preferred set of targets for the present invention include but are not limited to the brain's precuneus, posterior cingulate cortex, medial prefrontal cortex, middle frontal lobe, hippocampus, parietal lobe and temporal lobe. These selected targets can lead to a comprehensive holistic therapeutic effect of the brain because the hubs are highly connected to each other.

Intranasal Light Therapy of the Present Invention:

A light source that is inserted into the nasal cavity will anatomically lie in close proximity (about 3 inches of mainly air cavity and soft tissue) to the mid-brain area. As shown in FIG. 1, when the light source 1 in this intranasal position is pointed towards the mid-brain area, little energy is required for effective light irradiation because much of the physical pathway distance to the brain tissue is the air cavity 2 of the nostril. For purposes of illustration, the mid-brain areas highlighted anatomically are: the amygdala 3, the hippocampus 4, the hypothalamus 5, the septal area 6, and the cingulated cortex 7. The portion of the neo-cortex region that is easily illuminated by the light source is the prefrontal cortex 8. Other than the area of the brain stem 9 which connects the spinal cord to the brain, the thinnest part of the protective skull is the thin perpendicular plate of the ethmoid bone 10. As historical testament to its low barrier resistance to the brain, the ethmoid bone 10 is also that part of the skull which is typically broken during the ancient Egyptian mummification process to drain out the brain materials. Granted, there is some tissue material present as part of the nasal septum wall in the pathway leading to the mid-brain region, but such tissue material is of low density.

Having little tissue material existing between the intranasally positioned light source and the targeted brain areas is notable because red light waves and infrared red light waves penetration (as defined by the Beer-Lambert law) can suffer optical power decay of up to 80% at 1 mm distances from the surface [see for example, Abdo A, Sahin M (2007). "NIR light penetration depth in the rat peripheral nerve and brain cortex". Conf Proc IEEE Eng Med Biol Soc 2007: 1723-1725]. Anatomically, the intranasal pathway of light irradiation mainly has the much thinner perpendicular plate of the ethmoid bone existing between the brain and the light source and there is little else of tissue consequence intervening over the distance, hence allowing more light energy penetration into the brain, given that all other operational parameters remain the same.

The anatomical advantages described above therefore allow for a therapeutic treatment system that employs a low energy diode with the appropriate light wavelength source pointing in the proper anatomic direction, as illustrated by FIG. 1. The control unit for managing the light generating source and light energy emissions can be miniaturized to allow for a portable and personal use system. This methodology and system has many distinct advantages over alternative modes of treatment currently available. It provides therapeutic effectiveness, a low energy demand, personal convenience, a self-administration capability, a very modest cost, and an exceptionally easy mode of use.

Components of the Apparatus:

The non-invasive system and apparatus of the present invention comprises the following four component parts:
  (i) a portable hollow casing;
  (ii) a discrete light generating unit which is housed and contained within the interior spatial volume of the hollow casing;
  (iii) an identifiable source of electrical current; and
  (iv) a processing and power controller assembly.

These four components are electrically linked together by at least one connector in electrical communication with the source of electrical current for on-demand transfer of direct electrical current to the controller assembly, and at least one connector in electrical communication with the controller assembly and the light generating unit for on-demand conveyance of direct electrical current from the controller assembly. Collectively, the components fulfill the aim of the invention to have the apparatus giving the user full mobility while delivering light of chosen specification to the desired areas of the brain, whether targeted or untargeted.

Preferred particulars of the structural details and attributes for each of the four component parts are illustrated by FIGS. 6-12 respectively, and a more detailed description of each requisite component part is presented below.

1. A Portable Hollow Casing

Each embodiment of the instant invention will include at least one portable hollow casing having fixed dimensions, a sized internal spatial volume and an external surface configuration suitable for application to the head and/or in-vivo insertion into the nasal cavity space of a nostril, without causing substantial impairment to the subject's ability to breathe.

Preferably, the portable casing may be constructed and formed of a light transmitting material over at least a portion of its external surface, and will encompass that volumetric zone intended for housing and containment of at least one light generating unit. By definition, such light transmitting material includes and encompasses transparent, translucent and opaque matter. However, in most instances, a completely clear and transparent matter is deemed best for use.

It is also important to note that the intended purposes and goals of the portable casing are twofold: (i) to serve as a containment chamber that is configured for easy application to the skull and/or in-vivo insertion into the nasal cavity space of a nostril; and (ii) to act as a molded lens that reflects and directs emitted light waves to the brain.

For intranasal light therapy in the present invention, the portable hollow casing must have dimensions which are small enough to allow insertion into one nostril, will minimize impairment of the subject's ability to breathe, and yet will be able to maximize the scattering of the light particles towards the walls of the subject's nasal cavity. For these reasons, it is very desirable that the hollow casing for intranasal therapy be fashioned in size and configuration for support by a tangible holder or fixture which the human subject can hold with his fingers. Thus, while the portable casing can be fashioned into any generally slender and elongated shape such as a tubular, or cigar-shaped, or cylindrical format, it is deemed both useful and appropriate that the overall configuration of the portable hollow casing also provide a structural means for support which allows its placement into a nasal cavity space at will. For this reason also, the "L" shaped format illustrated by FIG. 9 is very desirable and is considered to be an optimal configuration.

2. The Light Generating Unit(s)

Each light generating unit is capable of generating light energy of at least one preselected wavelength on-demand. It is intended that the light generating unit will be able to deliver therapeutic light at wavelengths that include the following: (i) in the visible color spectral ranges, the visible red light wavelengths ranging between about 620-780 nm; and (ii) in the non-visible spectral ranges, the near-infrared light wavelengths ranging between about 780-1400 nm.

In addition, the generated light energy waves and particles may alternatively be: (i) either coherent (as in lasers) or incoherent; (ii) be either pulsed or non-pulsed (continuous wave) in delivery; (iii) be either constant or non-constant in intensity; (iv) be either uniform or non-uniform in phase; (v) polarized and non-polarized; and (vi) have a regular or irregular flux.

Any conventionally known means for generating electromagnetic radiation or articles for propagating radiant energy are acceptable for use in the present apparatus. In the majority of embodiments, it is intended and expected that either a low level laser unit or a light emitting diode (LED) will be employed as the light generating unit(s) for irradiating purposes. Accordingly, the apparatus as a whole requires only a functional light generating unit or units; and it is of no consequence to the present invention what the nature, or construction, or format of the light generating unit might be so long as it generates and transmits light of at least one prechosen and therapeutically effective wavelength.

Therapeutically Useful Light Wavelengths:

The preferred embodiments would use light at visible red and near-infrared red ("NIR") wavelengths of the light spectrum (i.e., between about 620 nm to 1400 nm). This does not preclude the possibility of deploying light in other wavelengths from ultraviolet B (about 280 nm) to the visible red wavelength region (to 620 nm).

For completeness, if and when desired or needed, the entire spectrum of visible and invisible light wavelengths that can be provided by the one or more of the light generating unit(s) of the apparatus. The spectrum of visible and invisible light wavelengths that can be generated on demand by the apparatus if desired is identified by Table 1 below.

TABLE 1

| Visible and Near-Visible Colour Wavelength Ranges | |
|---|---|
| Ultraviolet A&B: | 280-400 nm |
| Violet: | 400-420 nm |
| Indigo: | 420-440 nm |
| Blue: | 440-490 nm |
| Green: | 490-570 nm |
| Yellow: | 570-585 nm |
| Orange: | 585-620 nm |
| Red: | 620-780 nm |
| Near-Infrared Red: | 780-1400 nm |

Therapeutically Effective Light Ranges and Wavelengths:

A guiding principle of the invention is to transmit and deliver a therapeutically efficacious energy for the neurosystem. For this purpose, it is generally preferred that at least coherent visible red light generated by a low level laser, or non-coherent visible red light generated by a LED, and is fixed at wavelengths ranging between 620-1400 nm be used. For these reasons, various preferred embodiments of the apparatus and system will transmit and direct either coherent or incoherent visible light energy at red color wavelengths ranging between 620-1400 nm, with a radiant power between 10 to 1000 mW. In comparison, some embodiments of the irradiation apparatus and system will emit and deliver visible light energy at wavelengths of between 490-570 nm with a radiant power of 10 to 1000 mW (the green color range). In the alternative, still other embodiments will emit visible light energy at wavelengths ranging between 400-490 nm (the blue color range) at a radiant power between 10 to 1000 mW.

A general principle about electromagnetic waves and penetration is that the longer the wavelength, the deeper the penetration. Based on this principle, it would be expected that far infrared light with its longer wavelengths would have superior penetration than red or near infrared light with its shorter wavelengths. However, the distance light can travel through tissue is dependent on both the wavelength and the optical properties of the target tissue. In the case of tissues of the central nervous systems, components such as blood and water play significant roles in determining the depth of penetration.

One especially preferred embodiment of the present invention uses light energy at wavelength of about 810 nm.

Figure 26:
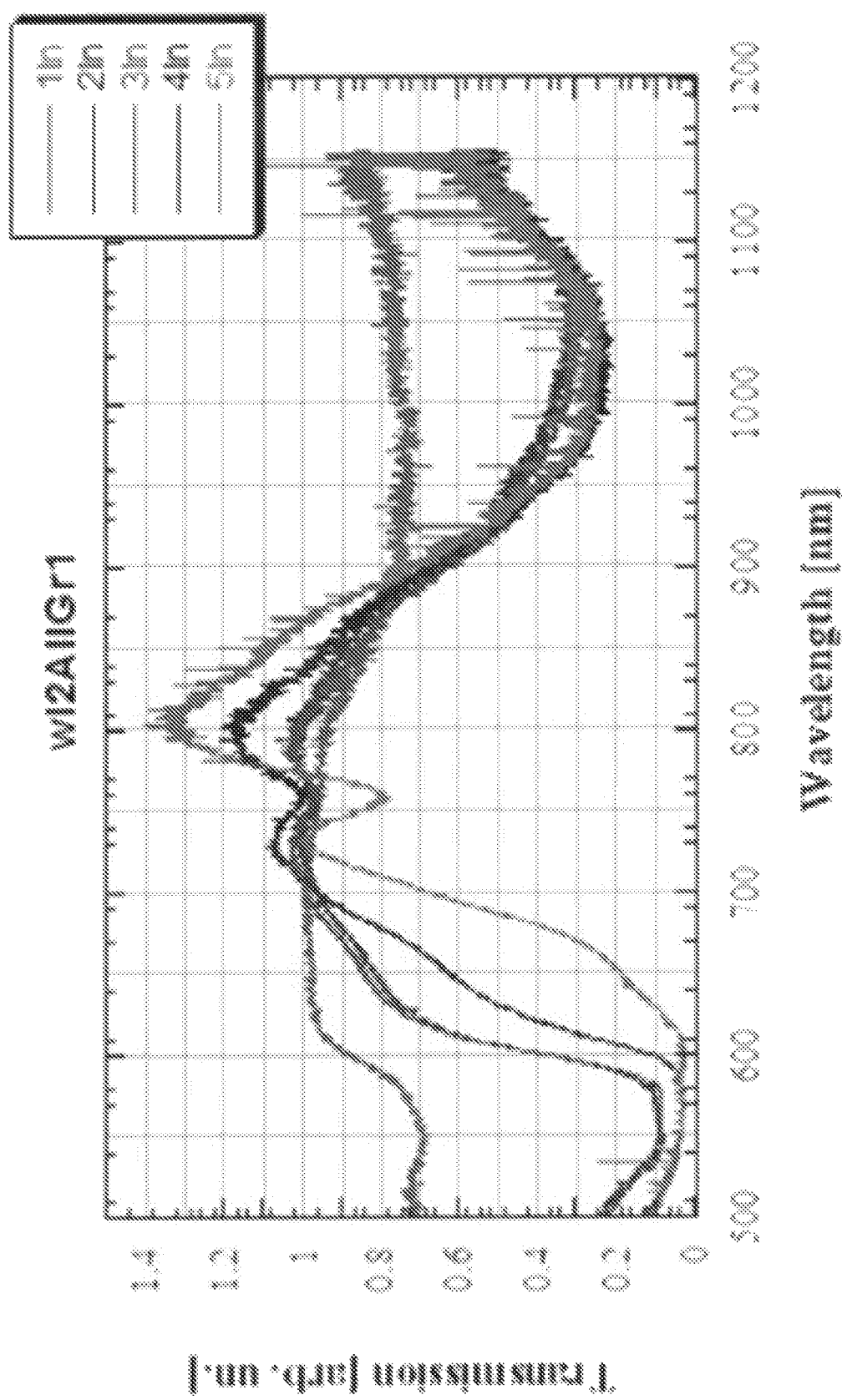
FIG. 26 is a graph illustrating the transmission of light having wavelengths between 500 nm and 1150 nm into tissues of the central nervous system.
Figure 27:
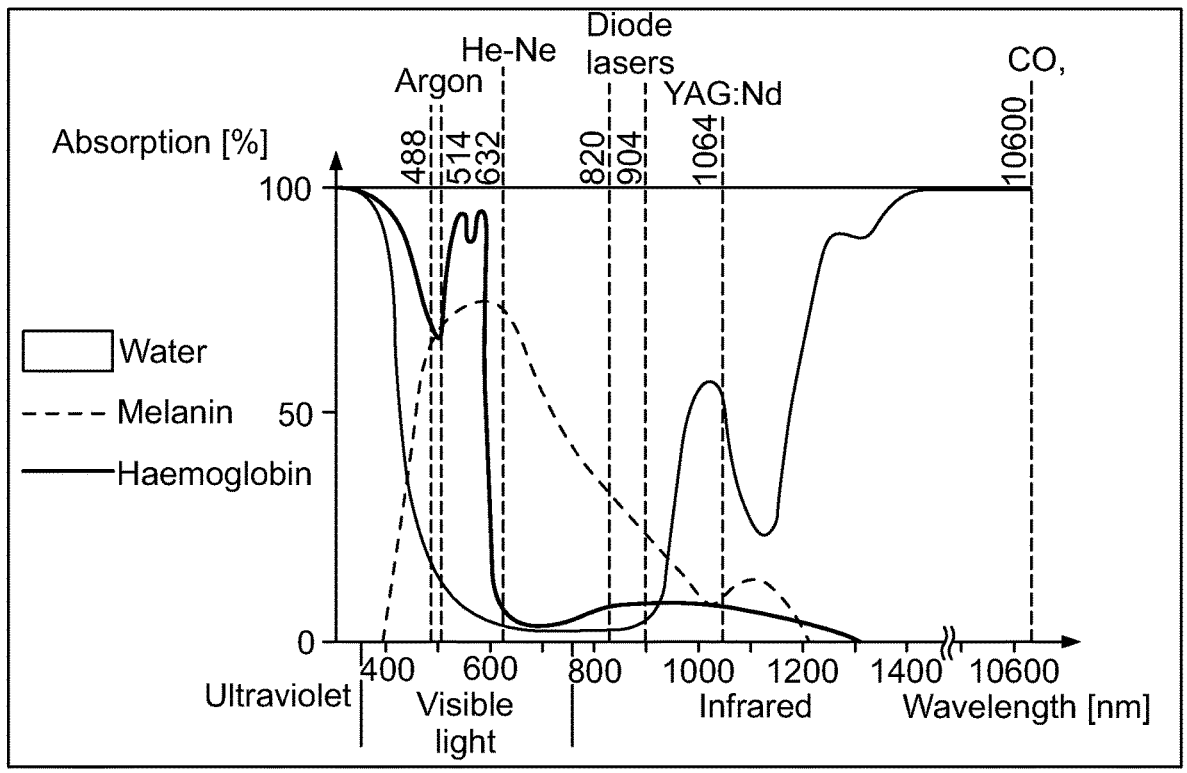
FIG. 27 is a graph illustrating absorptions percentages by water, melanin and haemoglobin for light of various wavelengths.
Figure 28:
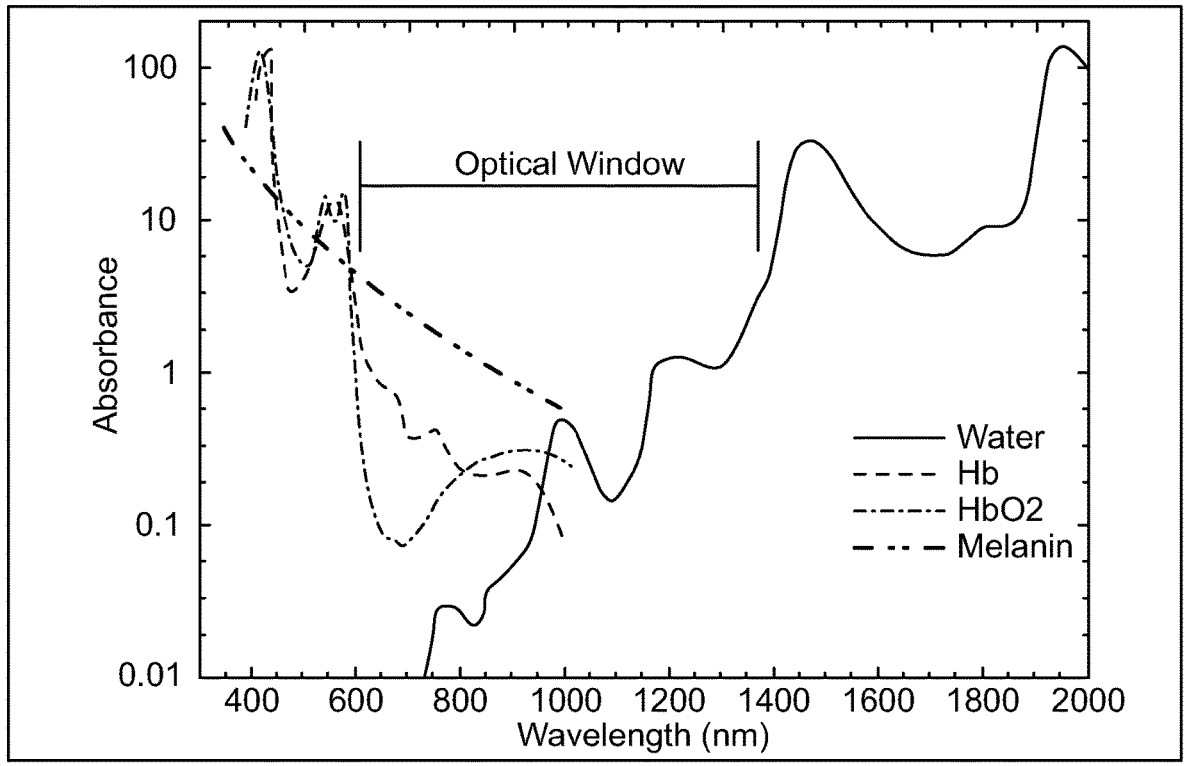
FIG. 28 is a graph illustrating the optical window in tissue due to reduced absorption of red and near infrared wavelengths (about 600 nm to 1200 nm) by tissue chromophores.

As shown in FIG. 26, wavelengths of about 810 nm penetrate deepest into the tissues of the central nervous system. Furthermore, as shown in FIGS. 27 and 28, light having wavelengths of about 810 nm are not adsorbed by blood (haemoglobin) and water to the same degree as light having other wavelengths.

3. A Source of Electric Current

It is required that a portable and replenishable source of on-demand direct electrical current exist as a component part of the apparatus and system of the present invention. The therapeutic treatment system and method provided by the instant invention is intended to deliver a specific energy dosage (measured in Joules), which is a function of power (in wattage) and time (in seconds), and which is deemed to be efficacious for each therapeutic treatment.

Figure 5:
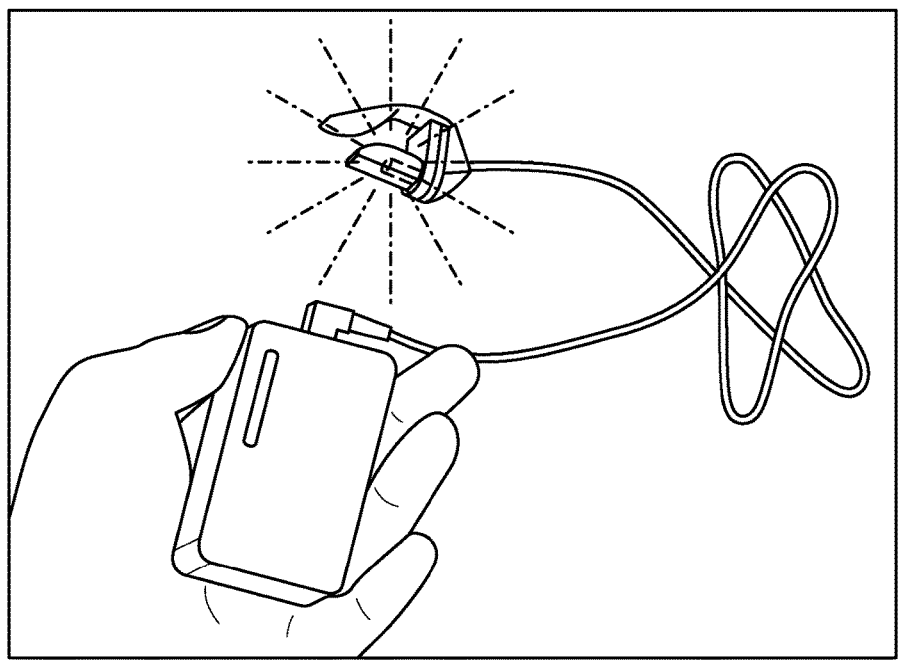
FIG. 5 is a photograph showing a preferred embodiment of the intranasal unit of the apparatus comprising the present invention.
Figure 6:
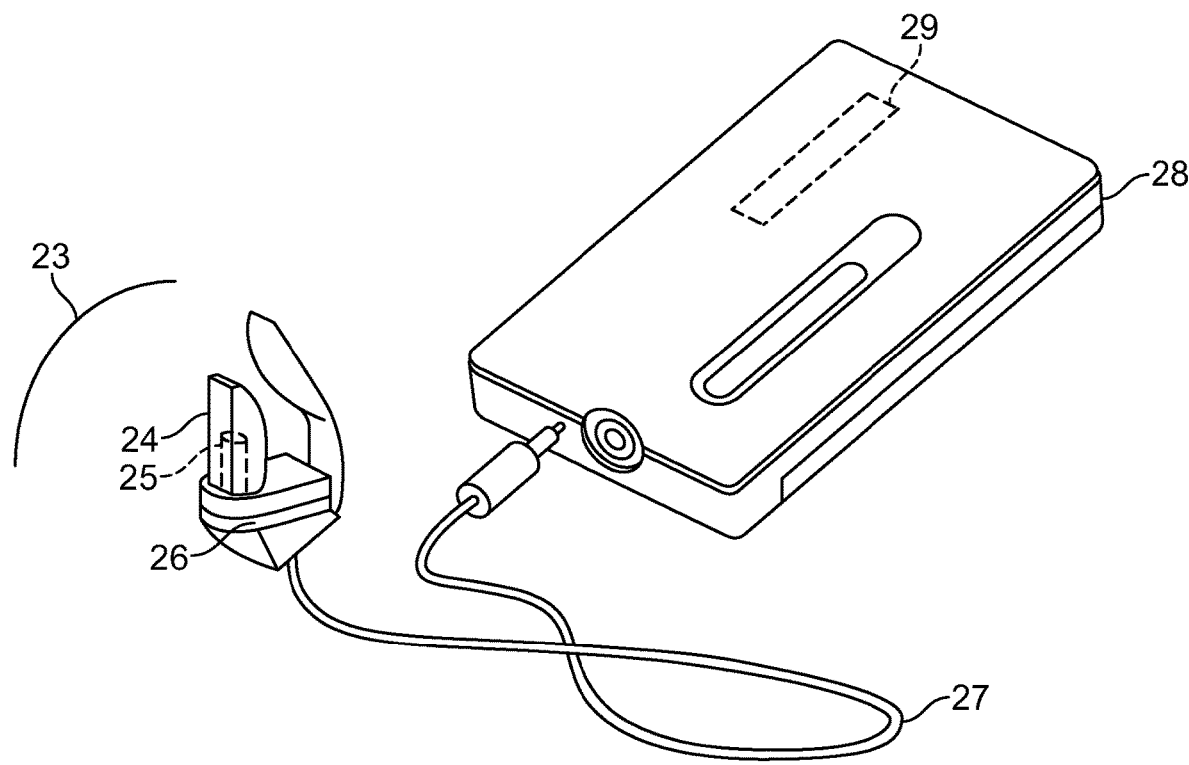
FIG. 6 shows a preferred embodiment of the intranasal unit of the apparatus comprising the present invention.

In the preferred embodiments shown by FIGS. 5 and 6 respectively, a 1.5 volt dry cell battery is employed to power the diodes for intranasal light therapy. The respective embedded programs will enable components to deliver intranasal therapeutic energy as follows:

(i) 11-12 Joules/cm$^2$ for the 633 nm LED embodiment;
(ii) 7-8 Joules/cm$^2$ for the 655 nm low level laser embodiment; and
(iii) 11-13 Joules/cm$^2$ for the 810 nm pulsed LED (before pulsed mode duty-cycle).

It is also expected and intended that there will be other alternative embodiments with different combinations of these components and which would require different configurations of power, energy dosage and treatment time.

The power supply typically will convey energy in the form of direct electric current. Adequate quantities of electric current can be repeatedly conveyed from either from a single battery source or from a combination of several dry cells joined together in series or parallel. In some other desirable embodiments, the source of electric power will be in the form of a rechargeable direct current battery unit (rechargeable from ordinary household alternating current receptacles) or as alternating current (AC) via a power adaptor.

As to positioning, in all preferred embodiments, the power source is a discrete entity which is held and contained entirely within the internal confines of the controller assembly 28. In less preferred embodiments, however, the source of electric current can be a self-contained, separate and free standing unit which is in electric communication with the controller assembly via an electrical cable and connector module linkage.

4. Process Controller Assembly

Figure 15:
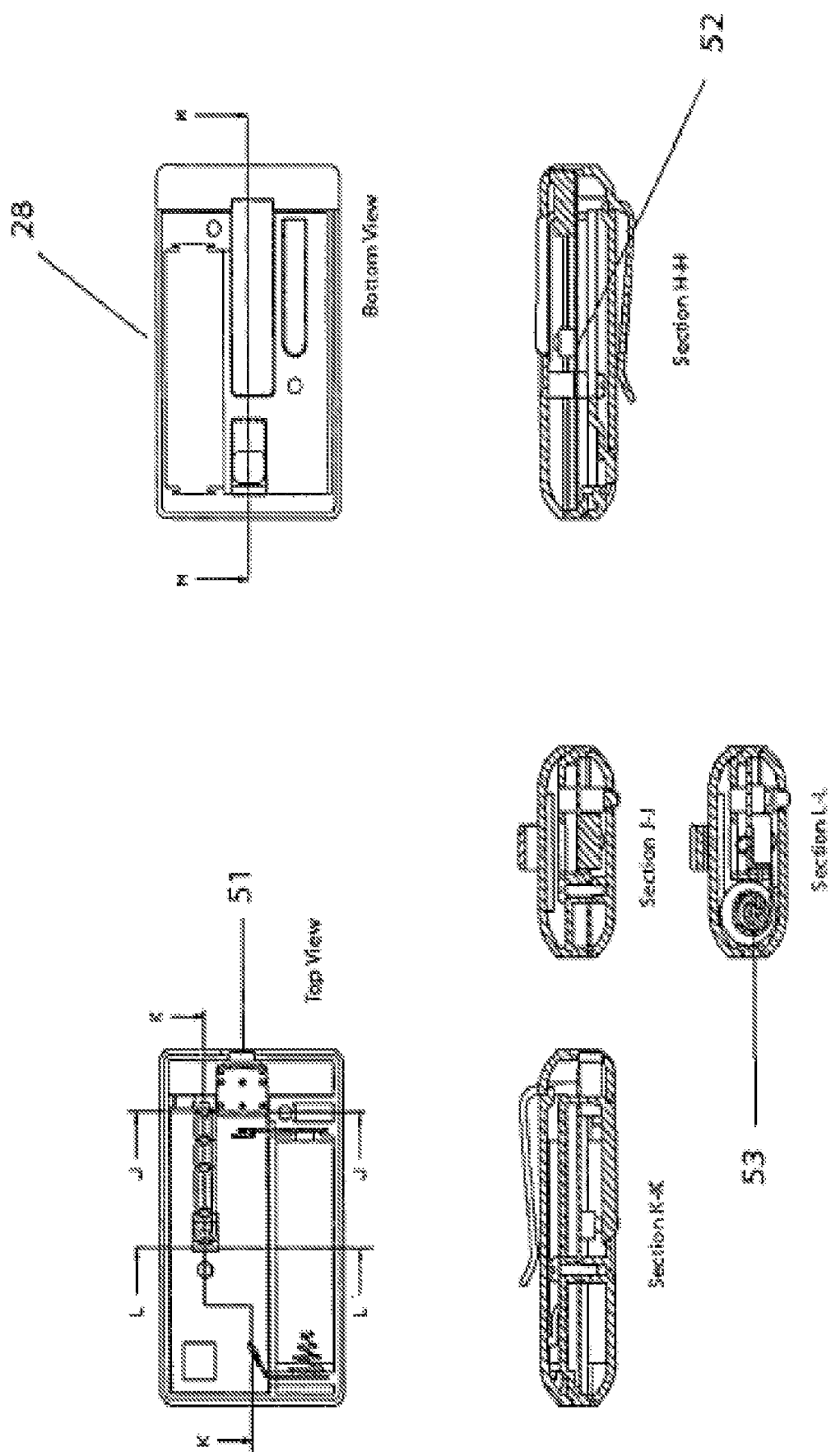
FIGS. 15a, 15b, 15c, 15d, 15e and 15f illustrate the key internal components of the controller assembly.

The process controller assembly is a portable unit component having at least three structural features. Thus, as illustrated by FIGS. 14 and 15 respectively, each process controller assembly will include:

(i) A receiving circuit for receipt of such direct electrical current as is transferred to the controller assembly from the electric source;
(ii) A central processing unit (CPU) for controlling and directing the flow of such electrical current as is received by the controller assembly over time; and
(iii) A delivery circuit for delivering direct electrical current from the controller assembly to another component.

Equally important, it is intended and expected that the process controller assembly will be electrically linked to the other essential components of the apparatus and thus typically will also have:

(a) At least one connector in electrical communication with the source of electrical current for on-demand transfer of electric current to the controller assembly; and
(b) At least one connector in electrical communication with the light generating unit for on-demand conveyance of electric current from the controller assembly to the light generating unit(s). These connectors typically are formed as insulated copper wire cables and jack modules that allow for quick and easy linkage and electrical communication with both the power source and the light generating unit(s).

In all embodiments of the apparatus, the process controller assembly will not operate in the absence of a source of electric current. In addition, the controller assembly, besides switching off the unit after a predetermined time, is mainly a circuitry which provides power to drive the light generating unit properly and efficiently. The controller also ensures that the power delivered to the light generating unit is consistent. It therefore desirably monitors the battery strength, and switches off the unit if the battery if it is unable to supply sufficient power to drive the circuitry properly.

Accordingly, as shown by FIGS. 5-6 and 14-15 respectively, the preferred process controller assembly 28 is dimensionally small in size, light in weight, and portable. It preferably has fixed dimensions which are no larger than an average shirt pocket (i.e., approximately 4.5 inches in length, by 4.5 inches in width, by 1 inch in depth), and is formed of a resilient material such as a moldable thermoplastic. Preferred embodiments of the controller assembly typically include a central processing unit (CPU) in a circuit board 52 which is able to control and direct the flow of electric current in dosage, power, and time from the power source, which is a single AA dry cell battery in the preferred embodiment 53, to the configured irradiation lens 39.

Note also that in the preferred embodiment shown by FIGS. 5 and 6, the source of direct electric current lies internally and is contained within the interior spatial volume of the controller assembly, and appears as the electric battery 29 (dry cell or rechargeable unit). In this instance, the controller assembly 28 also has a socket adapted for the attachment of an insulated copper wire cable and modular jack connector 51, whose other end is joined to the light generating unit 38 disposed within the hollow casing 39 illustrated by FIG. 8.

The controller assembly 28 illustrated by FIGS. 14-15 as a whole is able to deliver the required dosage from the light diode repeatedly over time, which is sufficient to achieve consistent neurostimulation of the brain. Also for portability, a typical battery source of electric energy provides direct current at 1.5 volts. However, subject to the circuit to the type of light source being used, a broader range of direct current voltages is acceptable.

The central processing unit ("CPU") of the controller assembly is preferably able to regulate light energy power output at 10 to 1000 mW or more. When it is regulated, the power is typically fixed. These light energy power outputs result in the emitted light of the apparatus being therapeutically effective after a treatment time of only 10 to 30 minutes per session duration for the preferred embodiments.

It is intended and expected that any conventionally known and interchangeable electric cables and connectors will be used to link the controller assembly to the irradiation lens. This also provides a distinct advantage and benefit to the user, namely the option to exchange one configured irradiation lens (able to transmit light at a first wavelength) for another irradiation lens (able to transmit light at a second and different wavelength), and thereby permits the use of different lasers and alternative light emitting diodes able to deliver different wavelengths of visible and invisible light energy with one single controller assembly.

In another embodiment, the controller assembly may have controls to provide more delivery and operating options to offer more versatility. This particular advantage and benefit is provided through the selection of various preconfigured settings on the controller to match the type of light and its wavelength, improve user-interface and reduce errors. This mode and manner of exchanging the light generating units at will or as needed allows the therapeutic use of different light ranges and alternative light wavelengths by a single patient without any need for purchasing multiple treatment systems or more than one apparatus.

Figure 16:
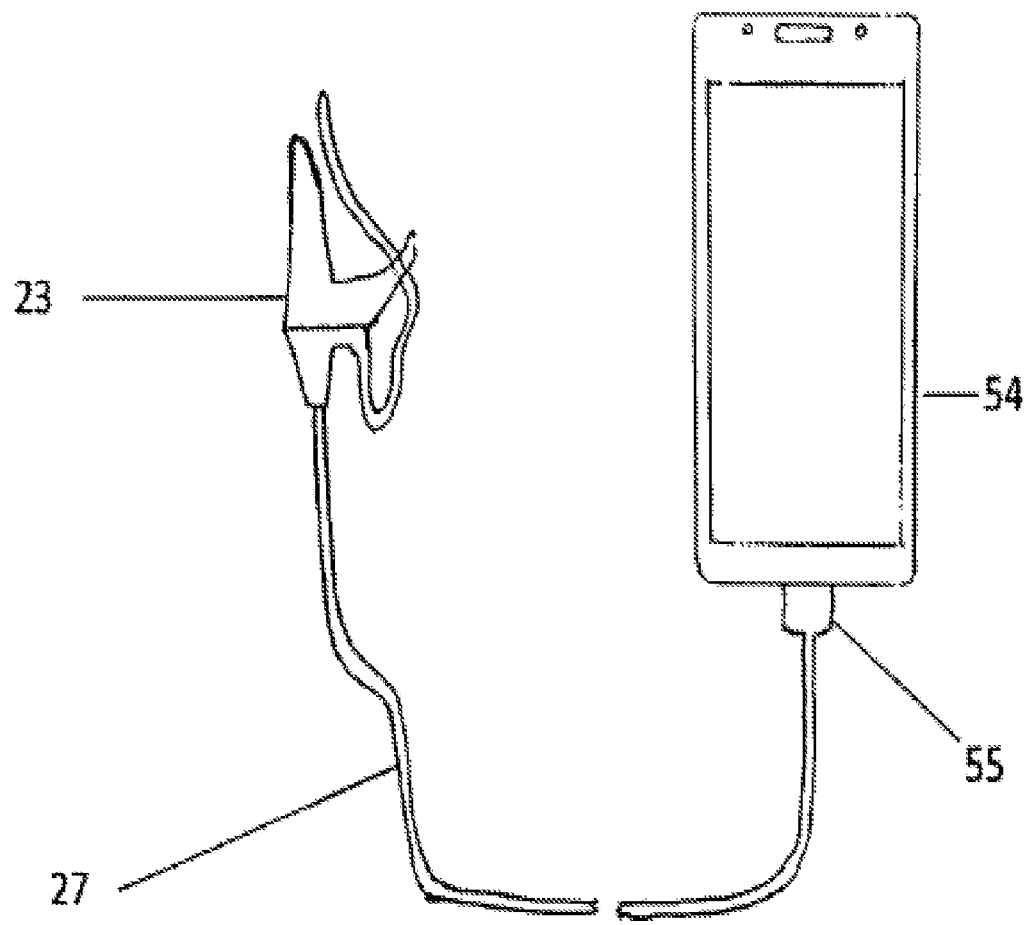
FIG. 16 illustrates the concept of the smart phone as the alternative to the controller assembly.
Figure 17:
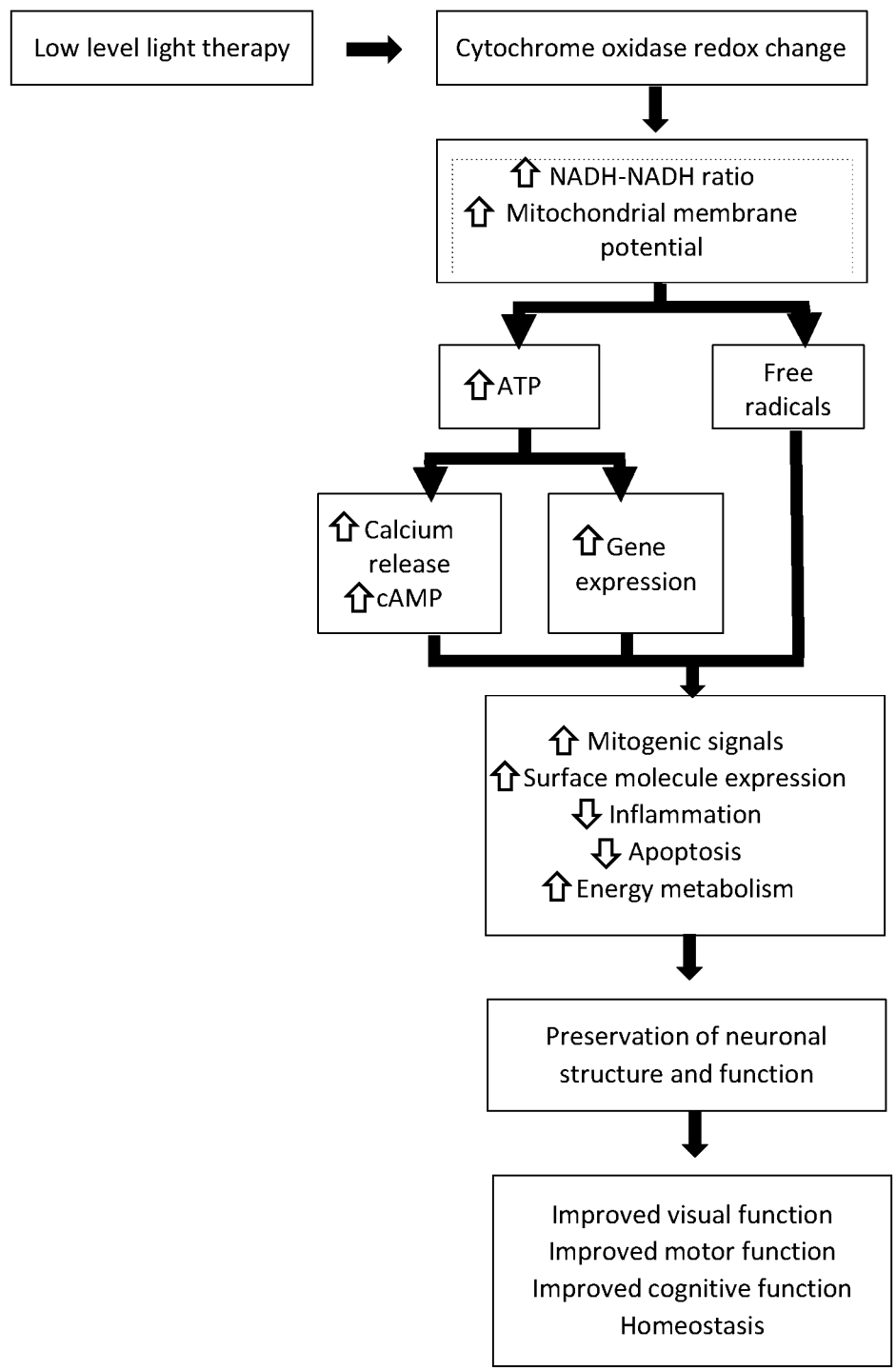
FIG. 17 illustrates the intracellular mechanism of action of low level light therapy.
Figure 18:
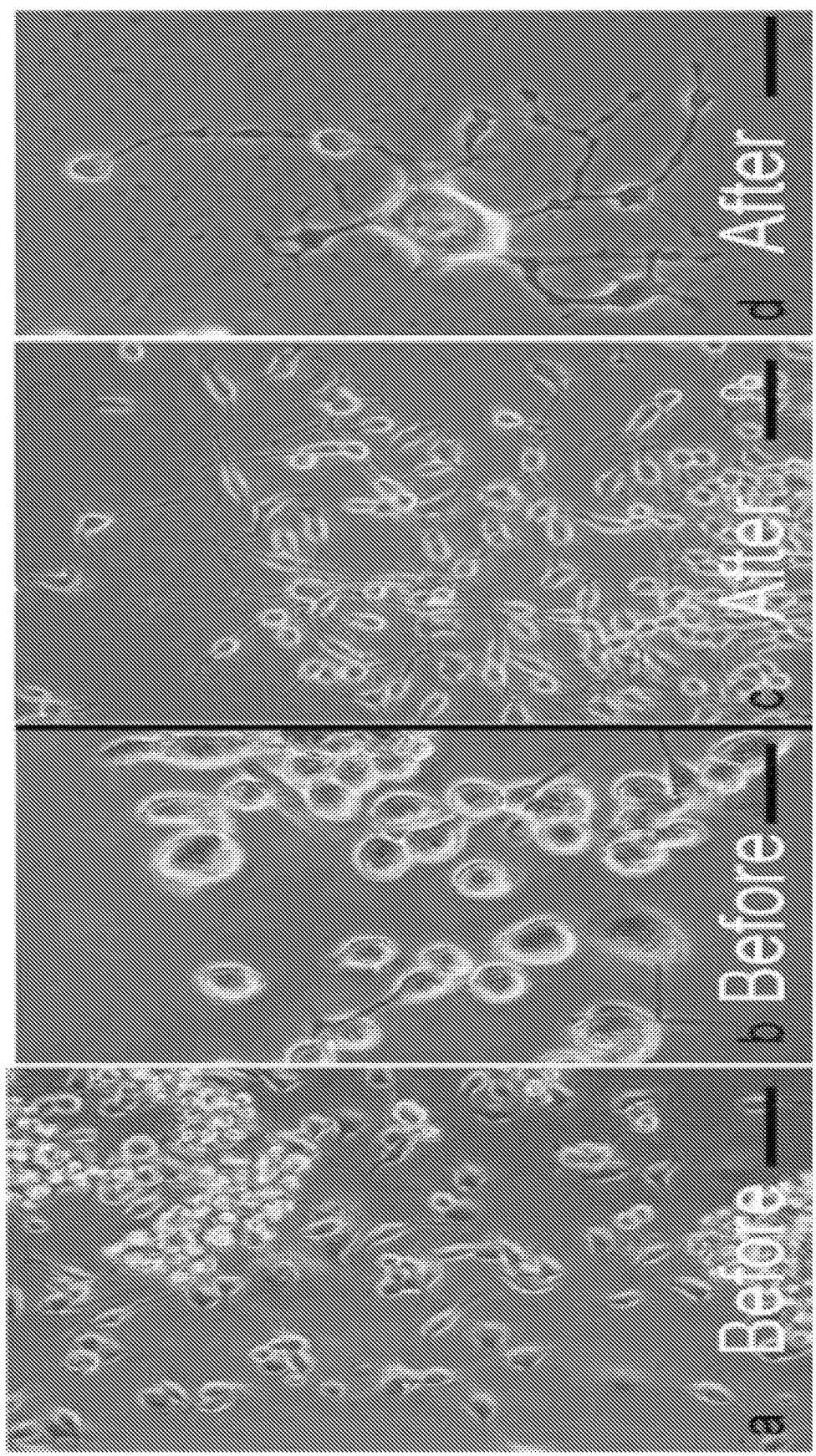
FIG. 18 illustrates a neurite elongation experiment with in vitro post-oxidative stress.
Figure 19:
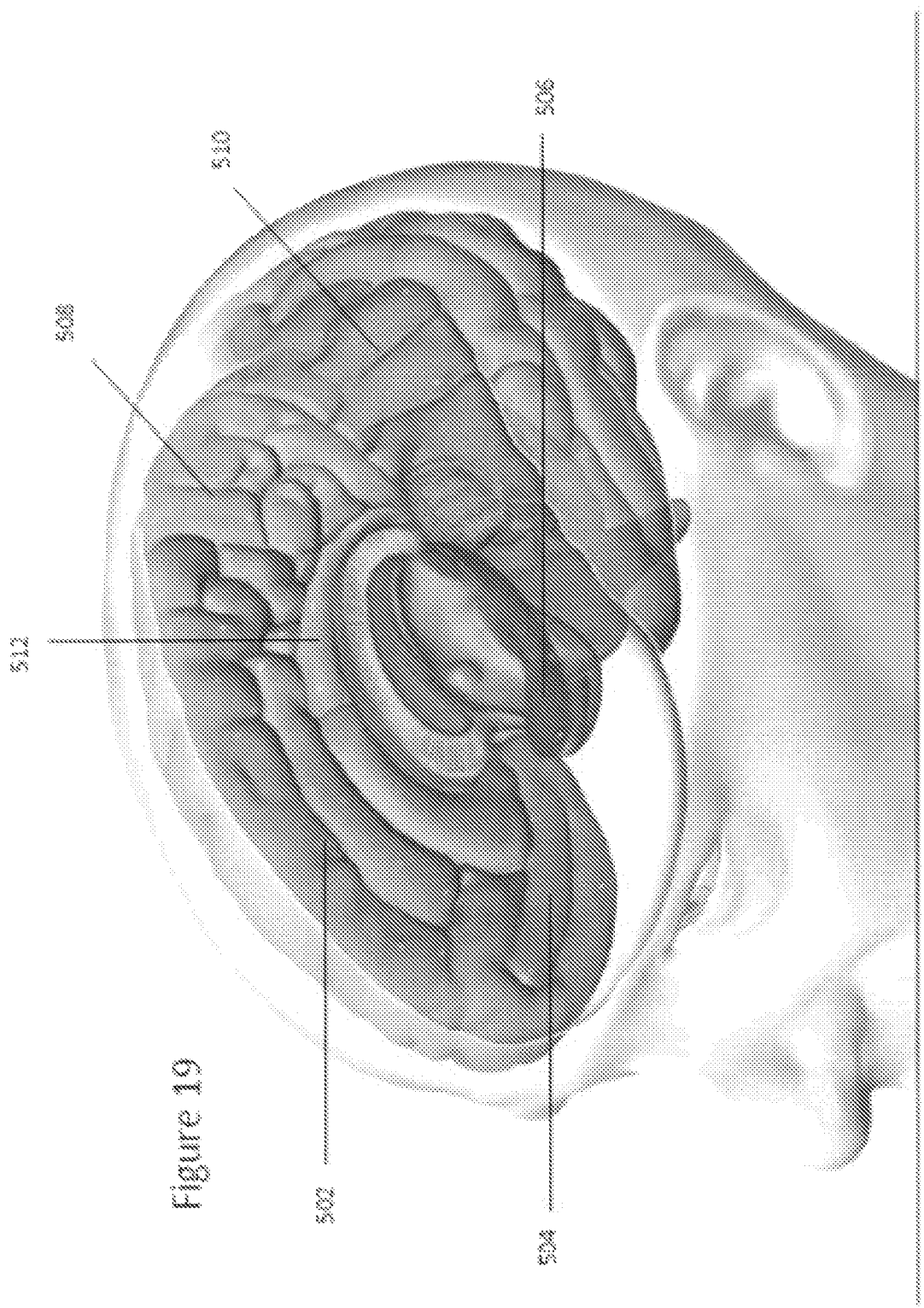
FIG. 19 illustrates cortical hubs in the brain's Default Mode Network.

The Mobile Smart Phone Option:

In another embodiment, the function of the controller assembly 28 may be replaced by a smart phone operating on one of the popular mobile platforms, and which may include those from Apple, Android, Blackberry and Windows as illustrated by FIG. 16. The applicator assembly 23 will now be connected via a cable (formed of similar materials as for the other embodiments 27) to the smart phone 54 instead with a discrete controller unit. The smart phone 54 carries a downloadable software application ("App") that would largely duplicate the software functions in the controller assembly 28. A modified attachment containing interface processing software in a computer chip 55 will provide an interface between the existing applicator and the proprietary smart phone platform. With this embodiment, the user need not carry an additional or separate controller unit, and yet the "App" will also contain more software controls and graphic interfaces.

Preferred System and Apparatus Embodiments of the Present Invention:

As shown in FIGS. 20 to 25 and 29, the present invention provides a preferred embodiment of an apparatus 100 which combines a transcranial light therapy headset 102 and an intranasal light therapy unit 104. The portable controller assembly 106 can serve as a power source and central processing unit for both the transcranial headset 102 and intranasal unit 104.

The headset 102 comprises one or more configured irradiation units 108, 110, 112 and 114, each of the configured irradiation units 108, 110, 112 and 114 including a portable hollow casing having fixed dimensions, a sized internal spatial volume, and an external surface configuration suitable for application to the skull 116. The portable casing comprises: (i) a light energy transmitting material which forms at least a portion of the configured external surface for said hollow casing, and (ii) at least one light generating unit entirely housed and contained within said internal spatial volume of said hollow casing and which is capable of generating light energy of at least one preselected wavelength selected from the group consisting of near infrared red light wavelengths and visible red light wavelengths, at a predetermined energy intensity and for a preset time duration on-demand sufficient to penetrate through the skull and to pass into the brain.

A frame 118 is provided in the headset 102 to support the configured irradiation units 108, 110, 112 and 114 and to adapt the headset 102 for at will placement of the light transmitting external surface of the configured irradiation units 108, 110, 112 and 114 at a fixed position and desired irradiation direction on the skull 116. Support pads 128 are preferably provided to help secure the headset 102 to the skull 116 and to make the headset 102 more comfortable for the patient to wear.

In the preferred embodiment shown in FIGS. 20 to 25 and 29, the frame 118 supports four configured irradiation units 108, 110, 112 and 114, and each configured irradiation unit 108, 110, 112 and 114 forms a cluster head with three light generating units each. The four cluster heads are positioned in the headset 102 such that they target specific cortical hubs in the brain. In the preferred embodiment shown in FIG. 25, the cluster heads are positioned to target the following parts of the brain:

A. On the midline, at the front hairline: the targeted brain regions include the left and right ventral mesial prefrontal cortex areas, and optionally, the anterior cingulate gyrus areas, which are part of the Salience Network;

B. On the midline, halfway between the occipital protuberance and the vertex of the head: the targeted brain regions include the left and right precuneus cortical areas, and optionally, the posterior cingulate gyrus areas, inferior to the precuneus areas;

C. On the left side of the head, posterior and superior to the borders of the left ear: the targeted brain region is the left angular gyrus area in the lateral, inferior parietal cortex, and optionally the left, posterior cingulate gyrus, located very deep (at the midline) from the Left angular gyrus area; and D. On the right side of the head, posterior and superior to the borders of the right ear: the targeted brain region is the right angular gyrus area in the lateral, inferior parietal cortex, and optionally, the right, posterior cingulate gyrus, located very deep (at the midline) from the right angular gyrus area.

Figure 20:
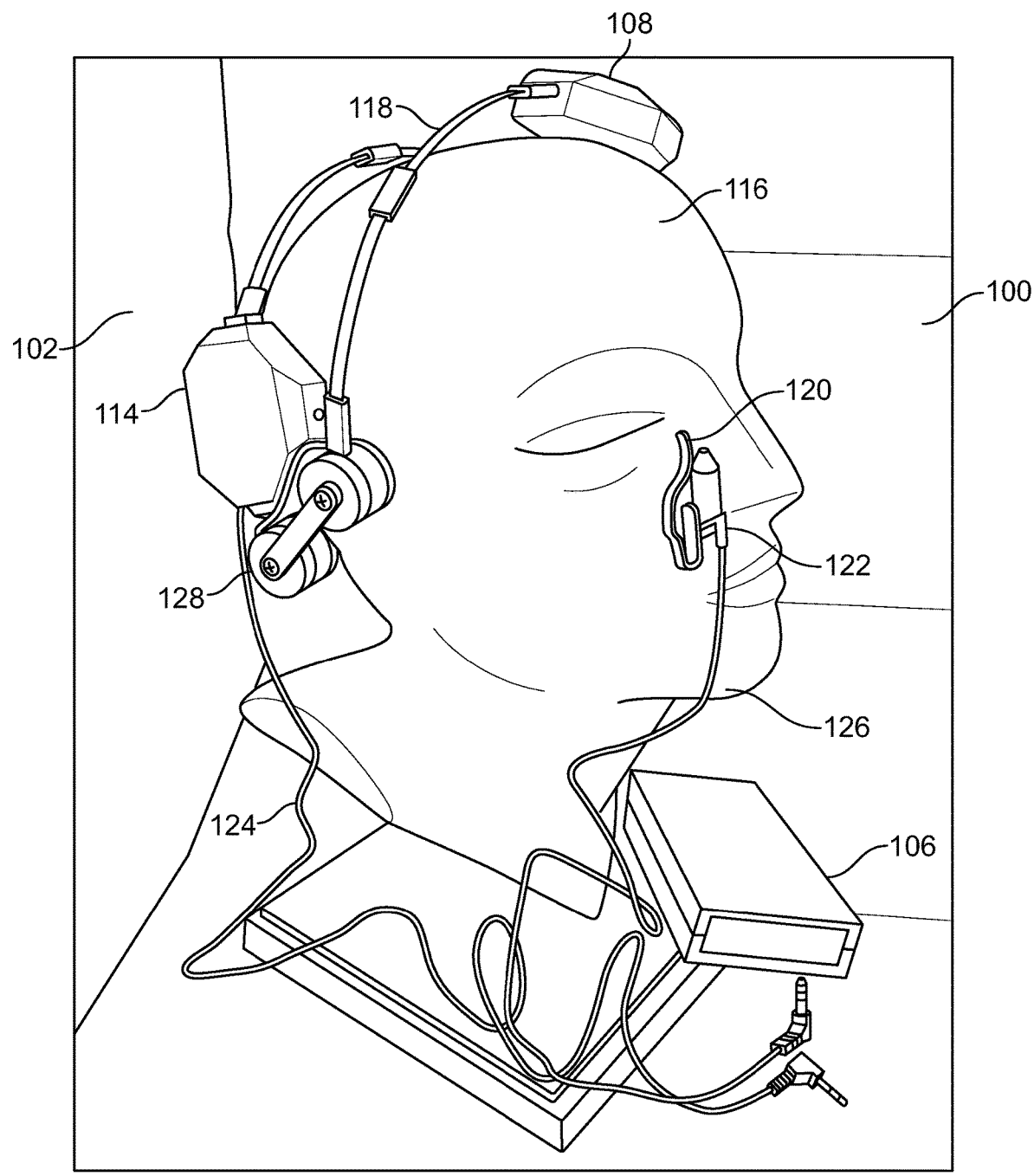
FIG. 20 illustrates a perspective view of a preferred embodiment of the apparatus of the present invention.
Figure 21:
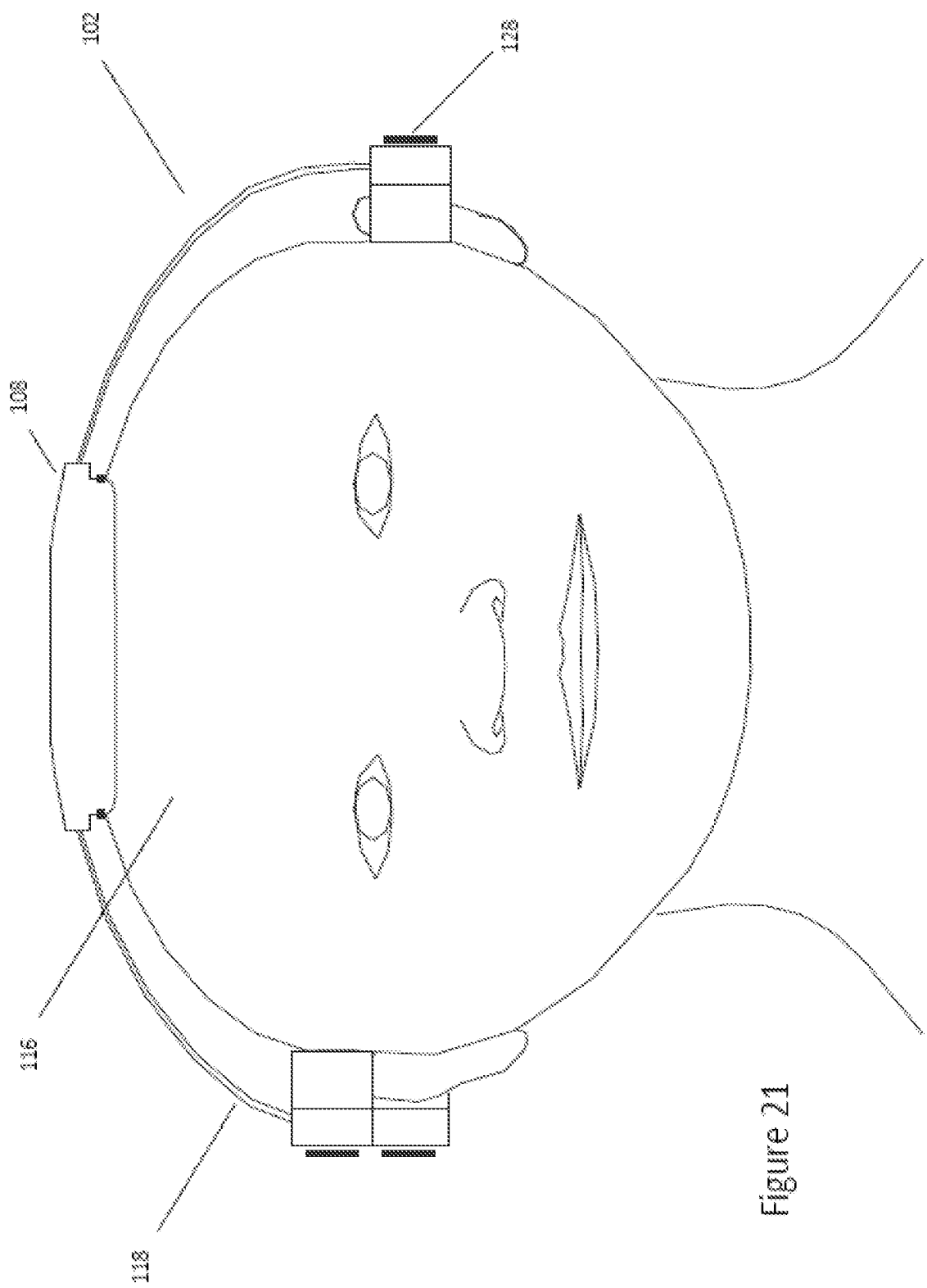
FIG. 21 illustrates a front view of a preferred embodiment of the apparatus of the present invention.
Figure 22:
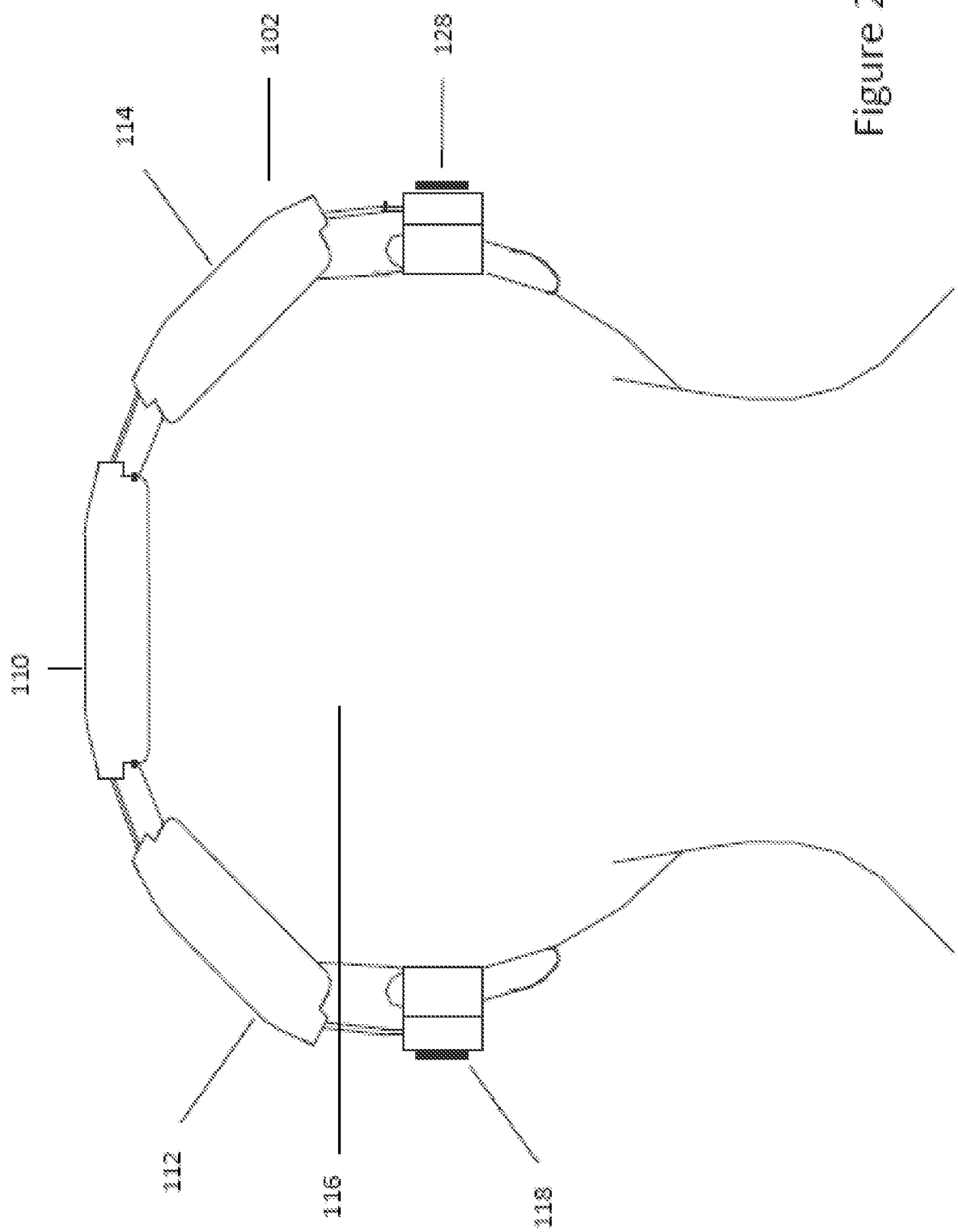
FIG. 22 illustrates a back view of a preferred embodiment of the apparatus of the present invention.
Figure 24:
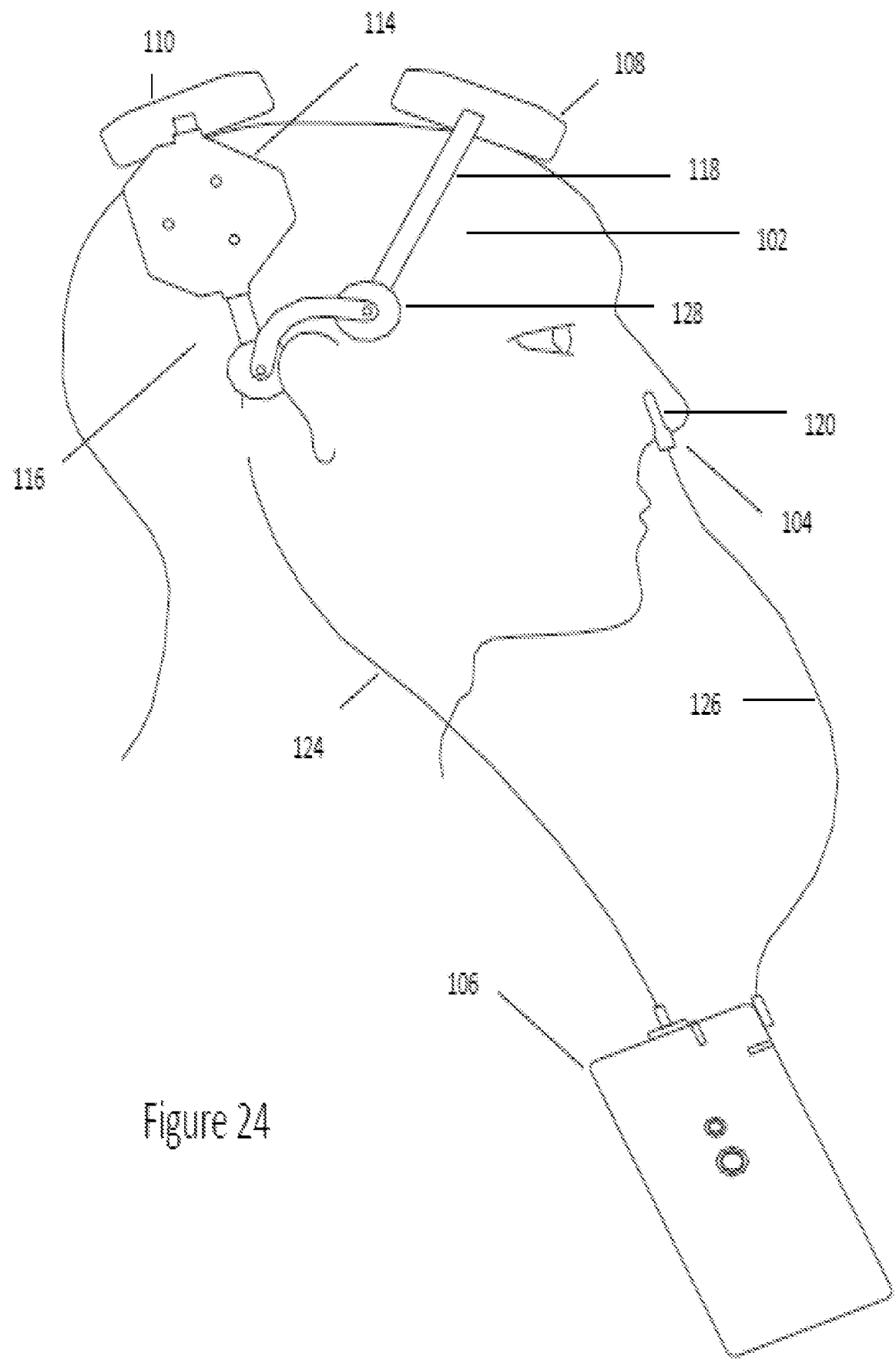
FIG. 24 illustrates a right view of a preferred embodiment of the apparatus of the present invention.
Figure 29:
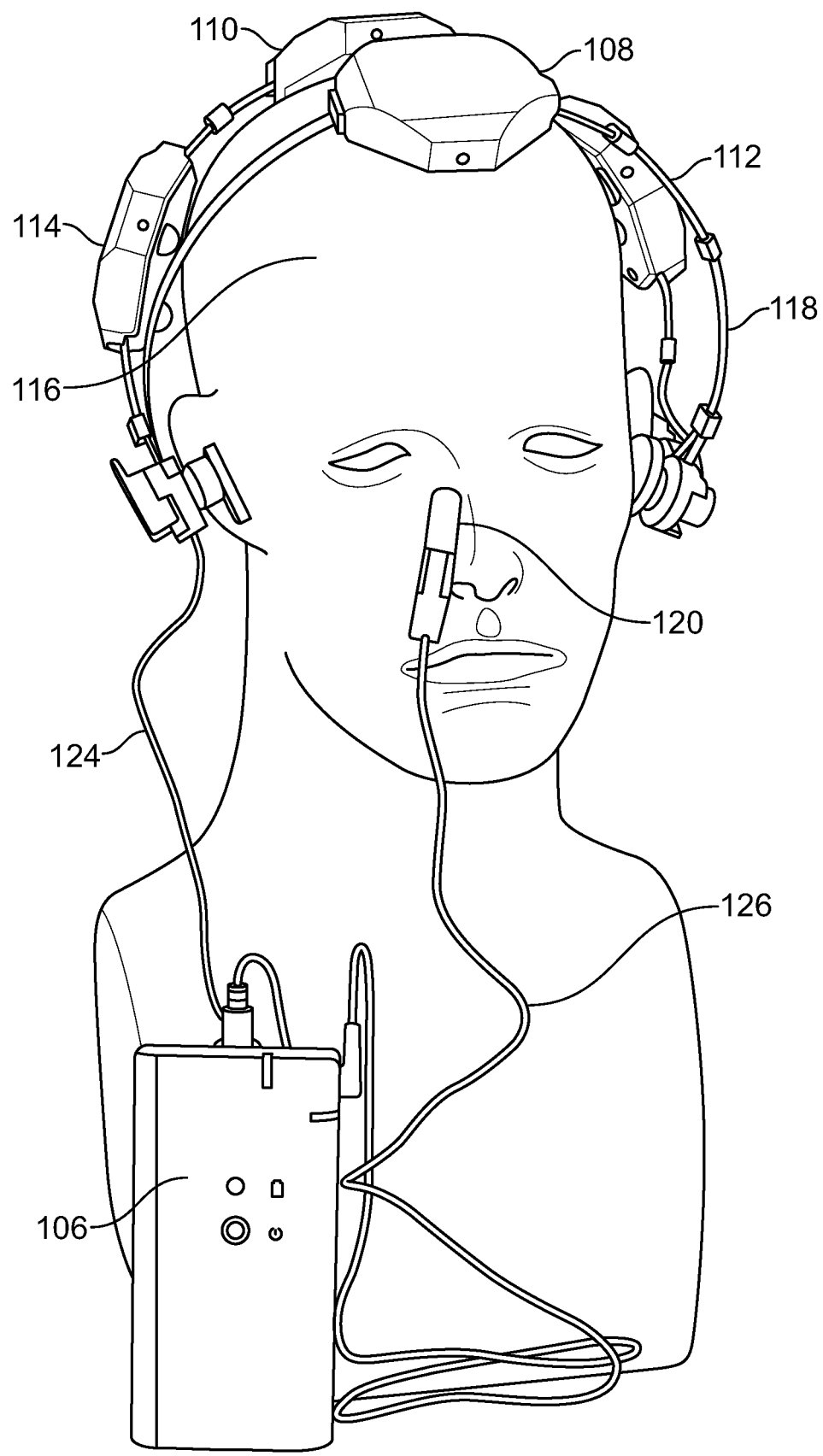
FIG. 29 illustrates a perspective view of a preferred embodiment of the apparatus of the present invention.

As can be seen in FIGS. 20, 24 and 29, the intranasal light therapy unit 104 includes a nose clip 120. The nose clip 120 holds a configured irradiation lens 122 inside one of the nostrils of the subject. The configured irradiation lens 122 includes a portable hollow casing having fixed dimensions, a sized internal spatial volume, and an external surface configuration suitable for application to the interior of the nostrils. The portable casing comprises: (i) a light energy transmitting material which forms at least a portion of the configured external surface for said hollow casing, and (ii) at least one light generating unit entirely housed and contained within said internal spatial volume of said hollow casing and which is capable of generating light energy of at least one preselected wavelength selected from the group consisting of near infrared red light wavelengths and visible red light wavelengths, at a predetermined energy intensity and for a preset time duration on-demand sufficient to penetrate through the nasal tissues and to pass into the brain.

A first connector 124 is in electrical communication with the configured irradiation units 108, 110, 112 and 114 of the transcranial headset 102. A second connector 126 is in electrical communication with the configured irradiation lens of the intranasal light therapy unit 104. This allows for on-demand conveyance of direct electrical current from the portable controller assembly 106 to the light generating units in the configured irradiation units 108, 110, 112 and 114, as well as the light generating unit(s) of configured irradiation lens in the intranasal light therapy unit 104.

As seen in FIG. 25, the configured irradiation units 108, 110, 112 and 114 of the transcranial headset 102 direct light energy to cortical hubs in the dorsal or upper areas of the brain which are difficult to reach using intranasal therapy. Conversely, the configured irradiation lens 122 of the intranasal light therapy unit 104 directs light energy to cortical hubs in the ventral or underside of the brain which are difficult to reach using transcranial light therapy.

Operational Parameters for Preferred Embodiment:

In the preferred embodiment shown in FIGS. 20 to 25 and 29, the system and apparatus of the present invention have the following operational parameters:

1. Each of the configured irradiation units 108, 110, 112 and 114 in the transcranial headset 102 preferably comprises a light-emitting diode (LED) cluster head. Each cluster head is preferably approximately 4 cm by 4 cm in size. Each cluster head in the transcranial headset 102 preferably comprises three (3) light-emitting diodes.
2. The four LED cluster heads of the transcranial headset 102 are used simultaneously to treat the following cortical areas which are part of the Default Mode Network (and part of the Salience Network) of the brain:
    A. On the midline, at the front hairline: the targeted brain regions include the left and right ventral mesial prefrontal cortex areas, and optionally, the anterior cingulate gyrus areas, which are part of the Salience Network;
    B. On the midline, halfway between the occipital protuberance and the vertex of the head: the targeted brain regions include the left and right precuneus cortical areas, and optionally, the posterior cingulate gyrus areas, inferior to the precuneus areas;
    C. On the left side of the head, posterior and superior to the borders of the left ear: the targeted brain region is the left angular gyrus area in the lateral, inferior parietal cortex, and optionally the left, posterior cingulate gyrus, located very deep (at the midline) from the Left angular gyrus area; and
    D. On the right side of the head, posterior and superior to the borders of the right ear: the targeted brain region is the right angular gyrus area in the lateral, inferior parietal cortex, and optionally, the right, posterior cingulate gyrus, located very deep (at the midline) from the right angular gyrus area.
3. The intranasal unit 104 comprises one configured irradiation lens 122 with preferably one intranasal light-emitting diode (LED). The intranasal diode targets the left and right full ventral side of the forebrain, parts of anterior rostral portion of the hindbrain and parts of inferior temporal lobe (including the mesial, inferior temporal gyrus areas and the lateral entorhinal cortex of the hippocampus areas).
4. Power Source: Preferably a rechargeable power pack with NiMH batteries.
5. All light generating units preferably provide light energy of 620 nm to 1400 nm wavelength, more preferably 700 nm to 1000 nm wavelength, and even more preferably a 810 nm wavelength.
6. Power Output:
    A. Transcranial headset 102 LED cluster heads: Each of the 3 diodes in the transcranial headset 102 LED cluster head preferably has a power output of 20 mW to 60 mW, more preferably a power output of about 41 mW. Each transcranial LED cluster head has a preferred combined power output of 60 mW to 180 mW, more preferably about 123 mW. The total power of the four transcranial headset 102 LED cluster heads which are used simultaneously is preferably 240 mW to 720 mW, more preferably about 492 mW.
    B. Intranasal unit 104 LED: The power output of the single diode of the intranasal unit 104 is preferably 10 mW to 30 mW, more preferably about 23 mW.

The total power output of the four transcranial headset 102 LED cluster heads plus the single intranasal unit 104 LED is preferably 250 mW to 750 mW, more preferably 515 mW. These are all used simultaneously for preferably a 20 to 25 minute treatment.

7. Power Density:
    A. The power density of each transcranial headset 102 LED cluster head is preferably 20 to 60 mW/cm$^2$, more preferably about 41 mW/cm$^2$
    B. The power density of the single intranasal unit 104 diode is preferably 10 to 30 mW/cm$^2$, more preferably about 23 mW/cm$^2$
8. Energy density dose at each treatment:
    A. Each transcranial headset 102 LED cluster head: Preferably 20 to 30 J/cm2, more preferably about 25 J/cm2.
    B. Intranasal unit LED: Preferably 10 to 20 J/cm2, more preferably about 14 J/cm2. There is a lower energy density for the intranasal unit because the barriers to light energy penetration are less substantial than for the transcranial headset.
9. All diodes in the transcranial unit 102 LED cluster heads, and the single intranasal unit 104 diode are preferably pulsed at 10 Hz, 50% duty cycle.
10. Total treatment time: Preferably about 20 to 25 minutes.
11. Use of this preferred transcranial-intranasal device 100 should preferably be restricted to no more than once every 2 or 3 days to avoid possible overdose by subjects who are particularly sensitive to electromagnetic energy or subjects with brain infections.

A preferred apparatus using the above operational parameters has been shown in field tests to successfully improve conditions such as brain fogginess, impaired cognition and chronic facial pain.

Preferred System and Apparatus Features for Intranasal Light Therapy Unit:

A preferred embodiment for the intranasal light therapy unit is shown by FIGS. 5-12 and FIGS. 15-18 respectively as a unified system and ready to use medical device. As seen therein, the non-invasive apparatus FIGS. 5 and 6 provides an self-administrable applicator device 23, a structural article of convenience, which holds and supports a configured irradiation lens 24 in a desired fixed position within the nasal cavity, and which is dimensionally small in size, is at least partially transparent, and is purposefully shaped to allow its insertion into a nasal cavity space without causing meaningful impairment to the subject's ability to breathe.

The self-administrable applicator device 23 is formed as a resulting combination and integration of two separate structural entities: a transparent and partially hollow configured irradiation lens 24 having at least one discrete light diode within its housing 25 and a support base 26 that connects the configured irradiation lens 24 with a connecting power cable 27.

Structurally, the configured irradiation lens 24 encapsulates a diode housing 25 which contains the diode light source in a form either as a light emitting diode (LED) or as a laser. In addition, the configured irradiation lens 24 is formed at least in part of a light transmitting material, and together with the diode housing 25, is angled and integrated with the lens to release the light photons at any desired direction and dispersion angles.

Figure 7A:
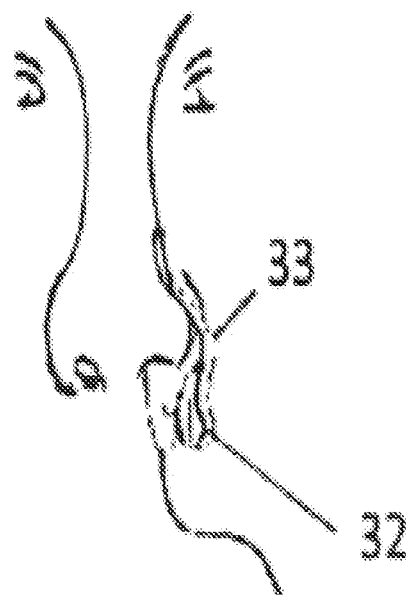
FIGS. 7a and 7b illustrate the set form version of the applicator and the cantilever based version of the applicator respectively.
Figure 7B:
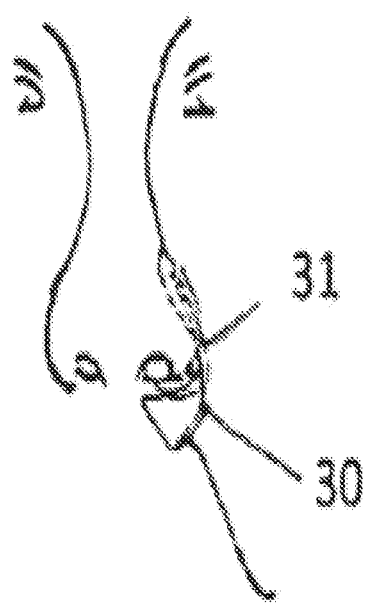
Figure 8A:
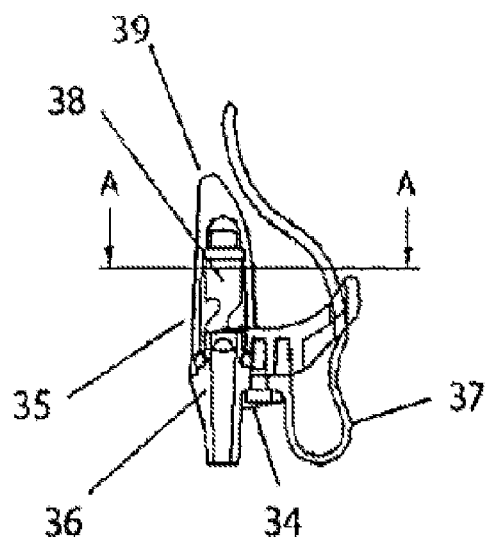
FIGS. 8a and 8b are engineering drawings of the side and top views respectively of the applicator assembly.
Figure 8B:
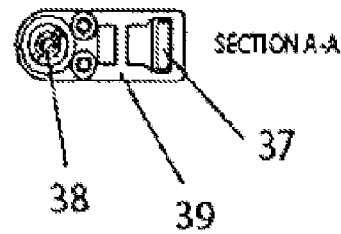
Figure 9A:
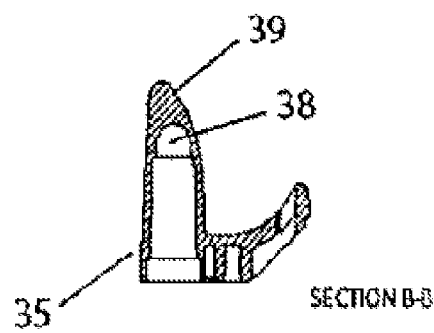
FIGS. 9a and 9b are engineering drawings of the side and top views respectively of the L-shaped transparent lens unit of the applicator.
Figure 9B:
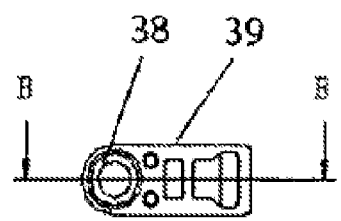

In the embodiment of the self-administrable applicator means shown by FIGS. 5-7, the device can include one or more support structures formed of different plastics that serve to hold the configured irradiation lens 24 (i.e., the lens/diode complex) rigidly in the desired direction, and yet hold the configured irradiation lens 24 securely to the anatomy of the nose comfortably. The applicator device may be in a set format as seen in FIG. 7a or can be manipulated with a cantilever as shown by FIG. 7b.

In the more preferred embodiments, the system specifications are controlled by a circuit board containing an embedded software program(s) that is housed in a controller unit 28, and which is powered by a disposable dry cell battery. In the preferred embodiment and the set format of the applicator shown by FIG. 7b, the support structures 30 are rigid and set, whereas the clip 31 is flexible. Both the support structures 30 and the clip 31 are molded out of durable plastic materials.

In the embodiment having the cantilever-based applicator device as shown by FIG. 7a, the support base carries a cantilever 32, which when depressed with the fingers, will open and then allow the applicator to slide the lens into the cavity space of the nostril. The clip 33 will hold the applicator device securely to the nose.

In the preferred format illustrated by FIGS. 8a, 8b, 9a, and 9b respectively, the applicator device is a single cooperative entity which includes a support base 34 for the configured irradiation lens 35, and is collectively structured as a discrete cradle section 36 and a contoured nose clip or fitting 37 fashioned for easy at will attachment to and detachment from the exterior surface of the human nostril. The configured irradiation lens is part of a single clear plastic molding that dimensionally extends to encase part of the support base 39. The nose clip 37, apart from serving physically as contoured friction fitting by which to hold the configured irradiation lens 35 in proper position within the nostril, is preferably composed of a white or opaque material which contributes to its service as a light barrier and reflector; and which acts to redirect substantial stray light passing through the tissue wall of the nostril back towards the interior of the nasal cavity wall.

In addition, as shown by FIGS. 5-6 respectively, the self-administrable applicator means 23 is in electrical communication (via a cable and jack module connector 27) with a process controller assembly 28, a control and power supply construct which is compact, lightweight and sufficiently portable to be carried by hand, fit inside a shirt pocket, or be clipped to a shirt. In this preferred embodiment, the process controller assembly 28 includes a portable and disposable/replenishable source of on-demand direct electrical current, and is able to convey carefully regulated dosages of electric power on-demand to the light generating unit(s) 29 contained within with the applicator assembly 23 for light irradiation therapy. In this instance, the process and power controller assembly 28 also includes and provides an automatic timer and power switch 28a. The controller automatically shuts off the electric current conveyed to the light generating unit(s) after the passing of a prechosen amount of time.

The Configured Irradiation Lens for Intranasal Light Therapy Unit:

Architecturally as shown in detail by FIGS. 8 and 9 respectively, the preferred configured irradiation lens 39 for intranasal light therapy appears as a substantially "L" shaped construct. However, the configured irradiation lens 39 as such is preferably formed by and is the result of combining and integrating two other separate structural entities:

(i) A portable hollow casing 35, formed in least in part of a light transmitting material, and which serves at least in part as a reflective lens that reflects light in a desired direction; and (ii) At least one discrete light generating unit or diode 38, which is entirely housed and contained within the interior spatial volume of the hollow casing 35.

Together the discrete light generating unit 38 and the portable hollow casing 35 collectively form the configured irradiation lens 39, a construct able to emit and direct light energy of at least one predetermined wavelength, power and pulsed (or continuous wave) mode on-demand.

It is important to understand and appreciate the meaning and effect of this "L" shaped construction for intranasal light therapy and particular attention is therefore directed to the views provided by FIGS. 8a-8b and FIGS. 9a-9b respectively. As shown therein, although the hollow casing 35 is formed as a lens and includes the entire "L" shaped structure 39, the light generating unit 38 is typically placed into and contained by only the vertical or upright volumetric portion of the "L" shaped casing 39. Consequently via this arrangement illustrated by FIGS. 8a, 8b, 9a, and 9b respectively, the horizontal or axial portion 39 is typically devoid of any internal contents, and exists merely for physical support by the cradle section 36 of the supporting base 34 in the applicator.

Also, via this positioning arrangement, it is only the vertical or upright volumetric portion 35 of the "L" shaped casing which must be formed of a light transmitting or transparent material. In contrast, the horizontal or axial portion of the hollow casing 39 may be formed of any resilient material, transparent or not.

Figure 10:
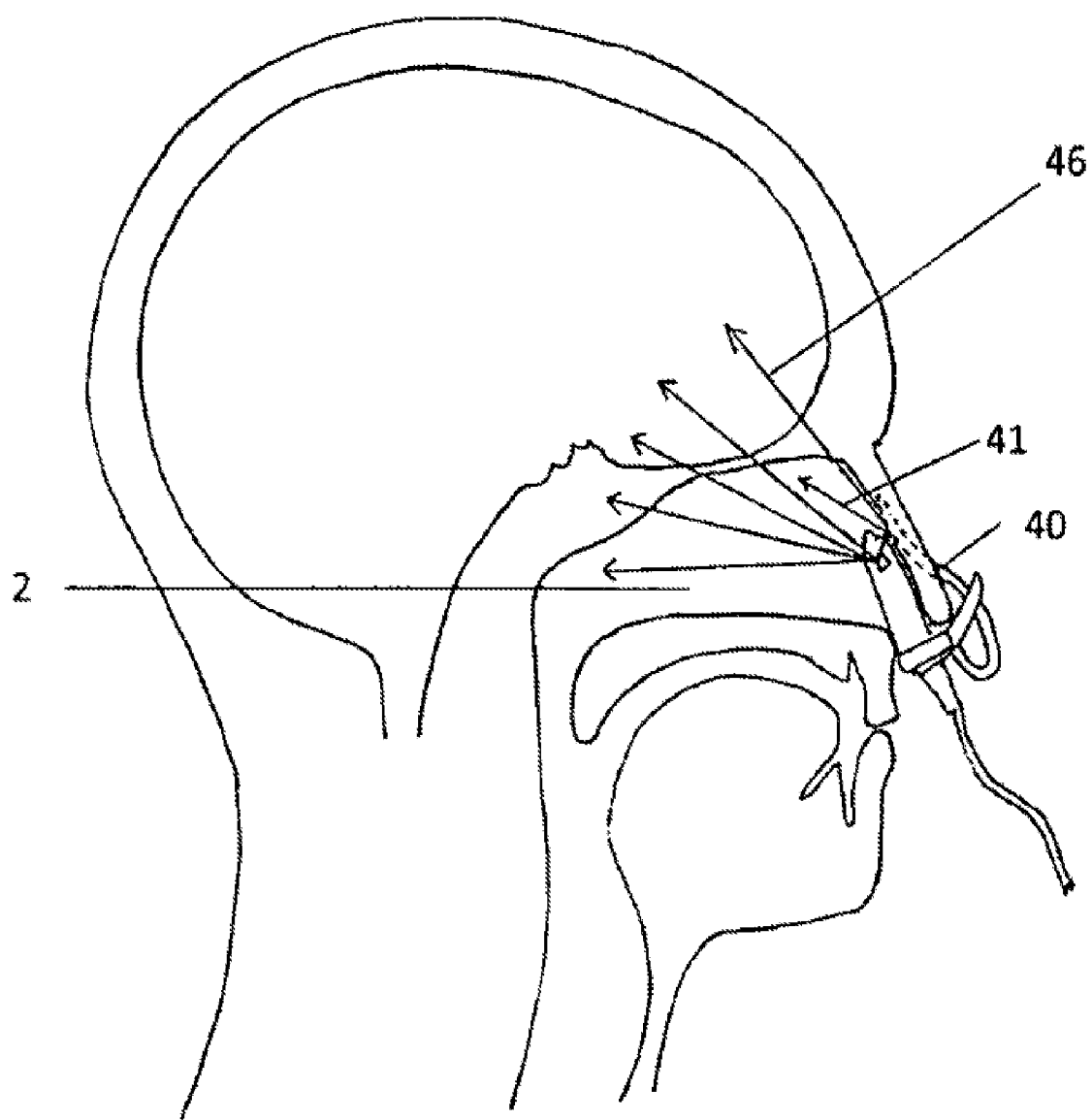
FIG. 10 illustrates the positioning of the applicator of the apparatus, secured by the nose clip and shows the direction of the emitted light rays.
Figure 11:
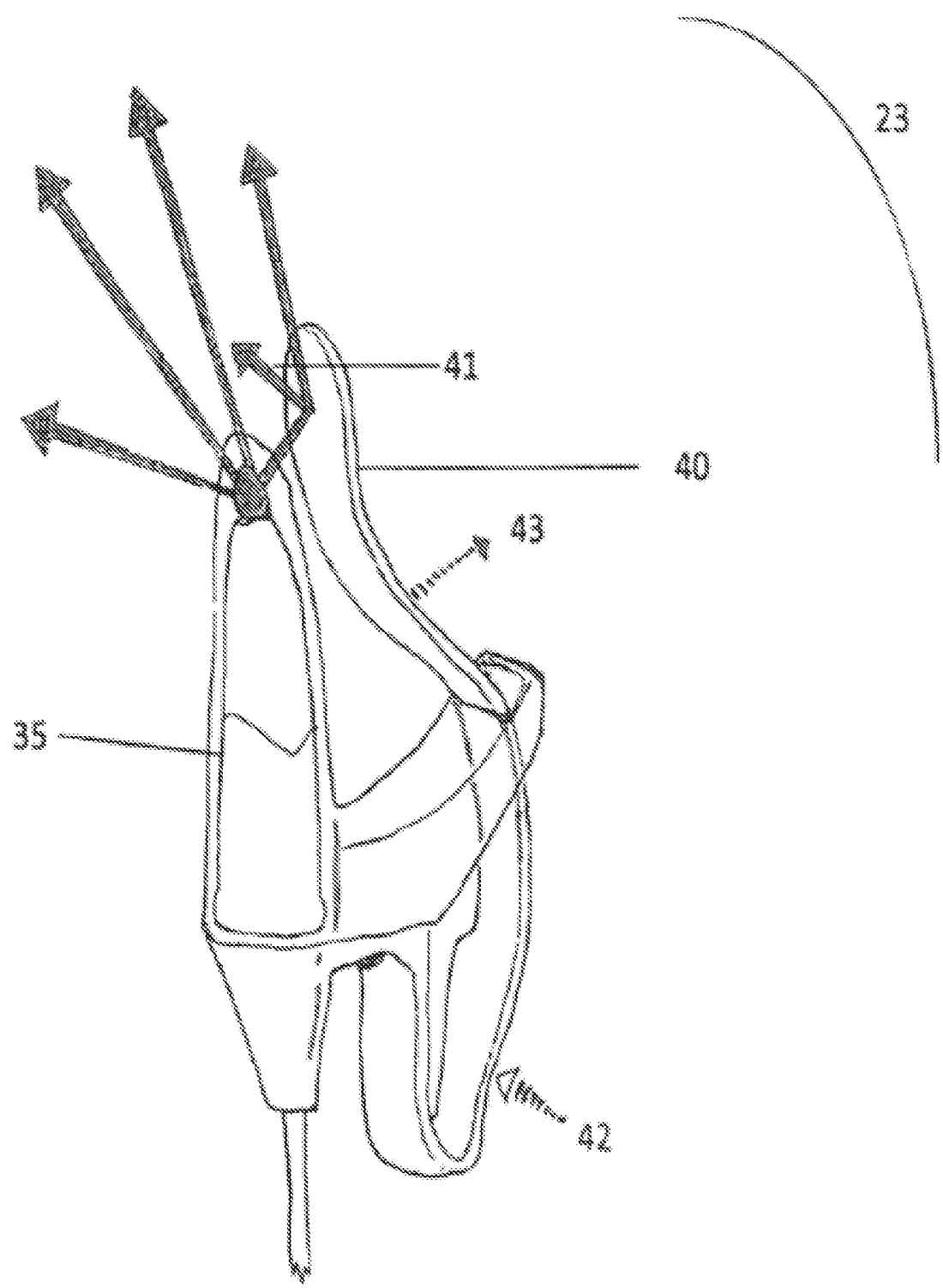
FIG. 11 illustrates how the nose clip of the apparatus minimizes leakage of light and redirects them back into the nasal cavity and towards the brain—as well as how the cantilever is manipulated to enable the irradiation lens is slipped into the nostril.

The Nose Clip as a Reflecting Accessory and its Function:

In the preferred embodiments illustrated by FIGS. 10 and 11 respectively, the nose clip 40 doubles as a functioning clip by which to secure the applicator device to the nose anatomy; and to function as an accessory to minimize leakage of photons; as well as to reflect these photons 41 back into the nasal cavity to maximize power efficiency. The applicator article is molded with a cantilever which functions by depressing the bottom 42 (with a finger) to allow the clip to open 43 the lens assembly 35 and to slip it comfortably onto the nose comfortably. Once the finger pressure is released, the clip will resume its prior default position and thereby secure the applicator device to the structural nose anatomy.

Figure 12:
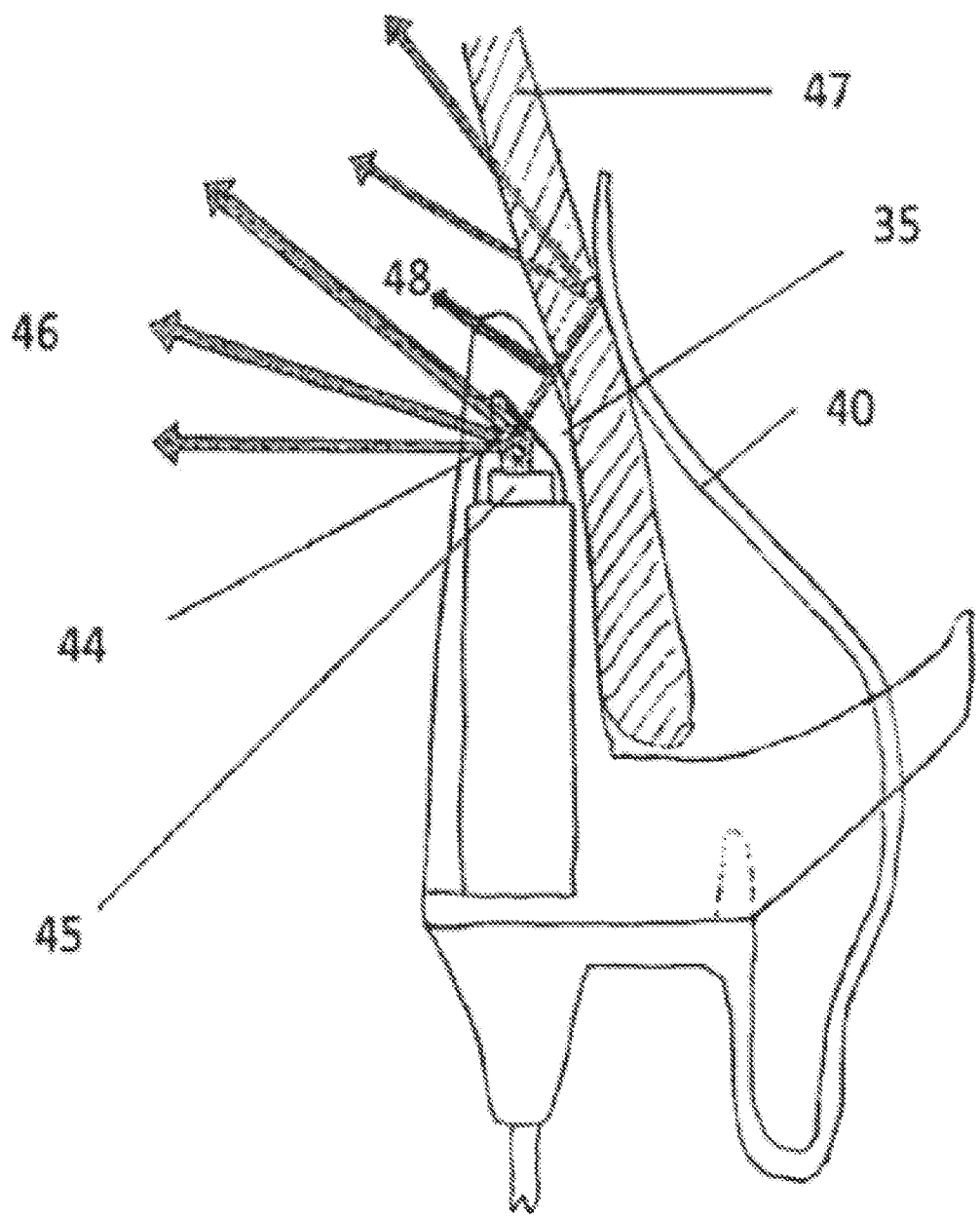
FIG. 12 further illustrates the role of the positioning of the diode, the micro-lens, the irradiation lens and the nose clip of the apparatus in influencing the direction of the light.

The Micro-Lens and Other Light-Directing Configurations for Intranasal Light Therapy Unit:

FIG. 12 is an illustration showing a low level laser embodiment with the option of a micro-lens 44 which serves to deflect the light released by the diode 45 towards the chosen target area(s). By incorporating this feature, the embodiment minimizes the dispersion of light 46, and minimizes the power requirement to achieve efficacy. Also, much of the remaining leakage is captured and reflected back by nose clip 40. All this occurs while the apparatus as a whole is attached securely to the nose 47.

The micro-lens structure may be designed differently to cater for different wavelengths, and to cater for a coherency factor of the light. Accordingly, the micro-lens configuration can alternatively be a reverse tear drop shape, or an oval, or an oblong shape, or any other rotund configuration, as well as be of any dimensional size which redirects light particles towards a desired direction.

Figure 13:
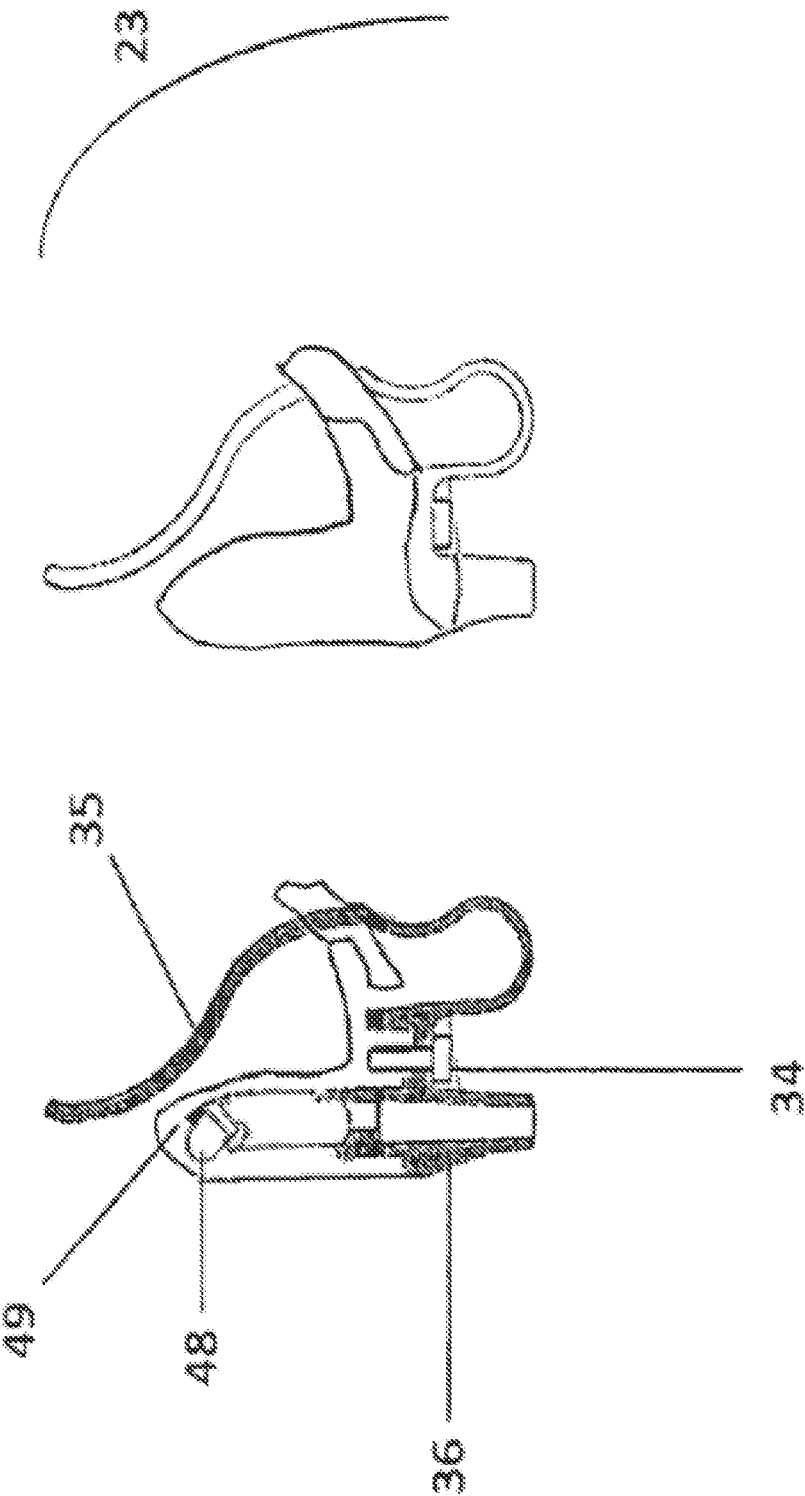
FIGS. 13a and 13b illustrate the light emitting diode embodiment of the applicator.

FIG. 13 shows an LED embodiment which depends on the mounting angle of the LED diode 48 and a side support 49 to provide the primary manipulation of the light direction. In addition the above format factors, the transparent hollow casing 35 is also configured to deflect the light back into the nasal cavity 48.

In summary, several format factors contribute to directing the generated light into the nasal cavity space and then towards the targeted areas of the brain. These include: the micro-lens 44 for the low level laser embodiment, the mounting angle for the LED embodiment 48, the hollow lens casing 35 and the nose clip 40. In this manner, the amount of electrical energy needed to achieve therapeutic efficacy is kept to a minimum, and achieves the desirable goal of the apparatus being small, portable and convenient to use.

The Self-Administrable Applicator Means for Intranasal Light Therapy Unit:

The applicator means 23 as presented by FIGS. 6-13 respectively is a purposeful grouping together of parts structurally designed to form a desirable, hand-held article which can be manipulated by the patient with his fingers and is suitable for at will attachment to and detachment from a nostril. As shown by FIGS. 6a-6b and 13a-13b in particular, it is the combination of the configured irradiation lens 39 together with the support base 34 and the nose clip 35 or 40 which collectively form and constitute the applicator means 23, and as such, the applicator means 23 is a self-administrable construction of personal convenience for the user.

It will be therefore appreciated that it is the configured irradiation lens assembly 39 which is the truly essential component, a distinct entity which is desirably held within and is supported by a cradle 36 in a supporting base 34. The cradle 36 holds and aligns the configured irradiation lens 39 for easy and rapid insertion into the nasal cavity space.

Note also that the styled nose clip 40 of the applicator 23 is a structural material arm and outward extension of the supporting base 34. Typically, the nose clip 40 is formed of a white or opaque material which is both flexible and resilient. Two different structural formats of the nose clip are shown by FIGS. 7a, 7b, 8a, 8b, 9a, and 9b respectively.

In its preferred embodiments, the nose clip serves two different purposes and functions as represented by FIG. 11. First, it is employed for direct pressure contact against and fitted frictional engagement with the exterior surface of the human nose. This engagement maintains the inserted irradiation lens in proper position within the nasal cavity space. Second, the white or opaque material of the nose clip will reduce leakage of some light particles and reflect stray light particles back into the interior tissues of the nostril. The nose clip 40 performs both of these intended functions as a merged part of the applicator 23. For these reasons, the applicator 23 as a distinct entity, and in contrast to the configured irradiation lens 39, is merely article of convenience which facilitates usage of the apparatus as a whole.

The applicator means 23 is easy to manipulate using the fingers of the human hand, and thus is a very desirable vehicle for the proper positioning of the portable casing 28 and the light generating unit 45 adjacent to the internal lining of a subject's nasal cavity in the manner shown by FIG. 12. In addition, the interchangeability of the applicator means that houses the light generator unit allows for different users in a family to have their personal applicators (for hygiene reasons) and to share a single controller and thus save the cost of having separate controllers.

Nevertheless, the self-administrable applicator means 23 shown by FIGS. 6-12 respectively is deemed to be only one preferred exemplary instance and tangible means for supporting and properly placing the configured irradiation lens 39 within a nostril, and represents only one kind of support construct which makes the in-vivo placement of the configured irradiation lens 39 within a nostril cavity easier, faster and simpler.

Figure 2:
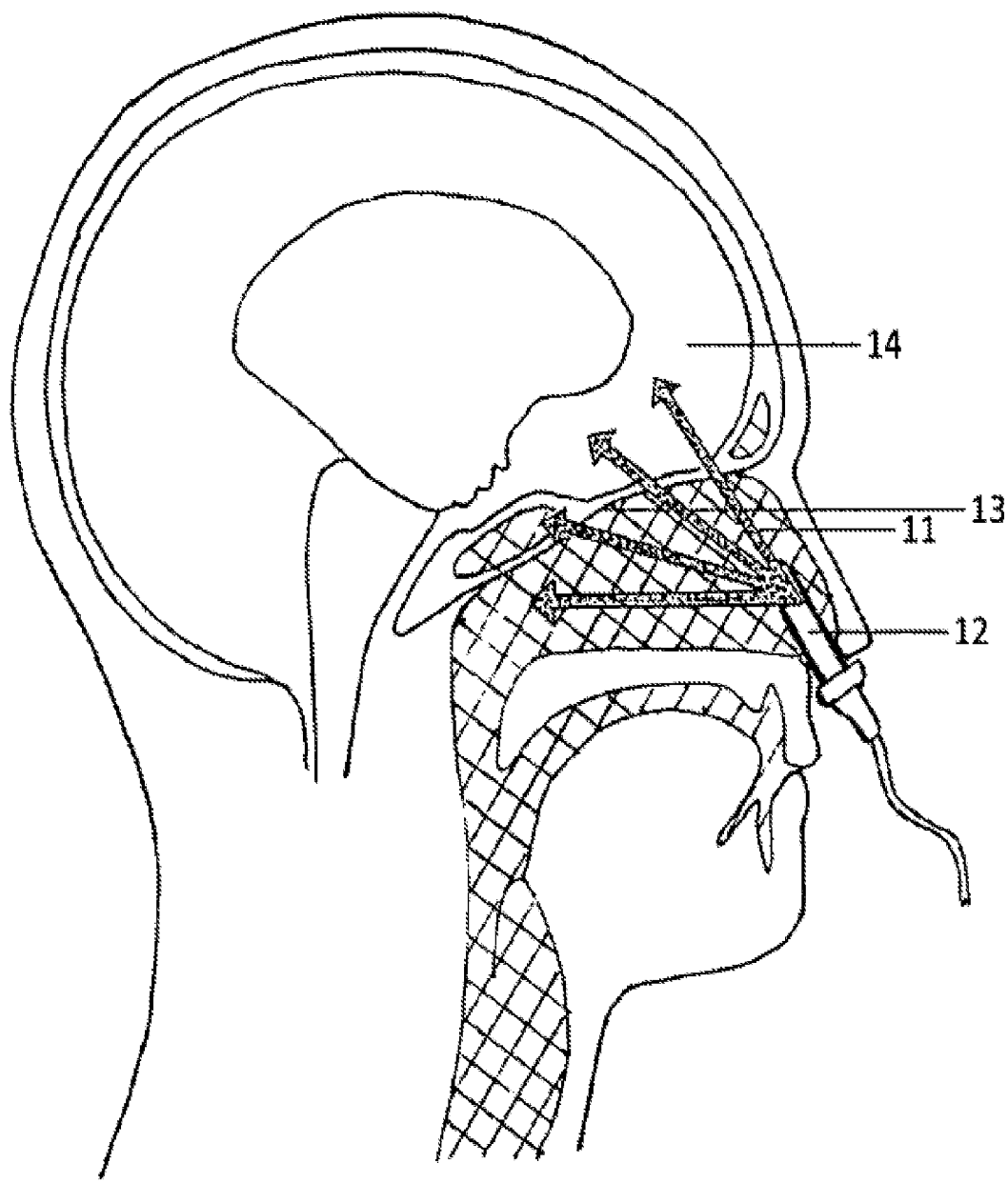
FIG. 2 illustrates the concept of how visible red light from a light emitting diode (LED) would penetrate the brain, notably with a large footprint.

Operational Parameters for Intranasal Light Therapy Unit:

The operational parameters for intranasal brain stimulation in the present invention may be broadly divided into three sub-groupings that embrace a wide range and variety of clinical applications. Conceptual representations of how the three sub-groupings target the human brain are shown by FIGS. 2, 3 and 4 respectively, and can be summarized as follows:

FIG. 2 illustrates a model system using a 633 nm LED source. The light rays 11 from the LED light source 12 are generally unimpeded and dispersed over a wide area until they reach the perpendicular plate of the ethmoid bone 13. The penetration into the brain is relatively shallow but the extensive neural network distributes the signal throughout the brain. It targets the prefrontal cortex 14 first and then the brain in general. However, the light source can be angled to point at any region of the brain as desired.

Figure 3:
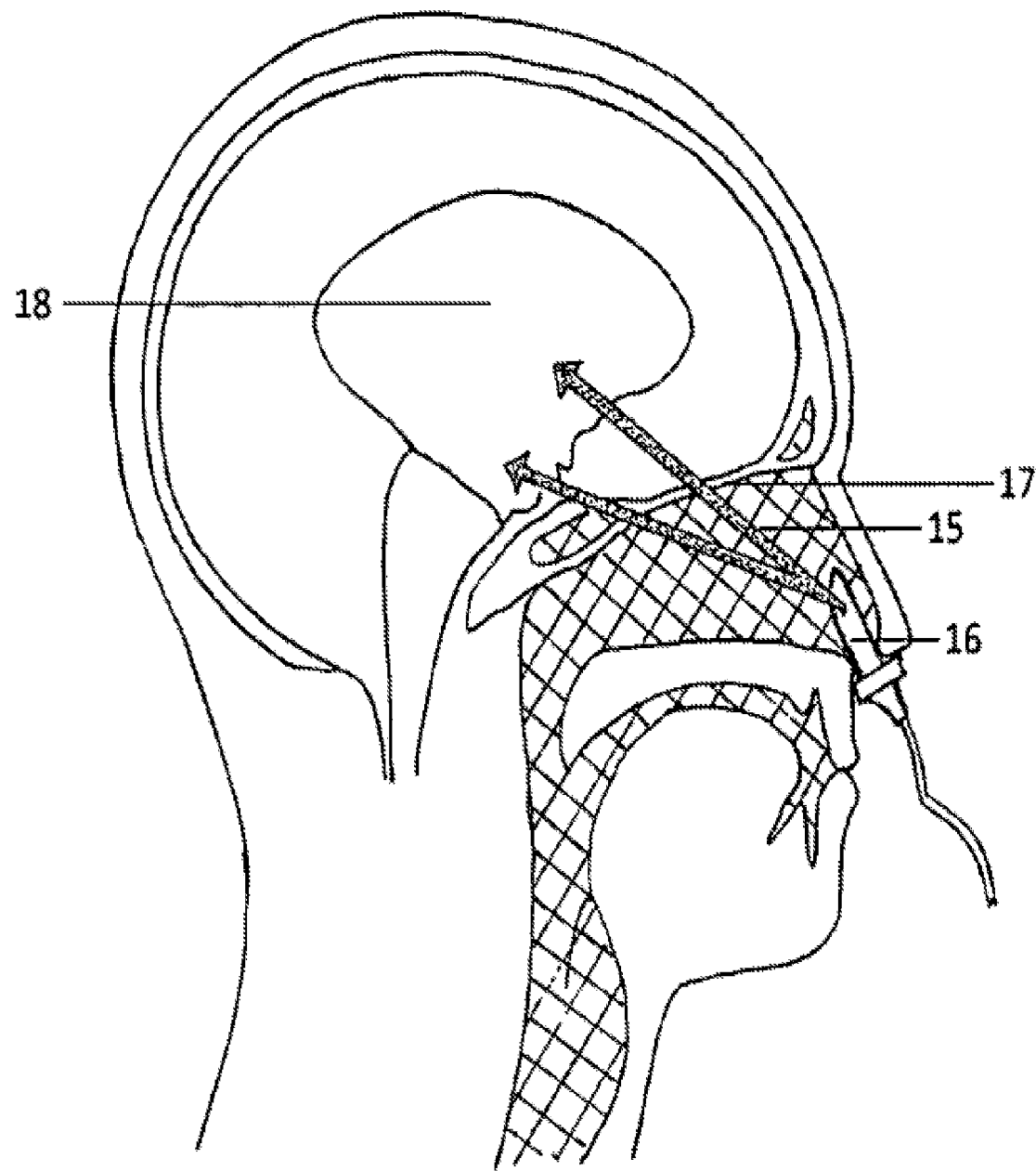
FIG. 3 illustrates the concept of the relative depth of penetration by visible red light from a low level laser diode penetrating the brain, but with a smaller footprint, when compared with the LED as illustrated in FIG. 2.

FIG. 3 illustrates a model system using a 655 nm Laser source. The light rays 15 from the laser light source 16 are generally unimpeded and generally stay coherent within a narrow dispersion until they penetrate the perpendicular plate of the ethmoid bone 17. The penetration is deeper relative to the 633 nm LED model in FIG. 2 and reaches the main targeted mid-brain region 18. However, secondary signaling will still be distributed throughout the other brain regions.

Figure 4:
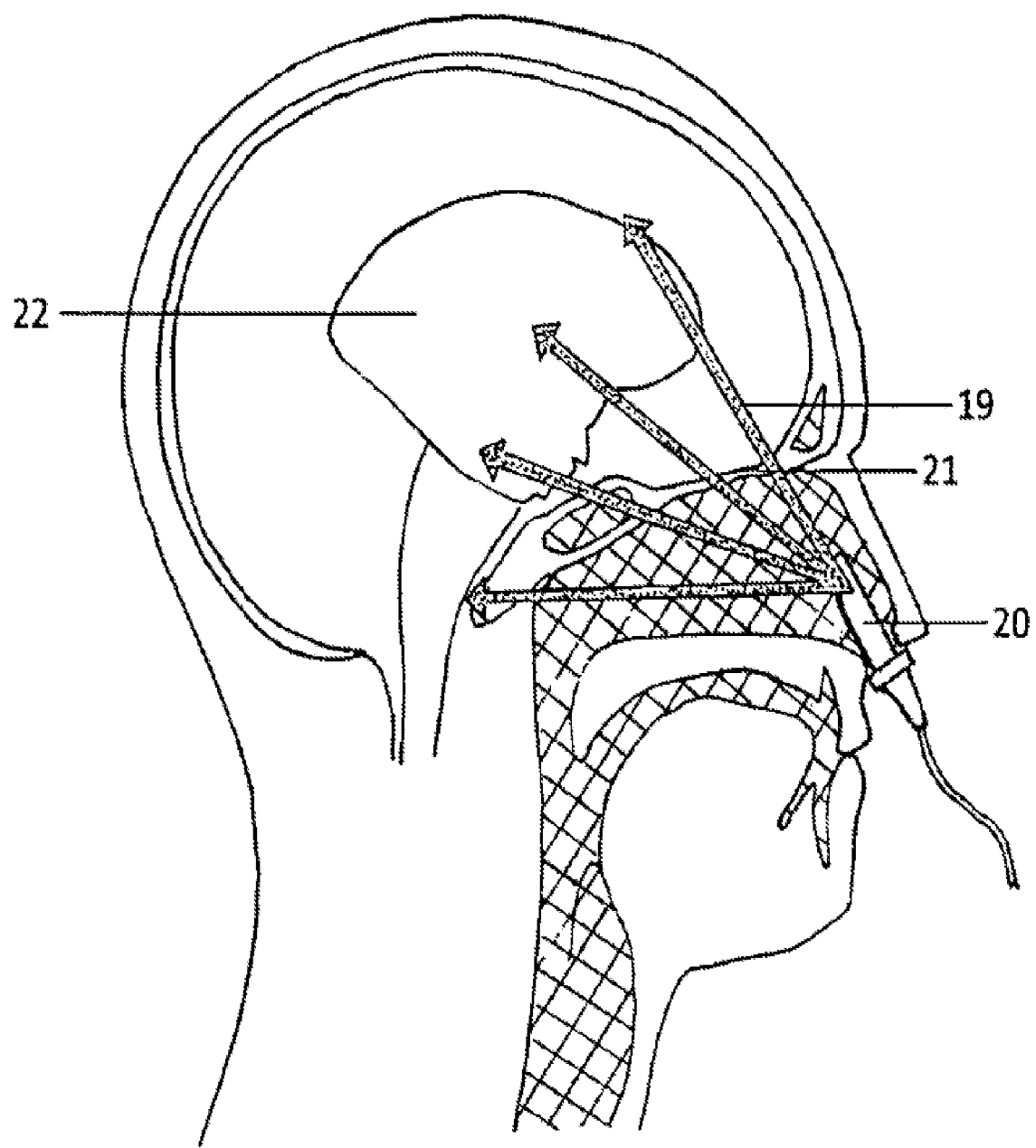
FIG. 4 illustrates the concept of the relative depth and spread of penetration by near infrared red (NIR) light from a LED diode penetrating the brain when compared with the visible red LED as illustrated in FIG. 2 and visible red low level laser as illustrated in FIG. 3.

FIG. 4 illustrates a model system using 810 nm LED light source. The light rays 19 from the LED light source 20 are generally unimpeded and dispersed over a wide area until they reach the perpendicular plate of the ethmoid bone 21. The penetration is deeper relative to the 633 nm LED model in FIG. 2 and the dispersion (and tissue coverage) is wider than the 655 nm laser in FIG. 3, covering the whole brain, including the deeper lying mid-brain area 22. This model system extracts many beneficial features of the other two models described above. The commercial disadvantage is that the light is not visible and some users may be more comfortable and safe with light rays they can see.

Attributes and Capabilities of the System and Apparatus of the Present Invention:

The apparatus provides a number of positive attributes, properties, and capabilities. Among them are the following:

1. The apparatus and system can deliver light energy over a variety of selected wavelengths to achieve therapeutic outcomes of the brain and the neural system.
2. The apparatus and system have very low electric power requirements.
3. The apparatus and system provide a lightweight transcranial headset which is more comfortable to use than a full helmet which is used in other transcranial light therapy methods.
4. The apparatus and system provide an easy to use intranasal applicator which can be clipped to the external wall of a nostril while concomitantly inserting an encased solid state electronic light source (such as the light emitting diode or a low level laser diode) within the nasal cavity to deliver the light therapy.
5. The apparatus and system overcome the disadvantages of the prior art and the limitations of conventional technologies, particularly with regards to portability and self-administration. It also markedly differs from known systems as to the method by which light therapy is delivered to the brain.

6. The apparatus and system is able to illuminate the various targeted areas of the brain by way of directing the light rays and light wavelengths. In this respect, the wavelengths of light are pre-selected so as to the desired penetration into the brain materials. This results in improved outcomes for respective neural diseases and disorders.
7. The apparatus and system separate the delivery of light energy from the processing and power controller assembly for both hygiene and cost saving purposes, and also potentially provides for the interchange and substitution of different light generating units with a single processing controller assembly that will convey the appropriate power dosage for this purpose, as well as to interface with a mobile smart phone.
8. The apparatus and system preferably combine transcranial and intranasal light therapy, wherein:
    (i) the transcranial headset directs light energy to dorsal/upper areas of the brain; and (ii) the intranasal unit directs light energy to the ventral or underside of the brain. This provides more comprehensive coverage than current transcranial methods alone and current intranasal methods alone.
9. The apparatus and system preferably targets specific cortical hubs of the Default Mode Network, thus aiming to heal lesions in the hubs associated with brain disorders such as Alzheimer's disease and dementia.

The Method of Therapeutic Treatment:

The system and apparatus described above can be used in a preferred method of the present invention. In this method, light energy is preferably delivered to the targeted cortical hubs of the DMN. As mentioned above, lesions in these cortical hubs are associated with many brain disorders, such as Alzheimer's disease and dementia. The effective delivery of light to these damaged areas aims to stimulate healing. In particular, the light attracts the leading edge of growth cones in the brain cells so as to draw growth in the direction of the light. At the cellular level, the photoacceptor respiratory enzyme cytochrome oxidase is particularly sensitive to light in the visible red region and near-infrared region of the light spectrum, and converts the absorbed light of these red and near-infrared wavelengths into cellular energy molecules of adenosine triphosphate (ATP). There is a resulting increase in ATP synthesis and oxygen consumption, thus improving mitochondrial metabolism in-vivo. This preferably promotes growth and healing of the neuronal cells and aims to improve the condition of the brain disorder.

The method for performing non-invasive irradiation light therapy in order to achieve brain neurostimulation in a living mammalian subject preferably comprises the following steps and actions:

Step 1: Obtaining a light energy-emitting apparatus comprised of:
    first, second, third and fourth configured irradiation units, each of said first, second, third and fourth configured irradiation units comprising a portable hollow casing having fixed dimensions, a sized internal spatial volume and an external surface configuration suitable for application to the skull, said portable hollow casing of each configured irradiation unit being comprised of:
        (i) a light energy transmitting material which forms at least a portion of the configured external surface for said hollow casing of each configured irradiation unit; and
        (ii) at least one light generating unit entirely housed and contained within said internal spatial volume of said hollow casing of each configured irradiation unit and which is capable of generating light energy of at least one preselected wavelength selected from the group consisting of near infrared red light wavelengths and visible red light wavelengths, at a predetermined energy intensity and for a preset time duration on-demand sufficient to penetrate through the skull and to pass into the brain,
    whereby said first, second, third and fourth configured irradiation units can emit light energy after application to the skull and achieve passage of said emitted light energy through the skull into at least one portion of the brain in-vivo;
    a frame adapted for support of said first, second, third and fourth configured irradiation units and for at will placement of said light transmitting external surface of said first, second, third and fourth configured irradiation units at a fixed position and desired irradiation direction on the skull;
    a portable controller assembly able to control on-demand delivery of light energy from said configured irradiation units into at least one portion of the brain in-vivo, said controller assembly including:
        (a) a portable and replenishable power source of on-demand direct electrical current,
        (b) a central processing unit for controlling and directing the flow of such direct electrical current,
        (c) at least one connector in electrical communication with the power source for on-demand conveyance of direct electrical current to the central processing unit, and
        (d) at least one connector in electrical communication with the configured irradiation units for on-demand conveyance of direct electrical current from said central processing unit to said light generating units;
    wherein said light energy-emitting apparatus further comprises:
    a configured irradiation lens including:
        a portable hollow casing having fixed dimensions, a sized internal spatial volume, and an external surface configuration suitable for in-vivo insertion into the nasal cavity space of a nostril without causing substantial impairment to the subject's ability to breathe and without invading the nasal tissues of the living subject, said portable casing of said configured irradiation lens being comprised of:
            (i) a light energy transmitting material which forms at least a portion of the configured external surface for said hollow casing of said configured irradiation lens,
            (ii) at least one light generating unit entirely housed and contained within said internal spatial volume of said hollow casing of said configured irradiation lens and which is capable of generating light energy of at least one preselected wavelength selected from the group consisting of near infrared red light wavelengths and visible red light wavelengths, at a predetermined energy intensity and for a preset time duration on-demand sufficient to penetrate through the nasal tissues and to pass into the brain,
        whereby said configured irradiation lens can emit light energy in any desired direction within the nasal cavity after in-vivo insertion and achieve passage of said emitted light energy from the nasal cavity into at least one portion of the brain in-vivo;

a self-administrable applicator means adapted for support of said configured irradiation lens and for at will placement of said light transmitting external surface of said configured irradiation lens at a fixed position and desired irradiation direction within a nostril adjacent to the internal lining of a subject's nasal cavity;

wherein said portable controller assembly is further able to control on-demand delivery of light energy from said configured irradiation lens.

Step 2: Placing a transparent external surface of said first, second, third and fourth configured irradiation units at a desired fixed position adjacent to the skull of a subject such that light energy emitted by said first, second, third and fourth configured irradiation units will penetrate through the subject's skull and pass into at least one portion of the brain in-vivo; and placing a transparent external surface of said configured irradiation lens within a nostril at a desired fixed position adjacent to the internal lining of a subject's nasal cavity such that light energy emitted by said configured irradiation lens will penetrate through the subject's nasal tissues and pass into at least one portion of the brain in-vivo.

Step 3: Causing said light generating units of said positioned configured irradiation units to generate light energy of at least one preselected wavelength selected from the group consisting of near infrared red light wavelengths and visible red light wavelengths, at a predetermined energy intensity and for a preset time duration on-demand sufficient to penetrate through the subject's skull and to pass into the brain such that neurostimulation of at least one portion of the brain is achieved; and causing said light generating units of said positioned configured irradiation lens to generate light energy of at least one preselected wavelength selected from the group consisting of near infrared red light wavelengths and visible red light wavelengths, at a predetermined energy intensity and for a preset time duration on-demand sufficient to penetrate through the subject's nasal tissues and to pass into the brain such that neurostimulation of at least one portion of the brain is achieved.

Figure 23:
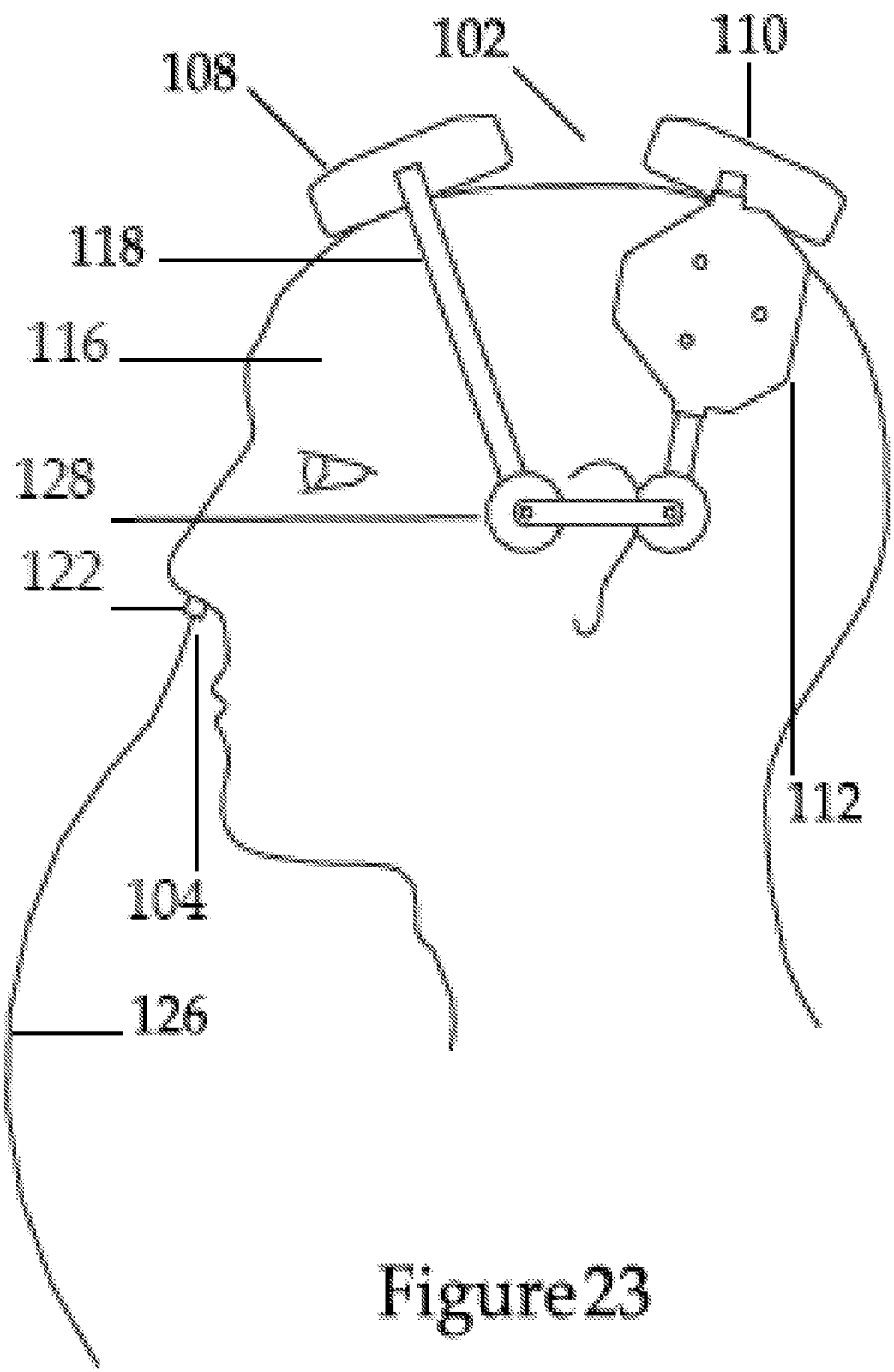
FIG. 23 illustrates a left view of a preferred embodiment of the apparatus of the present invention.

As shown in FIGS. 23 and 24, the transcranial headset 102 is placed on the head of the subject. The configured irradiation units 108, 110, 112 and 114 are supported by the frame 118. Furthermore, the configured irradiation units 108, 110, 112 and 114 are positioned relative to each other such that, when the transcranial headset 102 is placed on the subject's head, the external surface of each configured irradiation units 108, 110, 112 and 114 is adjacent to a target position on the skull. Preferably, as illustrated in FIG. 25, the configured irradiation units 108, 110, 112 and 114 are positioned to direct light energy through the skull to the following respective regions in the brain:

(A) a first region of the brain comprising the left and right ventral mesial prefrontal cortex areas, and optionally, the anterior cingulate gyrus areas;

(B) a second region of the brain comprising the left and right precuneus cortical areas, and optionally, the posterior cingulate gyrus areas;

(C) a third region of the brain comprising the left angular gyrus area in the lateral, inferior parietal cortex, and optionally, the left posterior cingulate gyrus; and (D) a fourth region of the brain comprising the right angular gyrus area in the lateral, inferior parietal cortex, and optionally, the right, posterior cingulate gyrus.

A configured irradiation lens 122 is placed inside one of the nostrils of the subject. The external surface of the configured irradiation lens 122 is positioned so as to direct energy through the nasal cavity and into the brain. The nose clip 120 is used to hold the configured irradiation lens 122 in position inside the nostril of the subject.

When desired by the subject, a direct electric current is conveyed from the portable controller assembly 106, through the first connector 124, and to the light generating units of the configured irradiation units 108, 110, 112 and 114. This causes the light generating units in the configured irradiation units 108, 110, 112 and 114 to generate light energy of at least one preselected wavelength selected from the group consisting of near infrared red light wavelengths and visible red light wavelengths, at a predetermined energy intensity and for a preset time duration on-demand sufficient to penetrate through the subject's skull and to pass to the targeted regions of the brain.

Also, when desired by the subject, a direct electric current is conveyed from the portable controller assembly 106, through the second connector 126, and to the light generating unit(s) of the configured irradiation lens 122. This causes the light generating unit(s) in the configured irradiation lens 122 to generate light energy of at least one preselected wavelength selected from the group consisting of near infrared red light wavelengths and visible red light wavelengths, at a predetermined energy intensity and for a preset time duration on-demand sufficient to penetrate through the subject's nasal cavity and to pass to the brain.

More specific details regarding the steps using the intranasal unit can be seen in FIG. 10, where one inserts the configured irradiation lens 35 using the self-administrable applicator means 23 into the nasal cavity space 2 of the human nose, and then causes direct electric current to be conveyed from its source to the process controller assembly (not shown) and then to the light unit(s) 35 disposed within the hollow casing 39. This will cause the light unit 45 to generate and transmit light waves and particles 46 of a pre-chosen wavelength.

In the preferred laser light embodiments, the transmitted light waves and particles 46 are directed and deflected by the casing wall 40 and the micro-lens 44 that is capped over the light generating unit 45 within the hollow casing 35. This is illustrated best by FIGS. 11 and 12 respectively.

By this process, the light waves and particles 46 emanating from the configured irradiating lens 35 become focused, aimed, and directed towards entering the various regions of the brain, as illustrated in FIG. 1. The aimed light energy from the light generating unit 45 is largely deflected towards the internal section of the nasal cavity; and such light as might pass through the entire nasal cavity 2 and leaked light is then reflected and redirected back into the nasal cavity space by the reflective white opaque material of the nose clip 40. Thus, as shown by FIG. 12, most of the initially generated light is captured and aimed (by deflection and reflection) into the nasal cavity 2.

In these embodiments, the process and power controller assembly as a whole is able to deliver a dosage of the desired energy measured in Joules/cm$^2$, which is sufficient to achieve consistent therapeutic stimulation of the brain. Also, the battery source of electric energy within the controller assembly provides direct current and the CPU of the controller assembly is able to regulate total light energy power output consistently at 10 to 1000 mW. The energy density being delivered is in the range of about 5 to 1800 J/cm$^2$. This results in the emitted light of the apparatus being therapeutically effective after a treatment time of only 10 to 30 minutes duration, preferably 20 to 25 minutes. In the alternative, the functions and work of the power controller may alternatively be performed by a smart phone with the appropriate downloaded "App".

Study No. 1:

The inventor and co-investigators carried out a study to test the effectiveness of the system, apparatus and method of the present invention on 18 randomly selected subjects with Alzheimer's disease and dementia. Assessments with standard cognitive and functional scales were made at the baseline (Week 0) and Week 12. 12 of the subjects were treated with the system and apparatus of the present invention. 6 subjects were treated with a placebo devices.

Results

At Week 12, all the subjects who were treated with the real system and apparatus of the present invention showed improvements in memory/cognition and functional abilities to varying degrees. As for those on the placebo devices, 2 of the subjects displayed marginal improvements while the remaining 4 continued to decline.

Comparison and Indications with Drugs

This is the first medical modality to produce improvements in memory/cognition and functional abilities in a randomized placebo-controlled study on Alzheimer's disease and dementia patients. As of yet, there are no pharmaceutical options that provide significant positive results and all have significant negative side effects. Additionally, the drugs in the pipeline are offering to slow down cognitive decline, not to improve it. The system and apparatus of the present invention have not added any noticeable negative side effects. There have also been no contraindications in volunteers who have continued with their medications.

Study No. 2:

A study was conducted on a patient suffering from anxiety. The patient was given a single treatment with the system and apparatus of the present invention for 20 minutes.

Quantitative Electroencephalography (QEEG) tests are commonly used to measure and analyze the electrical activity of the brain and can detect abnormalities in the brain's neural oscillations or brain waves. QEEG has been used to diagnose epilepsy, cerebro-vascular disorders and other conditions. QEEG tests were conducted on the patient at two points in time: (i) prior to treatment with the system and apparatus of the present invention; and (ii) after a 20 minute treatment with the system and apparatus of the present invention. The results are shown in FIG. 30.

Figure 30:
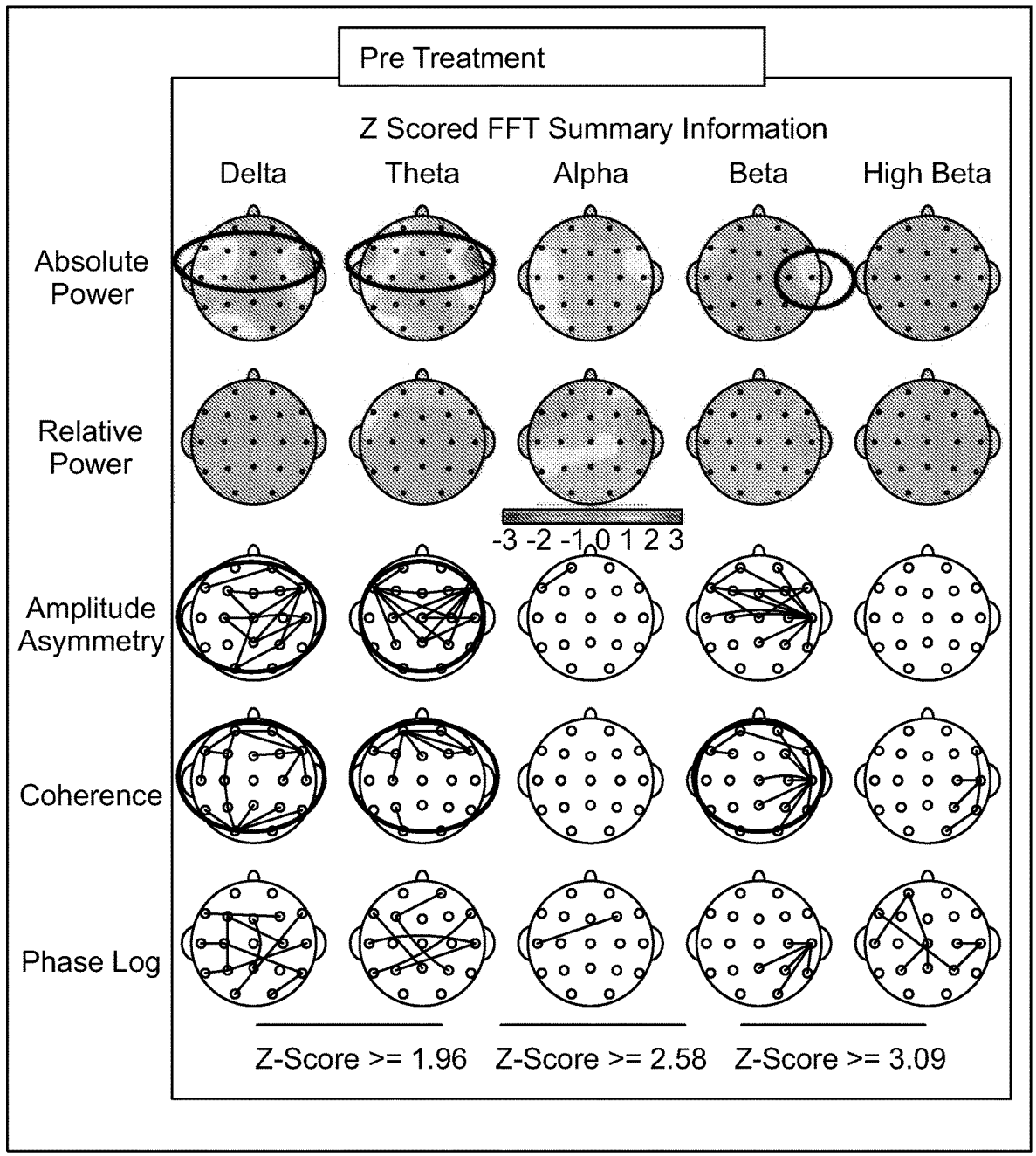
FIG. 30 illustrates the results of Quantitative Electroencephalography tests performed pre-treatment with the system and apparatus of the present invention of a patient with anxiety.
Figure 31:
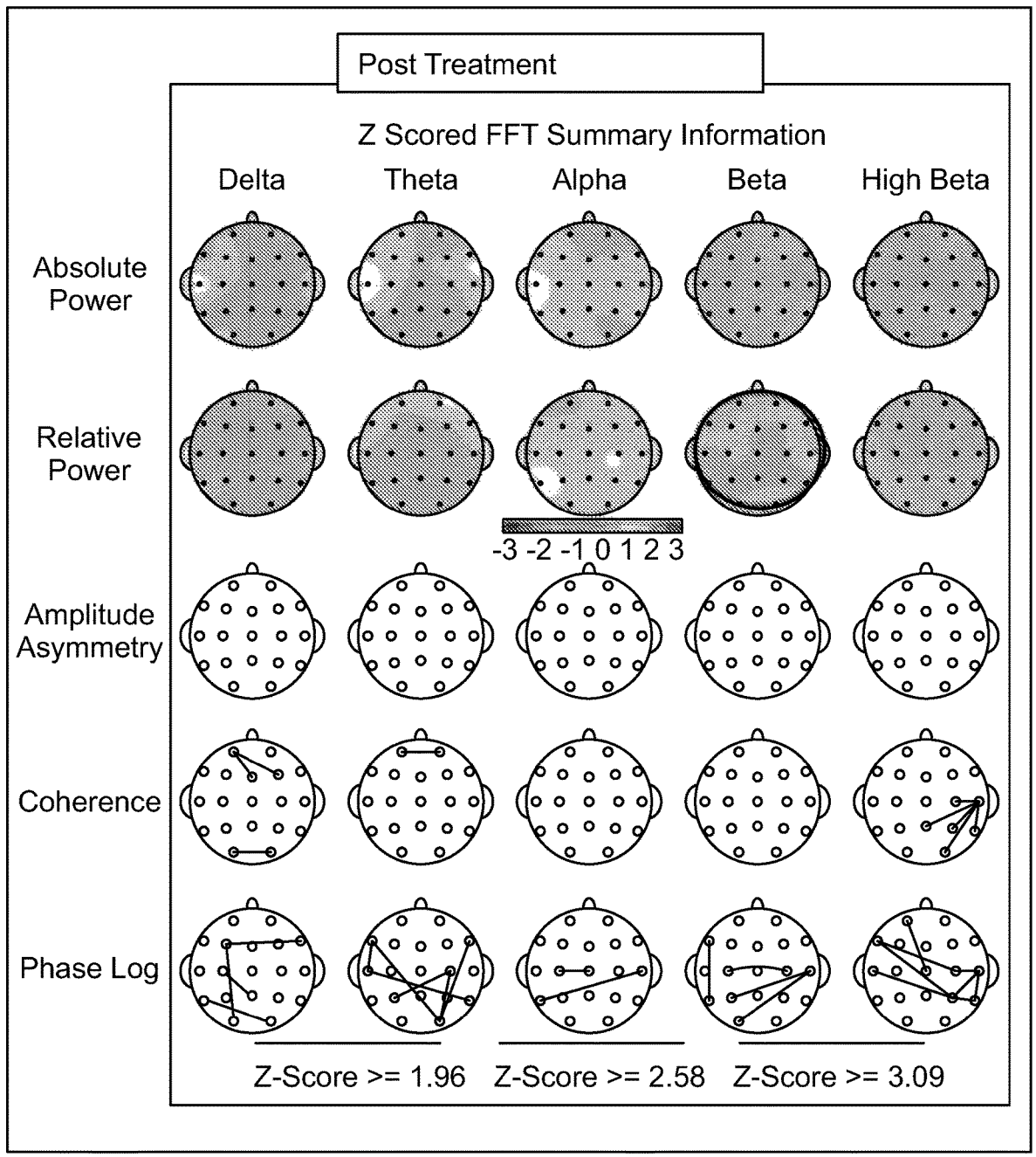
FIG. 31 illustrates the results of Quantitative Electroencephalography tests performed post-treatment with the system and apparatus of the present invention of a patient with anxiety.

As can be seen in FIG. 30, prior to treatment with the system and apparatus of the present invention, there were several abnormalities in the patient's brain waves detected by the QEEG. For example, abnormalities are indicated by the circle areas in the first, third and fourth rows. However, as shown in FIG. 31, after a single 20 minute treatment, many of those abnormalities were either removed or diminished, especially in the first row of the QEEG. This is a remarkable improvement after only a single 20 minute treatment.

The scope of the claims should not be limited by the preferred embodiments set forth in the examples, but should be given the broadest interpretation consistent with the description as a whole.

The invention claimed is:

1. A self-administrable system for performing non-invasive neurostimulation therapy of the brain of a living mammal on-demand, said self-administrable non-invasive neurostimulation system comprising:
   configured irradiation units consisting of a first, a second, a third and a fourth configured irradiation unit, each of said first, second, third and fourth configured irradiation units comprising a portable hollow casing having fixed dimensions, a sized internal spatial volume and an external surface configuration suitable for application to the skull, said portable hollow casing of each configured irradiation unit being comprised of:
   (i) a light energy transmitting material which forms at least a portion of the configured external surface for said hollow casing of each configured irradiation unit; and
   (ii) at least one light generating unit housed and contained within said internal spatial volume of said hollow casing of each configured irradiation unit and which is capable of generating light energy of at least one preselected wavelength selected from the group consisting of near infrared light wavelengths and visible red light wavelengths, at a predetermined energy intensity and for a preset time duration on-demand sufficient to penetrate through the skull and to pass into the brain,
   whereby said first, second, third and fourth configured irradiation units can emit light energy after application to the skull and achieve passage of said emitted light energy through the skull into at least one portion of the brain in-vivo;
   a frame adapted for support of said first, second, third and fourth configured irradiation units and for at will placement of said light transmitting external surface of said first, second, third and fourth configured irradiation units at a fixed position and desired irradiation direction on the skull;
   a portable controller assembly able to control on-demand delivery of light energy from said configured irradiation units into at least one portion of the brain in-vivo, said controller assembly including:
   (a) a portable and replenishable power source of on-demand direct electrical current,
   (b) a central processing unit for controlling and directing the flow of such direct electrical current,
   (c) at least one connector in electrical communication with the power source for on-demand conveyance of direct electrical current to the central processing unit, and
   (d) at least one connector in electrical communication with the configured irradiation units for on-demand conveyance of direct electrical current from said central processing unit to said light generating units;
   wherein:
   (A) said first configured irradiation unit is positioned to direct light energy to a first region of the brain comprising the left and right ventral mesial prefrontal cortex areas, and optionally, the anterior cingulate gyrus areas;
   (B) said second configured irradiation unit is positioned to direct light energy to a second region of the brain comprising the left and right precuneus cortical areas, and optionally, the posterior cingulate gyrus areas;
   (C) said third configured irradiation unit is positioned to direct light energy to a third region of the brain comprising the left angular gyrus area in the lateral, inferior parietal cortex, and optionally, the left posterior cingulate gyrus; and
   (D) said fourth configured irradiation unit is positioned to direct light energy to a fourth region of the brain comprising the right angular gyrus area in the lateral, inferior parietal cortex, and optionally, the right posterior cingulate gyrus.

2. The system of claim 1, said system further comprising:
a configured irradiation lens including:
a portable hollow casing having fixed dimensions, a sized internal spatial volume, and an external surface configuration suitable for in-vivo insertion into the nasal cavity space of a nostril without causing substantial impairment to the subject's ability to breathe and without invading the nasal tissues of the living subject, said portable casing of said configured irradiation lens being comprised of:
(i) a light energy transmitting material which forms at least a portion of the configured external surface for said hollow casing of said configured irradiation lens,
(ii) at least one light generating unit housed and contained within said internal spatial volume of said hollow casing of said configured irradiation lens and which is capable of generating light energy of at least one preselected wavelength selected from the group consisting of near infrared light wavelengths and visible red light wavelengths, at a predetermined energy intensity and for a preset time duration on-demand sufficient to penetrate through the nasal tissues and to pass into the brain,
whereby said configured irradiation lens can emit light energy in any desired direction within the nasal cavity after in-vivo insertion and achieve passage of said emitted light energy from the nasal cavity into at least one portion of the brain in-vivo;
a self-administrable applicator means adapted for support of said configured irradiation lens and for at will placement of said light transmitting external surface of said configured irradiation lens at a fixed position and desired irradiation direction within a nostril adjacent to the internal lining of a subject's nasal cavity;
wherein said portable controller assembly is further able to control on-demand delivery of light energy from said configured irradiation lens.

3. The system of claim 1, said system further comprising at least one power switch which engages and disengages the transfer of direct electrical current from said controller assembly to said configured irradiation units.

4. The system of claim 1, wherein said controller assembly regulates the power to about 10 to 1000 mW.

5. The system of claim 1, wherein the light energy is pulsed at a frequency of 10 Hz.

6. The system of claim 1, wherein the light energy density is in the range of about 5 to 1800 J/cm2.

7. The system of claim 1, wherein the patient exposure time for each therapeutic treatment session is from about 10 to 30 minutes in duration.

8. A self-administrable method for performing non-invasive neurostimulation therapy of the brain via a nasal cavity and through the skull of a living mammalian on-demand, said self-administrable non-invasive neurostimulation method comprising the steps of:
obtaining a light energy-emitting apparatus comprised of:
configured irradiation units consisting of a first, a second, a third and a fourth configured irradiation unit, each of said first, second, third and fourth configuration units comprising a portable hollow casing having fixed dimensions, a sized internal spatial volume and an external surface configuration suitable for application to the skull, said portable hollow casing of each configured irradiation unit being comprised of:
(i) a light energy transmitting material which forms at least a portion of the configured external surface for said hollow casing of each configured irradiation unit; and
(ii) at least one light generating unit housed and contained within said internal spatial volume of said hollow casing of each configured irradiation unit and which is capable of generating light energy of at least one preselected wavelength selected from the group consisting of near infrared light wavelengths and visible red light wavelengths, at a predetermined energy intensity and for a preset time duration on-demand sufficient to penetrate through the skull and to pass into the brain,
whereby said first, second, third and fourth configured irradiation units can emit light energy after application to the skull and achieve passage of said emitted light energy through the skull into at least one portion of the brain in-vivo;
a frame adapted for support of said first, second, third and fourth configured irradiation units and for at will placement of said light transmitting external surface of said first, second, third and fourth configured irradiation units at a fixed position and desired irradiation direction on the skull;
a portable controller assembly able to control on-demand delivery of light energy from said configured irradiation lenses into at least one portion of the brain in-vivo, said controller assembly including:
(a) a portable and replenishable power source of on-demand direct electrical current,
(b) a central processing unit for controlling and directing the flow of such direct electrical current, (c) at least one connector in electrical communication with the power source for on-demand conveyance of direct electrical current to the central processing unit, and
(d) at least one connector in electrical communication with the configured irradiation units for on-demand conveyance of direct electrical current from said central processing unit to said light generating units;
placing a transparent external surface of said first, second, third and fourth configured irradiation units at a desired fixed position adjacent to the skull of a subject such that light energy emitted by said first, second, third and fourth configured irradiation units will penetrate through the subject's skull and pass into at least one portion of the brain in-vivo; and
causing said light generating units of said positioned configured irradiation units to generate light energy of at least one preselected wavelength selected from the group consisting of near infrared light wavelengths and visible red light wavelengths, at a predetermined energy intensity and for a preset time duration on-demand sufficient to penetrate through the subject's skull and to pass into the brain such that neurostimulation of at least one portion of the brain is achieved;
wherein:
(A) said first configured irradiation unit is positioned to direct light energy to a first region of the brain comprising the left and right ventral mesial prefrontal cortex areas, and optionally, the anterior cingulate gyrus areas;
(B) said second configured irradiation unit is positioned to direct light energy to a second region of the brain comprising the left and right precuneus cortical areas, and optionally, the posterior cingulate gyrus areas;
(C) said third configured irradiation unit is positioned to direct light energy to a third region of the brain comprising the left angular gyrus area in the lateral, inferior parietal cortex, and optionally, the left posterior cingulate gyrus; and (D) said fourth configured irradiation unit is positioned to direct light energy to a fourth region of the brain comprising the right angular gyrus area in the lateral, inferior parietal cortex, and optionally, the right posterior cingulate gyrus.

9. The method of claim 8, wherein said light energy-emitting apparatus further comprises:

a configured irradiation lens including:

a portable hollow casing having fixed dimensions, a sized internal spatial volume, and an external surface configuration suitable for in-vivo insertion into the nasal cavity space of a nostril without causing substantial impairment to the subject's ability to breathe and without invading the nasal tissues of the living subject, said portable casing of said configured irradiation lens being comprised of:

(i) a light energy transmitting material which forms at least a portion of the configured external surface for said hollow casing of said configured irradiation lens, (ii) at least one light generating unit housed and contained within said internal spatial volume of said hollow casing of said configured irradiation lens and which is capable of generating light energy of at least one preselected wavelength selected from the group consisting of near infrared light wavelengths and visible red light wavelengths, at a predetermined energy intensity and for a preset time duration on-demand sufficient to penetrate through the nasal tissues and to pass into the brain, whereby said configured irradiation lens can emit light energy in any desired direction within the nasal cavity after in-vivo insertion and achieve passage of said emitted light energy from the nasal cavity into at least one portion of the brain in-vivo;

a self-administrable applicator means adapted for support of said configured irradiation lens and for at will placement of said light transmitting external surface of said configured irradiation lens at a fixed position and desired irradiation direction within a nostril adjacent to the internal lining of a subject's nasal cavity;

wherein said portable controller assembly is further able to control on-demand delivery of light energy from said configured irradiation lens;

wherein said method further comprises:

placing a transparent external surface of said configured irradiation lens within a nostril at a desired fixed position adjacent to the internal lining of a subject's nasal cavity such that light energy emitted by said configured irradiation lens will penetrate through the subject's nasal tissues and pass into at least one portion of the brain in-vivo; and causing said light generating units of said positioned configured irradiation lens to generate light energy of at least one preselected wavelength selected from the group consisting of near infrared light wavelengths and visible red light wavelengths, at a predetermined energy intensity and for a preset time duration on-demand sufficient to penetrate through the subject's nasal tissues and to pass into the brain such that neurostimulation of at least one portion of the brain is achieved.

10. The method of claim 8, wherein the light is selected from the group consisting of coherent and non-coherent waves.

11. The method of claim 8, wherein the light wave type is selected from the group consisting of continuous and pulsed waves.

12. The method of claim 8, wherein the light energy is pulsed at a frequency of 10 Hz.

13. The method of claim 8, wherein the light energy density is in the range of about 5 to 1800 J/cm$^2$.

14. The method of claim 8, wherein the total power is in the range of 10 to 1000 mW.

15. The method of claim 8, wherein the patient exposure time for each therapeutic treatment session is from about 10 to 30 minutes in duration.

* * * * *